US010035980B2

(12) United States Patent
Li et al.

(10) Patent No.: US 10,035,980 B2
(45) Date of Patent: Jul. 31, 2018

(54) EXTRACELLULAR MATRIX DERIVED FROM STEM CELLS AND METHODS FOR PRODUCTION

(71) Applicant: FLORIDA STATE UNIVERSITY RESEARCH FOUNDATION, INC., Tallahassee, FL (US)

(72) Inventors: Yan Li, Tallahassee, FL (US); Teng Ma, Tallahassee, FL (US); Sebastien Sart, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 0 days.

(21) Appl. No.: 14/760,945

(22) PCT Filed: Jan. 14, 2014

(86) PCT No.: PCT/US2014/011518
§ 371 (c)(1),
(2) Date: Jul. 14, 2015

(87) PCT Pub. No.: WO2014/110586
PCT Pub. Date: Jul. 17, 2014

(65) Prior Publication Data
US 2015/0337261 A1 Nov. 26, 2015

Related U.S. Application Data

(60) Provisional application No. 61/752,205, filed on Jan. 14, 2013.

(51) Int. Cl.
*C12N 5/0735* (2010.01)
*A61K 35/12* (2015.01)
*A61K 35/545* (2015.01)
*A61K 9/00* (2006.01)
*A61L 27/36* (2006.01)
*A61L 27/38* (2006.01)
*A61L 27/50* (2006.01)
*C12N 5/00* (2006.01)

(52) U.S. Cl.
CPC .......... *C12N 5/0068* (2013.01); *A61K 9/0019* (2013.01); *A61K 35/12* (2013.01); *A61K 35/545* (2013.01); *A61L 27/365* (2013.01); *A61L 27/3633* (2013.01); *A61L 27/3675* (2013.01); *A61L 27/3834* (2013.01); *A61L 27/3895* (2013.01); *A61L 27/50* (2013.01); *C12N 5/0606* (2013.01); *A61L 2300/412* (2013.01); *A61L 2300/64* (2013.01); *A61L 2430/02* (2013.01); *A61L 2430/32* (2013.01); *C12N 2501/155* (2013.01); *C12N 2501/235* (2013.01); *C12N 2513/00* (2013.01); *C12N 2533/90* (2013.01)

(58) Field of Classification Search
None
See application file for complete search history.

(56) References Cited

FOREIGN PATENT DOCUMENTS

| WO | WO-02/40630 | 5/2002 |
|---|---|---|
| WO | WO-2007/025233 | 3/2007 |
| WO | WO-2012/033763 | 3/2012 |
| WO | WO-2012/142569 | 10/2012 |

OTHER PUBLICATIONS

Nair, et al. (2008) "Acellular matrices derived from differentiating embryonic stem cells", Journal of Biomedical Materials Research, Part A, 87(4): 1075-85.*
Sart, et al. (2016) "Crosslinking of extracellular matrix scaffolds derived from pluripotent stem cell aggregates modulates neural differentiation", Acta Biomaterialia, 30: 222-32.*
Azarin, S.M., et al., "Modulation of Wnt/beta-catenin signaling in human embryonic stem cells using a 3-D microwell array," *Biomaterials*, 2012, vol. 33, pp. 2041-2049.
Badylak, S.F., et al., "Extracellular matrix as a biological scaffold material: Structure and function," *Acta Biomater.*, 2009, vol. 5, pp. 1-13.
Banerjee, A., et al., "The influence of hydrogel modulus on the proliferation and differentiation of encapsulated neural stem cells," *Biomaterials*, 2009, vol. 30, pp. 4695-4699.
Belatik, A., et al., "Binding sites of retinol and retinoic acid with serum albumins," *Eur. J. Med. Chem.*, 2012, vol. 48, pp. 114-123.
Brafman, D.A., et al., "Defining long-term maintenance conditions of human embryonic stem cells with arrayed cellular microenvironment technology," *Stem Cells Dev.*, 2009, vol. 18, p. 1141-1154.
Bratt-Leal, A.M., et al., "Engineering the embryoid body microenvironment to direct embryonic stem cell differentiation," *Biotechnol. Prog.*, 2009, vol. 25, p. 43-51.

(Continued)

*Primary Examiner* — Robert M Kelly
(74) *Attorney, Agent, or Firm* — Saliwanchik Lloyd & Eisenschenk

(57) ABSTRACT

The subject invention pertains to acellular extracellular matrix (ECM) and methods for preparing it. In one embodiment, the ECM is prepared from 3-D aggregates of pluripotent stem cells or from embryoid bodies. In one embodiment, the ECM is in the form of acellular microspheres. The stem cells used in the present invention can be embryonic stem cells (ESC). In a specific embodiment, the stem cells or embryoid bodies are from human. The ECM of the invention can be mass produced using PSC aggregates or embryoid bodies in large scale bioreactors. The acellular ECM produced using the present invention can be used for injection into a person or animal to regenerate tissue and/or treat a disease or condition. A method of the invention comprises growing stem cells in suspension culture as aggregates, e.g., in a bioreactor. Acellular ECM is then prepared from the cell aggregates by decellularization. In a specific embodiment, a decellularization reagent comprising Triton X-100 is used, followed by treatment with a DNase.

19 Claims, 35 Drawing Sheets

(56) References Cited

OTHER PUBLICATIONS

Bratt-Leal, A.M., et al., "Incorporation of biomaterials in multicellular aggregates modulates pluripotent stem cell differentiation," *Biomaterials*, 2011, vol. 32, pp. 48-56.

Butler, M.F., et al., "Mechanism and kinetics of the crosslinking reaction between biopolymers containing primary amine groups and Genipin," *Journal of Polymer Science: Part A: Polymer Chemistry*, 2003, vol. 41, pp. 3941-3953.

Cai, C., et al., "Directing the differentiation of embryonic stem cells to neural stem cells," *Dev. Dyn.*, 2007, vol. 236, pp. 3255-3266.

Carpenedo, R.L., et al., "Homogeneous and organized differentiation within embryoid bodies induced by microsphere-mediated delivery of small molecules," *Biomaterials*, 2009, vol. 30, pp. 2507-2515.

Chen, N., et al., "All-trans-retinoic acid stimulates translation and induces spine formation in hippocampal neurons through a membrane-associated RARalpha," *FASEB Journal*, 2008, vol. 22, pp. 236-245.

Chen, S.S., et al., "Cell-cell and cell-extracellular matrix interactions regulate embryonic stem cell differentiation," *Stem Cells*, 2007, vol. 25, pp. 553-561.

Choi, J.S., et al., "ecellularized extracellular matrix derived from human adipose tissue as a potential scaffold for allograft tissue engineering," *J. Biomed. Mater. Res. A*, 2011, vol. 97, pp. 292-299.

Choi, J.S., et al., "Human extracellular matrix (ECM) powders for injectable cell delivery and adipose tissue engineering," *J. Control Release*, 2009, vol. 139, pp. 2-7.

Discher, D.E., et al., "Tissue cells feel and respond to the stiffness of their substrate," *Science*, 2005, vol. 310, pp. 1139-1143.

Eitan, Y., et al., "Acellular cardiac extracellular matrix as a scaffold for tissue engineering: in vitro cell support, remodeling, and biocompatibility," *Tissue Eng. Part C: Methods*, 2010, vol. 16, pp. 671-683.

Engberg, N., et al., "Retinoic acid synthesis promotes development of neural progenitors from mouse embryonic stem cells by suppressing endogenous, Wnt-dependent nodal signaling," *Stem Cells*, 2010, vol. 28, pp. 1498-1509.

Farina, A., et al., "Temporal proteomic profiling of embryonic stem cell secretome during cardiac and neural differentiation," *Proteomics*, 2011, vol. 11, pp. 3972-3982.

Fok, E.Y., et al., "Shear-controlled single-step mouse embryonic stem cell expansion and embryoid body-based differentiation," *Stem Cells*, 2005, vol. 23, pp. 1333-1342.

Goncalves, M.B., et al., "Timing of the retinoid-signalling pathway determines the expression of neuronal markers in neural progenitor cells," *Dev. Biol.*, 2005, vol. 278, pp. 60-70.

Grayson, W.L., et al., "Human mesenchymal stem cells tissue development in 3D PET matrices," *Biotechnol. Prog.*, 2004, vol. 20, pp. 905-912.

Herget, T., et al., "Production of ceramides causes apoptosis during early neural differentiation in vitro," *J. Biol. Chem.*, 2000, vol. 275, pp. 30344-30354.

Hoganson, D.M., et al., "The retention of extracellular matrix proteins and angiogenic and mitogenic cytokines in a decellularized porcine dermis," *Biomaterials*, 2010, vol. 31, pp. 6730-6737.

Hughes, C., et al., "Mass Spectrometry-Based Proteomics Analysis of the Matrix Microenvironment in Pluripotent Stem Cell Culture," *Mol. Cell Proteomics*, 2012, vol. 11, pp. 1924-1936.

Hunt, G.C., et al., "Endogenous production of fibronectin is required for self-renewal of cultured mouse embryonic stem cells," *Exp. Cell Res.*, 2012, vol. 318, pp. 1820-1831.

Hynes, R.O., "The extracellular matrix: not just pretty fibrils," *Science*, 2009, vol. 326, pp. 1216-1219.

Jiang, T., et al., "Preparation and characterization of genipin-crosslinked rat acellular spinal cord scaffolds," *Mater. Sci. Eng. C: Mater. Biol. Appl.*, 2013, vol. 33, pp. 3514-3521.

Kennedy, K.A., et al., "Retinoic acid enhances skeletal muscle progenitor formation and bypasses inhibition by bone morphogenetic protein 4 but not dominant negative beta-catenin," *BMC Biol.*, 2009, vol. 7, pp. 67-87.

Keung, A.J., et al., "Soft microenvironments promote the early neurogenic differentiation but not self-renewal of human pluripotent stem cells," *Integr. Biol.*, 2012, vol. 4, pp. 1049-1058.

Keung, A.J., et al., "GTPases mediate the mechanosensitive lineage commitment of neural stem cells," *Stem Cells*, 2011, vol. 29, pp. 1886-1897.

Keung, A.J., et al., "Pan-neuronal maturation but not neuronal subtype differentiation of adult neural stem cells is mechanosensitive," *Sci. Rep.*, 2013, vol. 3, pp. 1817-1822.

Kim, J., et al., "Autocrine fibroblast growth factor 2-mediated interactions between human mesenchymal stem cells and the extracellular matrix under varying oxygen tension," *J. Cell. Biochem.*, 2012, vol. 114, pp. 716-727.

Kothapalli, C.R., et al., "3D matrix microenvironment for targeted differentiation of embryonic stem cells into neural and glial lineages," *Biomaterials*, 2013, vol. 34, pp. 5995-6007.

Kraushaar, D.C., et al., "Heparan sulfate facilitates FGF and BMP signaling to drive mesoderm differentiation of mouse embryonic stem cells," *J. Biol. Chem.*, 2012, vol. 287, pp. 22691-22700.

Krieg, M., et al., "Tensile forces govern germ-layer organization in zebrafish," *Nat. Cell Biol.*, 2008, vol. 10, pp. 429-436.

Lee, S.T., et al., "Engineering integrin signaling for promoting embryonic stem cell self-renewal in a precisely defined niche," *Biomaterials*, 2010, vol. 31, pp. 1219-1226.

Leipzig, N.D., et al., "The effect of substrate stiffness on adult neural stem cell behavior," *Biomaterials*, 2009, vol. 30, pp. 6867-6878.

Li, M., et al., "Generation of purified neural precursors from embryonic stem cells by lineage selection," *Curr. Biol.*, 1998, vol. 8, pp. 971-974.

Li, X., et al., "Fibroblast growth factor signaling and basement membrane assembly are connected during epithelial morphogenesis of the embryoid body," *J. Cell Biol.*, 2001, vol. 153, pp. 811-822.

Liang, H.C., et al., "Effects of crosslinking degree of an acellular biological tissue on its tissue regeneration pattern," *Biomaterials*, 2004, vol. 25, pp. 3541-3552.

Lichtenberg, A., et al., "In vitro re-endothelialization of detergent decellularized heart valves under simulated physiological dynamic conditions," *Biomaterials*, 2006, vol. 27, pp. 4221-4229.

Lock, L.T., et al., "Expansion and differentiation of human embryonic stem cells to endoderm progeny in a microcarrier stirred-suspension culture," *Tissue Eng. Part A*, 2009, vol. 15, pp. 2051-2063.

Lu, H., et al., "Autologous extracellular matrix scaffolds for tissue engineering," *Biomaterials*, 2011, vol. 32, pp. 2489-2499.

Lu, H., et al., "Comparison of decellularization techniques for preparation of extracellular matrix scaffolds derived from three-dimensional cell culture," *J. Biomed. Mater. Res. A*, 2012, vol. 100, pp. 2507-2516.

Maitre, J.L., et al., "Adhesion functions in cell sorting by mechanically coupling the cortices of adhering cells," *Science*, 2012, vol. 338, pp. 253-256.

Martino, G., et al., "Brain regeneration in physiology and pathology: the immune signature driving therapeutic plasticity of neural stem cells," *Physiol. Rev.*, 2011, vol. 91, pp. 1281-1304.

Matsuoka, Y., et al., "Insufficient folding of type IV collagen and formation of abnormal basement membrane-like structure in embryoid bodies derived from Hsp47-null embryonic stem cells," *Mol. Biol. Cell*, 2004, vol. 15, pp. 4467-4475.

Mereau, A., et al., "Characterization of a binding protein for leukemia inhibitory factor localized in extracellular matrix," *J. Cell Biol.*, 1993, vol. 122, pp. 713-719.

Micallef, S.J., et al., "Retinoic acid induces Pdx1-positive endoderm in differentiating mouse embryonic stem cells," *Diabetes*, 2005, vol. 54, pp. 301-305.

Nair, R., et al., "Gene Expression Signatures of Extracellular Matrix and Growth Factors during Embryonic Stem Cell Differentiation," *PLOS ONE*, 2012, vol. 7, No. 10, Doc. No. e42580.

(56) References Cited

OTHER PUBLICATIONS

Nair, R., et al., "Efficacy of solvent extraction methods for acellularization of embryoid bodies," *J. Biomater. Sci. Polym. Ed.*, 2008, vol. 19, pp. 801-819.
Nakayama, K.H., et al., "Decellularized rhesus monkey kidney as a three-dimensional scaffold for renal tissue engineering," *Tissue Eng. Part A*, 2010, vol. 16, pp. 2207-2216.
Ngangan, A.V., et al., "Acellularization of embryoid bodies via physical disruption methods," *Biomaterials*, 2009, vol. 30, pp. 1143-1149.
Nolte, A.J., et al., "Determining the Young's modulus of polyelectrolyte multilayer films via stress-Induced mechanical buckling instabilities," *Macromolecules*, 2005, 38, pp. 5367-5370.
Okada, Y., et al., "Retinoic-acid-concentration-dependent acquisition of neural cell identity during in vitro differentiation of mouse embryonic stem cells," *Dev. Biol.*, 2004, vol. 275, pp. 124-142.
Persaud, S.D., et al. "Cellular retinoic acid binding protein I mediates rapid non-canonical activation of ERK1/2 by all-trans retinoic acid," *Cell. Signal.*, 2012, vol. 25, pp. 19-25.
Postovit, L.M., et al., "Human embryonic stem cell microenvironment suppresses the tumorigenic phenotype of aggressive cancer cells," *Proc. Natl. Acad. Sci. USA*, 2008, vol. 105, No. 11, pp. 4329-4334.
Postovit, L.M., et al., "A three-dimensional model to study the epigenetic effects induced by the microenvironment of human embryonic stem cells," *Stem Cells*, 2006, vol. 24, pp. 501-505.
Przybyla, L., et al., "Probing embryonic stem cell autocrine and paracrine signaling using microfluidics," *Annu. Rev. Anal. Chem.*, 2012, vol. 5, pp. 293-315.
Rowland, J.W., et al., "Generation of neural stem cells from embryonic stem cells using the default mechanism: in vitro and in vivo characterization," *Stem Cells Dev.*, 2011, vol. 20, pp. 1829-8145.
Rozario, T., et al., "The extracellular matrix in development and morphogenesis: a dynamic view," Dev. Biol., 2010, vol. 341, pp. 126-140.
Sachlos, E., et al., "Embryoid body morphology influences diffusive transport of inductive biochemicals: a strategy for stem cell differentiation," *Biomaterials*, 2008, vol. 29, pp. 4471-4488.
Saha, K, et al., "Substrate modulus directs neural stem cell behavior," *Biophys. J.*, 2008, vol. 95, pp. 4426-4438.
Santos, T., et al., "Polymeric nanoparticles to control the differentiation of neural stem cells in the subventricular zone of the brain," *ACS Nano*, 2012, vol. 6, pp. 10463-10474.
Sart, S., et al., "Microenvironment regulation of pluripotent stem cell-derived neural progenitor aggregates by human mesenchymal stem cell secretome," Tissue Engineering Part A, 2014, vol. 20, pp. 2666-26679; abstract only.
Sart, S., et al., "Modulation of mesenchymal stem cell actin organization on conventional microcarriers for proliferation and differentiation in stirred bioreactors," *J. Tissue Eng. Regen. Med.*, 2013, vol. 7, pp. 537-551.
Sart, S., et al., "Cryopreservation of pluripotent stem cell aggregates in defined protein-free formulation," *Biotechnol. Prog.*, 2013, vol. 29, pp. 143-153.
Sart, S. et al. "Acellular matrices derived from PSC aggregates as bioactive scaffolds" presented at AIChE Annual Meeting, Pittsburgh, PA, Oct. 31, 2012.
Sart, S., et al., "Extracellular matrices decellularized from embryonic stem cells maintained their structure and signaling specificity," *Tissue Engineering Part A*, 2014, vol. 20, pp. 54-66.
Sharow, K.A., et al., "Retinoic acid stability in stem cell cultures," Int. J. Dev. Biol., 2012, vol. 56, pp. 273-278.
Simandi, Z., et al., "Activation of retinoic acid receptor signaling coordinates lineage commitment of spontaneously differentiating mouse embryonic stem cells in embryoid bodies," *FEBS Lett.*, 2010, vol. 584, pp. 3123-3130.
Stergiopoulos, A., "The role of nuclear receptors in controlling the fine balance between proliferation and differentiation of neural stem cells," *Arch. Biochem. Biophys.*, 2013, vol. 534, pp. 27-37.
Takahashi, K., et al., "Induction of pluripotent stem cells from adult human fibroblasts by defined factors," *Cell*, 2007, vol. 131, 861-872.
Thomson, J.A., et al., "Embryonic stem cell lines derived from human blastocysts," *Science*, 1998, vol. 282, 1145-1147.
Tropepe, V., et al., "Direct neural fate specification from embryonic stem cells: a primitive mammalian neural stem cell stage acquired through a default mechanism," *Neuron*, 2001, vol. 30, pp. 65-78.
Turner, A.E., et al., "Design and characterization of tissue-specific extracellular matrix-derived microcarriers," *Tissue Eng. Part C: Methods*, 2012, vol. 18, 186-197.
Turner, A.E., et al., "The performance of decellularized adipose tissue microcarriers as an inductive substrate for human adipose-derived stem cells," *Biomaterials*, 2012, vol. 33, pp. 4490-4499.
Ulloa, L., et al., "Lefty inhibits receptor-regulated Smad phosphorylation induced by the activated transforming growth factor-beta receptor," *J. Biol. Chem.*, 2001, vol. 276, pp. 21397-21404.
Xu, C., et al., "Feeder-free growth of undifferentiated human embryonic stem cells," *Nat. Biotechnol.*, 2001, vol. 19, pp. 971-974.
Yan, L.P., et al., "Genipin-cross-linked collagen/chitosan biomimetic scaffolds for articular cartilage tissue engineering applications," *J. Biomed. Mater. Res. A*, 2010, vol. 95, pp. 465-475.
Youngstrom, D.W., et al., "Functional characterization of detergent-decellularized equine tendon extracellular matrix for tissue engineering applications," PLOS ONE, 2013, vol. 8, No. 5, Doc. No. e64151.
Yu, S., et al., "Retinoic acid induces neurogenesis by activating both retinoic acid receptors (RARs) and peroxisome proliferator-activated receptor beta/delta (PPARbeta/delta)," *J. Biol. Chem.*, 2012, vol. 287, pp. 42195-42205.
Yu, J., et al., "Induced pluripotent stem cell lines derived from human somatic cells," *Science*, 2007, vol. 318, pp. 1917-1920.
Zang, M., et al., "Decellularized tracheal matrix scaffold for tissue engineering," *Plast. Reconstr. Surg.*, 2012, vol. 130, pp. 532-540.
Zhang, P., et al., "Short-term BMP-4 treatment initiates mesoderm induction in human embryonic stem cells," *Blood*, 2008, vol. 111, pp. 1933-1941.
Zweigerdt, R., et al., "Scalable expansion of human pluripotent stem cells in suspension culture," *Nat. Protoc.*, 2011, vol. 6, pp. 689-700.

\* cited by examiner

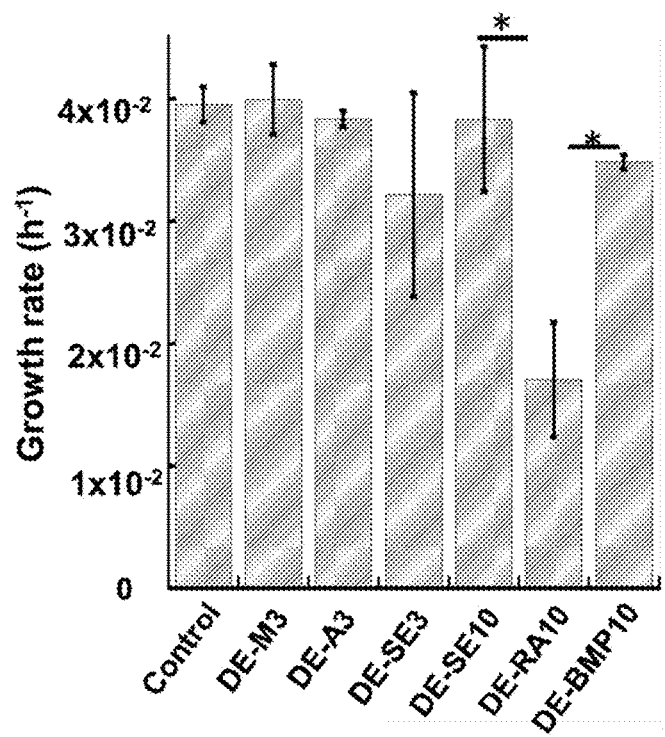
FIG. 6A
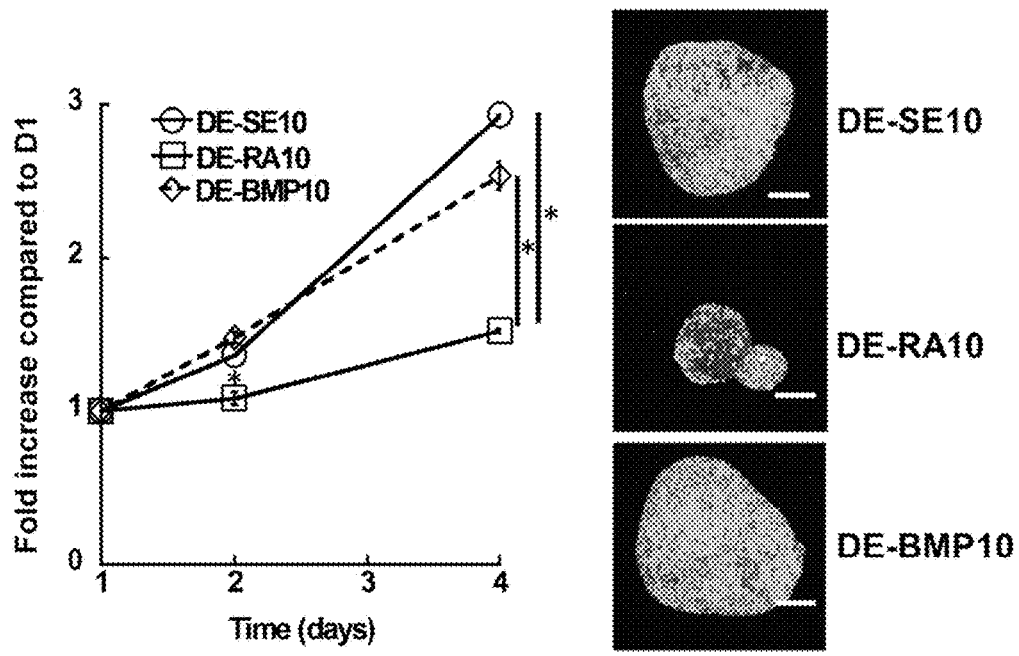
FIG. 6B
FIG. 6C

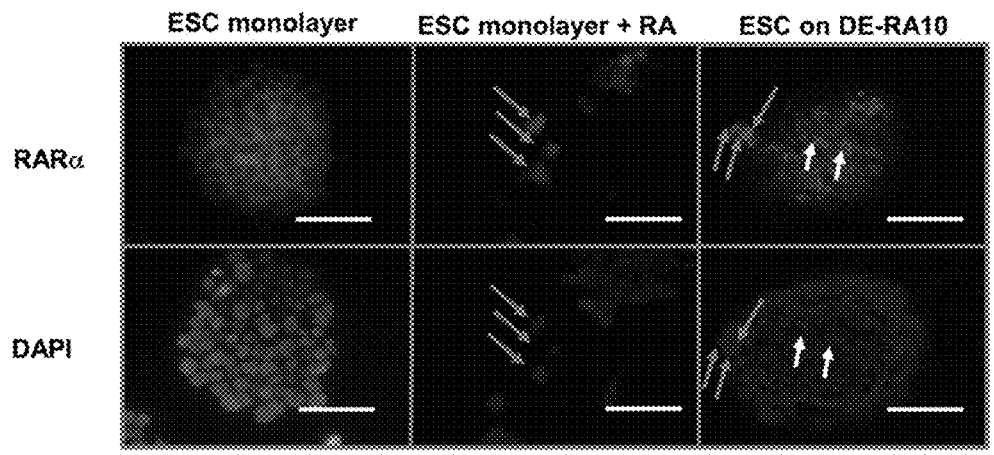
FIG. 8A
| | Growth rate (×10⁻² h⁻¹) | Oct-4 positive (%) |
|---|---|---|
| DE-RA10 | 0.9 ± 0.1 | 61.0 ± 1.2 |
| Soluble RA | -1.3 ± 0.3 | 10.1 ± 1.4 |
FIG. 8B
| | Growth rate (×10⁻² h⁻¹) | Oct-4 positive (%) |
|---|---|---|
| - BMS 493 | 0.4 ± 0.1 | 51.6 ± 0.2 |
| + BMS 493 | -1.7 ± 0.1 | 59.1 ± 3.3 |
FIG. 8C
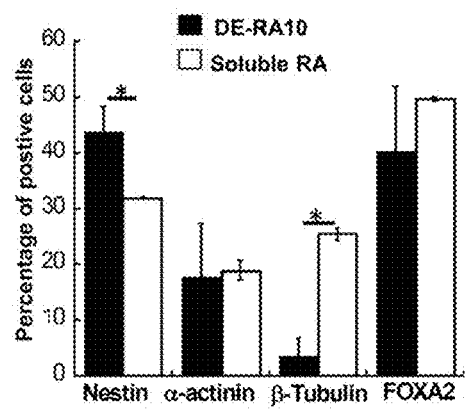
FIG. 8D
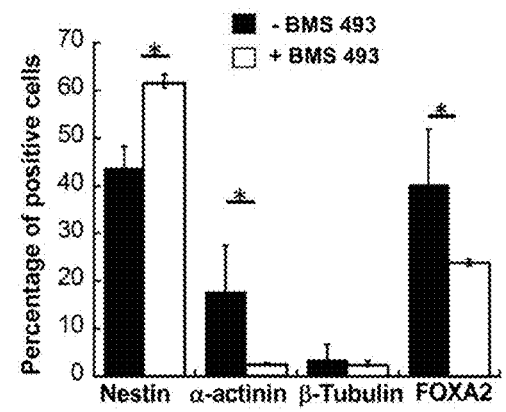
FIG. 8E

EXTRACELLULAR MATRIX DERIVED FROM STEM CELLS AND METHODS FOR PRODUCTION

CROSS-REFERENCE TO RELATED APPLICATIONS

The present application is the National Stage of International Application Number PCT/US2014/011518, filed Jan. 14, 2014, which claims the benefit of U.S. Provisional Application Ser. No. 61/752,205, filed Jan. 14, 2013, which is hereby incorporated by reference herein in its entirety, including any figures, tables, nucleic acid sequences, amino acid sequences, or drawings.

GOVERNMENT SUPPORT

This invention was made with government support under grant number 1342192 awarded by the National Science Foundation. The government has certain rights in the invention.

BACKGROUND OF THE INVENTION

Pluripotent stem cells (PSCs), including embryonic stem cells (ESCs) and induced pluripotent stem cells (iPSCs), have significant potential in tissue engineering and regenerative medicine due to the unlimited self-renewal ability and the capacity to differentiate into three-germ layers (1-3). In addition to PSCs' intrinsic properties, the extracellular PSC microenvironment comprising extracellular matrix (ECM) proteins as well as growth factors/cytokines also plays important roles in PSC development and function. In vivo, embryonic development is accompanied by the coordinated synthesis and secretion of ECM proteins, which are known to direct cell growth, survival, differentiation and morphogenesis (4,5). In vitro, cultured PSCs produce endogenous ECM proteins (i.e., fibronectin, basement membrane proteins) that regulate PSC fate through cell adhesion and/or binding with autocrine factors (i.e., leukemia inhibitory factor (LIF), Wnt, and Activin) (6-9). Thus, the derivation of ECMs from PSC cultures while preserving their distinct signaling capacities will greatly enhance their potential in cell delivery and tissue repair (10,11).

Stem cell-derived ECMs have been used to support in vitro cell expansion and differentiation as well as in vivo tissue regeneration (12-14). Tissue-specific ECMs derived from mesenchymal stem cells (MSCs) directed MSC lineage specification and augmented tissue regeneration by extending site-specific MSC retention (13-17). In addition, microcarriers made from MSC-derived ECMs promoted MSC adipogenesis and demonstrated in vivo compatibility, indicating the feasibility of their use in large scale cell production and cell/matrix delivery (14,15,18,19). The ECMs decellularized from ESC cultures provided a permissive microenvironment for tissue remodeling and fibroblast repopulation (11,12). The decellularized ESCs grown on Matrigel have also been shown to recapitulate the cellular and molecular milieu of the embryonic microenvironment and to sustain a balance between self-renewal and differentiation, preventing aberrant cell proliferation such as the aggressive cancer cells (20,21). Compared to the ECMs derived from adult stem cells or somatic tissues, the decellularized matrices from PSCs may have a broader spectrum of signaling capacity owing to their embryonic origin (6,10). The PSC-derived ECMs are free of embryonic DNA and thus have reduced risk of tumor formation, significantly improving their prospects in clinical applications.

In vitro, PSCs have been grown as undifferentiated monolayers or 3-D aggregates for expansion, or as embryoid bodies (EBs) differentiated into specific lineages (22-25). These organizations have been shown to affect the secretion of ECM proteins and autocrine factors, producing ECM microenvironment of distinct characteristics (20,26,27). For example, deposition of endogenous transforming growth factor-beta (TGF-β) inhibitor, Lefty, into ECMs has been reported for undifferentiated ESCs but not EBs, whereas the EBs displayed unique ECM-shell structure and different cytokine secretion profiles compared to undifferentiated ESCs (20,28-30). PSCs expanded as aggregates up-regulated E-cadherin expression and down-regulated Wnt signaling upon differentiation compared to PSCs cultured on 2-D substrate, suggesting the impact of intercellular interactions on cell signaling (26). Parallel to the organizational dependence, the characteristics of PSC-derived ECMs are also influenced by lineage specifications (6,23,29). For example, cerberus, a small antagonist of bone morphogenic protein (BMP), was detected in the secretome and ECMs of ESCs undergoing cardiac differentiation but not neural differentiation (6,28). Finally, the ECMs derived at the primitive or definitive stage of EBs exhibited different signaling capacities, suggesting the influence of developmental stage on ECM characteristics (10,11,28).

BRIEF SUMMARY OF THE INVENTION

The subject invention concerns acellular extracellular matrix (ECM) that can recapitulate developmental cues and can provide for specific biological properties. The subject invention also concerns methods for preparing acellular ECM of the invention. In one embodiment, the ECM is prepared from 3-D aggregates of pluripotent stem cells or from embryoid bodies. The stem cells used in the present invention can be embryonic stem cells (ESC). In a specific embodiment, the stem cells or embryoid bodies are from human. The ECM of the invention can be mass produced using PSC aggregates or embryoid bodies in large scale bioreactors. In one embodiment, the ECM is in the form of acellular microspheres. The acellular ECM produced using the present invention can be used for injection into a person or animal.

In one embodiment, a method of the invention comprises growing stem cells in suspension culture as aggregates, e.g., in a bioreactor. Cells are allowed to grow for a suitable time period to allow for production of ECM. In one embodiment, cells are grown for 1-3 days. In another embodiment, cells are grown from 4-10 or more days. Optionally, the cells can be grown in the presence of one or more cytokines and/or growth factors, such as leukemia inhibitory factor (LIF), RA or BMP-4, in a differentiation medium. Acellular ECM is then prepared from the cell aggregates by decellularization. In a specific embodiment, a decellularization reagent comprising a detergent, such as Triton X-100, is used, followed by treatment with a DNase. In an exemplified embodiment, the decellularization step comprises treatment with 1% Triton X-100 for about 30 minutes and DNase I treatment for about 30 minutes. Optionally, treated samples can be washed (e.g., in PBS) one or more times after each treatment step. The decellularization process of the present invention preserves proteins of the ECM produced by the cells. An acellular ECM of the invention can comprise proteins such as fibronectin (FN), laminin (LN), collagen type IV (Col IV), vitronectin (VN), and glycosaminoglycans (GAGs). In certain embodiments, acellular ECM of the invention can be reseeded with stem cells and support proliferation thereof.

The subject invention also concerns an ECM of the present invention reseeded with cells such as PSC or ESC. In certain embodiments, reseeded ECM of the invention support can support cell proliferation in vitro or in vivo. ECM of the invention prepared from cells or EB exposed to RA during culture decrease proliferation of reseeded ESC. The ECM can be prepared so as to promote differentiation of reseeded cells into specific germ layer lineages, i.e., ectoderm, endoderm, and/or mesoderm. For example, ECM derived from RA treated EBs promotes differentiation of cells towards ectodermal, endodermal and mesodermal lineages, whereas ECM derived from long-term EBs promote differentiation towards endodermal and mesodermal lineages.

The present invention evaluated the influence of ESC organizations (i.e., undifferentiated monolayers, undifferentiated 3-D aggregates, and differentiated EBs) and lineage commitment on the characteristics of the decellularized ECMs. The ECMs at the primitive and definitive stage of EB differentiation were also derived from day 3 or day 10 EBs, respectively (23,28). To create the ECMs with lineage-specific cues, EBs were treated with retinoic acid (RA) for neural development or BMP-4 for mesoderm differentiation (31,32). To probe the role of RA signaling in the characteristics of decellularized ECMs, the cellular expression of RA receptor (RAR) and the effect of a pan-RAR antagonist were investigated. The results show that the decellularized matrices derived from ESCs are able to recapitulate the developmental cues and have distinct capacity in directing ESC fate.

BRIEF DESCRIPTION OF THE DRAWINGS

(FIG. 2A) Expression of residual DNA. (FIG. 2B) Quantitative immunocytochemistry of different ECM proteins including fibronectin (FN), laminin (LN), collagen IV (Col IV), and vitronectin (VN). * p-value<0.05.

(FIG. 3A) SEM images of surface morphology of native and acellular EBs. (FIG. 3B) Topography and roughness (Ra) of acellular ECMs assessed by AFM. (FIG. 3C) Expression of ECM proteins pre- and post-decellularization: confocal images of FN, LN, Col IV, and VN expression, and light images of glycosaminoglycans (GAGs) from EB samples. Scale bar: 100 µm. For native Col IV, scale bar: 50 µm.

(FIG. 4A) ECM expression for the ESC monolayer cultures at days 1 and 3. (FIG. 4B) ECM expression for the ESC aggregates at days 1 and 3. (FIG. 4C) Comparison of ECM expression pre- and post-decellularization after 3 days of monolayer culture (DE-M3). (FIG. 4D) Comparison of ECM expression pre- and post-decellularization after 3 days of aggregate culture (DE-A3). * p-value<0.05.

(FIG. 5A) ECM expression in the EBs at days 3 and 10. (FIG. 5B) ECM expression pre- and post-decellularization of day 3 and day 10 EBs (DE-SE3 and DE-SE10, respectively). (FIG. 5C) Comparison of decellularized ECM expression for EBs treated by BMP-4 (DE-BMP) or RA (DE-RA) with spontaneously differentiated EBs (DE-SE). (FIG. 5D) Proportion of FN, LN, Col IV, and VN in different decellularized ECM scaffolds. * p-value<0.05.

FIGS. 6A-6E. Proliferation and Oct-4 expression of the reseeded ESCs on the decellularized ECM scaffolds. (FIG. 6A) Specific growth rate of ESCs reseeded on control (gelatin) and different decellularized ECM scaffolds. (FIG. 6B) Representative cell viability of reseeded ESCs determined by MTT assay. (FIG. 6C) Representative confocal images of BrdU expression in reseeded ESCs. Scale bar: 50 µm. (FIG. 6D) Oct-4 expression of ESCs reseeded on control (gelatin) and different decellularized ECM scaffolds. (FIG. 6E) Representative flow cytometry histograms of Oct-4 expression of reseeded ESCs. * p-value<0.05.

FIGS. 8A-8E. Role of RA-RAR interactions in ESCs cultured on the decellularized ECM scaffolds. (FIG. 8A) Localization of RAR-α in ESC monolayers with or without RA treatment (Scale bar: 50 µm), and the confocal images of RAR-α in reseeded ESCs on the DE-RA10 (Scale bar: 100 µm). Long arrow: RAR-α expression in cell nucleus; short arrow: RAR-α expression in cytoplasm. (FIG. 8B) Specific growth rate and Oct-4 expression for the cells grown in the DE-RA10 or the cells grown in the DE-SE10 treated with soluble RA. (FIG. 8C) Specific growth rate and Oct-4 expression for cells grown in the DE-RA10 with or without BMS 493 treatment. (FIG. 8D) Expression of three-germ layer markers for ESCs seeded on the DE-RA10 versus ESCs treated by soluble RA. (FIG. 8E) Expression of three-germ layer markers for ESCs seeded on the DE-RA10 with or without BMS 493 treatment. * p-value<0.05.

(FIG. 11A) Ultrastructure of DE-NC and DE-NG assessed by SEM. (FIG. 11B) Representative AFM images of surface roughness for DE-NC, DE-NG, and DE-NGL; (FIG. 11C) Representative AFM images of Young's modulus for DE-NC, DE-NG, and DE-NGL; Quantification of surface roughness (FIG. 11D) and Young's modulus (FIG. 11E) of DE-NC, DE-NG and DE-NGL.

(FIG. 12A) Representative morphology of the ECM scaffolds upon collagenase treatment. Scale bar: 100 μm. (FIG. 12B) Quantification of the percentage of remaining proteins from DE-NC, DE-NG, and DE-NGL after collagenase treatment. * p-value<0.05.

(FIG. 13A) Representative imaged of reseeded NPCs (stained with calcein AM to show live cells) on the decellularized scaffolds. Long arrows point non-crosslinked ECM scaffolds. Short arrows indicated the crosslinked ECM scaffolds displaying red auto fluorescence. (FIG. 13B) Percentage of colonization on non-crosslinked control and genipin-crosslinked scaffolds. (FIG. 13C) Size distribution of NPC aggregates and ECM scaffolds interacting with NPCs. Scale bar: 100 μm. *p-value<0.05.

(FIG. 14A) Fold increase in cell number at day 3 after reseeding; (FIG. 14B) MTT activity for NPCs reseeded on DE-A and DE-E scaffolds; (FIG. 14C) MTT activity for dissociated and intact NPCs reseeded on DE-NC, DE-NG and DE-NGL. (FIG. 14D) Viability of intact NPCs reseeded on decellularized ECM scaffolds. * p-value<0.05.

(FIG. 15C) Percentage of cells positive for Nestin. (FIG. 15D) Percentage of cells positive for Musashi-1 (FIG. 15D). Scale bar: 100 μm. * p-value<0.05.

(FIG. 16C) Percentage of cells positive for β-tubulin III. (FIG. 16D) Percentage of cells positive for GFAP (FIG. 16D). Scale bar: 100 μm. * p-value<0.05.

(FIG. 17A) Fold change in the proliferation of the reseeded ESC-NPCs after BMS 493 treatment (+BMS) compared to untreated cultures (−BMS). (FIG. 17B) Fold change in the expression of Nestin, (FIG. 17C) fold change in the expression of β-tubulin III, and (FIG. 17D) fold change in the expression of GFAP after BMS 493 treatment (+BMS) compared to untreated cultures (−BMS). * p-value<0.05.

DETAILED DESCRIPTION OF THE INVENTION

Figure 1:
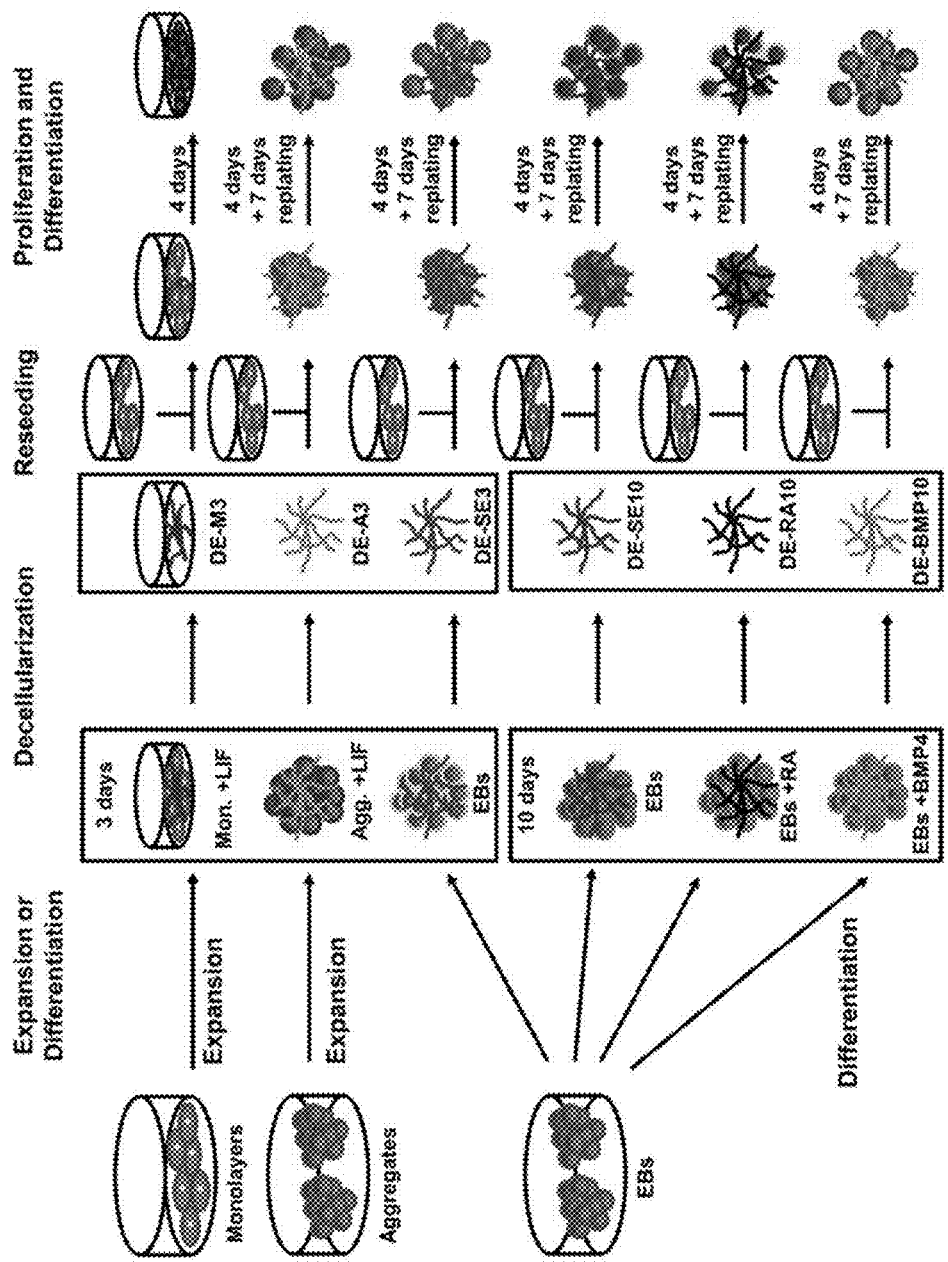
FIG. 1. Schematic diagram of the experimental procedure. ESCs were seeded as monolayer, aggregates, or EBs for 3 to 10 days. The monolayers, aggregates, or EBs were decellularized, and ESCs were reseeded on the ECM scaffolds for 4 days without LIF as short-term expansion. The cells were replated and grew for 7 days in the absence of inducing growth factors for differentiation. Decellularization was also performed for EBs treated with BMP-4 or RA.

The subject invention concerns acellular extracellular matrix (ECM) that can recapitulate developmental cues and can provide for specific biological properties. The subject invention also concerns methods for preparing acellular ECM of the invention. In one embodiment, the ECM is prepared from 3-D aggregates or from embryoid bodies (EB) of pluripotent stem cells (PSC). The stem cells used in the present invention can be embryonic stem cells (ESC). In a specific embodiment, the cells or EB are from human or another mammal. The ECM of the invention can be mass produced using PSC aggregates or embryoid bodies in large scale bioreactors. In one embodiment, the ECM is in the form of acellular microspheres. Optionally, acellular ECM can be cross-linked to increase stability and/or stiffness. In one embodiment, acellular ECM is cross-linked using genipin (methyl (1R,2R,6S)-2-hydroxy-9-(hydroxymethyl)-3-oxabicyclo[4.3.0]nona-4,8-diene-5-carboxylate). The acellular ECM produced using the present invention can be used for injection into a person or animal to provide for tissue engineering, regeneration of tissue or an organ, wound healing, and/or for treatment of a disease or condition, such as cancer.

In one embodiment, a method for preparing ECM of the invention comprises growing stem cells in suspension culture as aggregates or as embryoid bodies, e.g., in a bioreactor. Cells are allowed to grow for a suitable time period to allow for production of an ECM. In one embodiment, cells are grown for 1-3 days. In another embodiment, cells are grown from 4-10 or more days. Optionally, the cells can be grown in a medium that inhibits or induces differentiation, e.g., containing one or more cytokines and/or growth factors, such as leukemia inhibitory factor (LIF), retinoic acid (RA) or a bone morphogenic protein (e.g., BMP-4). Acellular ECM is then prepared from the cell aggregates or embryoid bodies by decellularization. In a specific embodiment, a decellularization reagent comprising a surfactant or detergent, such as Triton X-100 (octylphenol ethoxylate surfactant), is used, followed by treatment with a nuclease, such as a DNase or a micrococcal nuclease. Treatment time can range from a few minutes to hours. In one embodiment, treatment time can range from about 15 minutes up to about 60 minutes for each of the surfactant/detergent and the nuclease. In another embodiment, treatment time can range from about 15 minutes up to about 45 minutes for each of the surfactant/detergent and the nuclease. In an exemplified embodiment, the decellularization step comprises treatment with 1% Triton X-100 for about 30 minutes and DNase I treatment for about 30 minutes. In a further embodiment, a decellularization reagent comprises sodium dodecyl sulfate (SDS) (e.g., 1% SDS) followed by treatment with a nuclease. Optionally, treated samples can be washed (e.g., in PBS) one or more times after each treatment step. Optionally, acellular ECM can be cross-linked to increase stability and/or stiffness. In one embodiment, acellular ECM is cross-linked using genipin (methyl (1R,2R,6S)-2-hydroxy-9-(hydroxymethyl)-3-oxabicyclo[4.3.0]nona-4,8-diene-5-carboxylate). In a specific embodiment, about 3% genipin is used and ECM are incubated with genipin for several hours, e.g., 3 to 9 hours, or 5 to 7 hours, or about 6 hours. ECM produced by the method can be isolated or purified using standard methods, e.g., centrifugation. The decellularization process of the present invention preserves proteins of the ECM produced by the cells. An acellular ECM of the invention can comprise proteins such as fibronectin (FN), laminin (LN), collagen type IV (Col IV), vitronectin (VN), and/or glycosaminoglycans (GAGs). Acellular ECM of the invention can be reseeded with cell, such as stem cells, and support proliferation and/or differentiation thereof. In one embodiment, the reseeded cells comprise neural progenitor cells.

The subject invention also concerns an ECM of the present invention reseeded with cells such as PSC or ESC. In certain embodiments, reseeded ECM of the invention can support cell proliferation in vitro or in vivo. In one embodiment, ECM of the invention prepared from cells or EB exposed to RA during culture decrease proliferation of reseeded ESC. The ECM can be prepared so as to promote differentiation of reseeded cells into specific germ layer lineages, i.e., ectoderm, endoderm, and/or mesoderm. For example, ECM derived from RA treated EBs promotes differentiation of cells towards ectodermal, endodermal and mesodermal lineages, whereas ECM derived from long-term EBs promote differentiation towards endodermal and mesodermal lineages.

The subject invention also concerns compositions comprising an acellular ECM or a cell reseeded ECM produced according to the present invention. In one embodiment, the composition can comprise a physiologically acceptable carrier, buffer, or diluent. The methods of the subject invention may also be practiced by administering compositions to a patient. The compositions can comprise at least one active ingredient in one or more physiologically acceptable carriers. A carrier can be acceptable in the sense of being compatible with the other ingredients of the formulation and not injurious to the patient. In some embodiments, ECM of the invention can be provided in a composition in a lyophilized form. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the ECM is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically acceptable carriers and diluents which are known to those skilled in the art. Examples of carriers or diluents for use with the subject invention include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the ECM of the invention can also comprise suspension agents, protectants, lubricants, buffers, preservatives, and stabilizers. ECM compositions of the invention can also comprise one or more cell growth or differentiation factors, cytokines, and/or bioactive components, such as antibiotics, antibacterial compounds, antifungal compounds, antiparasitic compounds, antiviral compounds, anti-inflammatory compounds, wound healing compounds, neurotrophic compounds, angiogenic compounds, proteins (e.g., various types of collagen, fibronectin, etc.), etc.

The subject invention also concerns methods for in vitro growing and large scale production of stem cells and derivatives thereof. Acellular ECM of the present invention can be seeded with cells and cultured in a suitable culture medium. Culture medium can be replaced with fresh culture medium as needed. In one embodiment, the culture medium comprises LIF. After a suitable time period, cells can be collected and harvested from the culture. In one embodiment, cells can be harvested by contact with trypsin. The methods of the invention can be used with various in vitro cell culture systems including, but not limited to, a bioreactor, spinner flasks, microgravity bioreactors, and fluidized bed bioreactors. Acellular ECM of the invention can be provided in the form of microspheres.

The subject invention also concerns methods for cell delivery and tissue repair or replacement in a person or animal by administering or implanting an acellular ECM or a cell-reseeded ECM of the present invention, or a composition comprising the same, to the person or animal. Cells and tissue contemplated for repair or replacement using the invention include, but are not limited to, skin, blood vessels, pancreas, muscle, liver, bone, lung, cardiac, cartilage, trachea, central nervous system (CNS) including brain, and peripheral nervous system (PNS). In one embodiment, the person or animal has neural tissue damage or loss, e.g., spinal cord injury. If the ECM is to be administered to a person, then preferably the ECM was produced using human cells or EB. In one embodiment, the ECM is administered to or implanted in the person or animal by injection. In a specific embodiment, an ECM is provided in the form of acellular microspheres. In another embodiment, the ECM is administered or implanted by way of surgical intervention on the person or animal. In another embodiment, cell-reseeded ECM is administered to or implanted in the person or animal. In one embodiment, the reseeded cells are PSC or ESC. The reseeded cells can be stem cells such as hematopoietic stem cells, mesenchymal stem cells, neural stem cells, etc. In one embodiment, cells comprise neural progenitor cells. Cells can also be mature, differentiated cells. Reseeded cells can be autologous, allogeneic, syngeneic, or xenogeneic to the person or animal in which they are to be implanted. The cells can be genetically modified or non-genetically modified. As will be understood by one of skill in the art, there are over 200 cell types in the human body. The methods and compositions of the present invention may utilize any of these cell types, singly or in combination. Other cells suitable for use with the compositions and methods of the present invention include those disclosed by Spier R. E. et al., eds., *The Encyclopedia of Cell Technology* (2000), John Wiley & Sons, Inc., and Alberts B. et al., eds., *Molecular Biology of the Cell* (1994), $3^{rd}$ ed., Garland Publishing, Inc., e.g., pages 1188-1189, which are incorporated herein by reference in their entireties. An ECM used in the methods can be prepared so as to recapitulate specific developmental cues and biological properties suitable for the cells to be delivered and/or the tissue to be repaired. The ECM or cell-reseeded ECM can be administered to the person or animal in or near an area in need of tissue repair or replacement. For example, if bone repair is needed, the ECM or cell-reseeded ECM can be administered in or near the area of bone to be repaired. In one embodiment, the ECM is delivered into neural tissue of the person or animal, e.g., by injection at a site of injury or damage. In one embodiment, ECM of the invention can be utilized that favors neuronal differentiation over glial. In one embodiment, the ECM or cell-reseeded ECM can be applied or implanted so that it directly contacts existing tissue adjacent to, or defining, the site of tissue damage or a defect or discontinuity, or it can directly contact another implant, or both. As noted herein, the ECM can be cross-linked to provide for varying degrees of stability and/or stiffness.

The subject invention also concerns methods for treating an oncological disorder such as cancer in a person or animal by administering an acellular ECM of the invention, or a composition comprising the ECM, that has been prepared with developmental cues that will inhibit proliferation of cells. In one embodiment, the ECM is prepared from aggregate cells or EB exposed to RA during cell culture. The ECM can be injected into a person or animal, e.g., at or near a site of a cancer. In one embodiment, abnormal ECM associated with an oncological disorder is treated with ECM prepared according to the present invention. Cancers contemplated for treatment include, but are not limited to, breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. Other non-limiting examples of cancers are carcinomas, e.g., basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; leukemia; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. In one embodiment, the cancer to be treated is a brain cancer (e.g., a glioblastoma).

In one embodiment, an acellular ECM of the invention is provided in the three-dimensional shape of a bone or tissue or a portion of a bone or tissue. For example, the ECM can be provided in the shape of a femur, a tibia, a fibula, a humerus, a radius, an ulna, a patella, a cranial bone, a maxillofacial bone, a spinal bone, a scapula, a clavicle, a carpal or metacarpal bone, a tarsal or metatarsal bone, or a pelvic bone, or any other bone in an animal body. The ECM can also be provided in the shape of a tissue or organ, such as heart, lung, liver, skin, muscle, etc. In one embodiment, an acellular ECM of the invention is molded into a specific desired form (e.g., by centrifugation of a flowable ECM within a mold) and the ECM material then dried (e.g., freeze drying). Alternatively, ECM of the invention may be cut into specific shapes and/or sizes. Optionally, the acellular ECM of the invention, whether provided in a specific three-dimensional shape or not, can be crosslinked (e.g., to enhance strength of the material). Methods and materials for crosslinking, such as photo-crosslinking techniques and chemical crosslinking agents (e.g., aldehydes, diimides, polyisocyanates, etc.) are known in the art. In a specific embodiment, an acellular ECM of the invention is crosslinked using genipin. An acellular ECM of the invention can also be provided in a compressed form. For example, a dried ECM of the invention may be compressed in one or more dimensions. An acellular ECM of the invention can also be provided in a sterilized or disinfected form. Materials and methods for sterilization and/or disinfection (e.g., irradiation, chemical agents, etc.) are known in the art. An acellular ECM of the invention can also be modified to include biological components such as growth factors (e.g., epidermal growth factor, fibroblast growth factor, etc.) and other bioactive components (e.g., antimicrobial agents, anti-inflammatory agents, etc.). A shaped 3-D ECM prepared according to the present invention can also be provided seeded with appropriate cells for use in tissue repair and treatment, including PSC and ESC. In one embodiment, the cells comprise neural progenitor cells (NPC).

The methods and compositions of the present invention can be used in the treatment of humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

The subject invention also concerns articles of manufacture and kits comprising one or more containers and one or more acellular ECM that are prepared using the methods of the present invention. Articles of manufacture and kits can optionally comprise instructions or labeling that describes how to maintain, store, and/or use the acellular ECM of the invention. Articles of manufacture and kits can also optionally comprise media for storage, maintenance, and/or use of the acellular ECM of the invention. In one embodiment, articles of manufacture and a kit of the invention comprises a syringe suitable for injection of an ECM into a human or other animal. In one embodiment, to ECM is provided in a freeze-dried or lyophilized form.

Materials and Methods for Examples 1-6

Undifferentiated ESC Culture

Monolayer culture: Murine ES-D3 line (American Type Culture Collection, Manassas, Va.) was maintained on 0.1% gelatin-coated 6-well culture plates (Millipore, Temecula, Calif.) in a standard 5% $CO_2$ incubator. The expansion medium consists of Dulbecco's Modified Eagle's medium (DMEM, Invitrogen, Carlsbad, Calif.) supplemented with 10% ESC-screened fetal bovine serum (FBS, Hyclone, Logan, Utah), 1 mM sodium pyruvate, 0.1 mM β-mercaptoethanol, penicillin (100 U/mL), streptomycin (100 μg/mL) (all from Invitrogen), and 1000 U/mL leukemia inhibitory factor (LIF) (Millipore). The cells were seeded at $2-4\times10^4$ cells/$cm^2$ and sub-cultured every 2-3 days.

Aggregate culture: The aggregates of ES-D3 cells were obtained by seeding the cells from ESC monolayer into Ultra-Low Attachment (ULA) 6-well plates (Corning Incorporated, Corning, NY) at a seeding density of $2-4\times10^4$ cells/$cm^2$ in 3 mL growth media (33). The aggregates were sub-cultured every 2-4 days and serially passaged for 5-15 passages. For passaging, the aggregates were trypsinized with 0.05% trypsin-EDTA for 5 min at 37° C., neutralized with the media containing FBS, and resuspended in the fresh media.

Differentiated EB Culture

For EB formation, $1\times10^6$ cells were seeded in the ULA 6-well plates. Three types of EBs were cultivated in differentiation medium for up to 10 days: 1) spontaneous differentiated EBs; 2) EBs treated with 1 μM all-trans RA (Sigma-Aldrich, St. Louis, Mich.); 3) EBs treated with 5 ng/mL BMP-4 (R&D systems, Minneapolis, Minn.). The differentiation medium consists of DMEM supplemented with 10% FBS, 0.1 mM β-mercaptoethanol, penicillin (100 U/mL), and streptomycin (100 ug/mL).

Derivation of Decellularized ECMs from Monolayers, Aggregates, and EBs

Four decellularization reagents, including 1) 1% Triton X-100, 2) 20 mM $NH_4OH$, 3)

1% SDS, and 4) 1% Triton X-100+20 mM NH$_4$OH (all from Sigma), were tested and compared (Table 1) (34,35). Briefly, about 600-1000 EBs were distributed into each of 1.5 mL microcentrifuge tubes and treated with different decellularization solutions for 30 min. After the treatment, the samples were spun down at 18,000 g for 2 min, rinsed twice with phosphate buffered saline (PBS), and incubated with 2,000 unit/mL DNAse I for 15-30 min. The samples were centrifuged at 18,000 g for 2 min and rinsed twice with PBS prior to characterization or cell reseeding.

Based on the residual DNA and the preservation of ECM structure, 1% Triton X-100 and 30 min DNase I treatment was selected and used to obtain different decellularized ECMs (DE) from monolayers, aggregates, and EBs (Table 2). The monolayers were decellularized similarly to aggregates but centrifugation steps were omitted. For undifferentiated ESCs, DEs were obtained from day 3 cultures only because the prolonged culture induces differentiation. For EBs, DEs were obtained after culturing for 3 days or 10 days.

TABLE 1

Comparison of various decellularization methods used in this study.

| Cond. | Reagents | DNAse I treatment | DNA removal | ECM preservation | Gross appearance |
|---|---|---|---|---|---|
| #1 | 1% Triton X-100 | 15 min | + | +++ | +++ |
| #2 | 1% Triton X-100 | 30 min | ++ | +++ | +++ |
| #3 | 20 mM NH$_4$OH | 15 min | − | ND* | +++ |
| #4 | 1% SDS | 15 min | +++ | +++ | − |
| #5 | 1% Triton X-100 + 20 mM NH$_4$OH | 15 min | ++ | ++ | +++ |

*Not determined

TABLE 2

A list of decellularized ECMs derived from ESCs grown in different conditions.

| Abbreviation | ESC growth condition | Culture duration | Growth factor treatment | Reseeding |
|---|---|---|---|---|
| DE-M3 | Undifferentiated monolayer | 3 days | LIF | Yes |
| DE-A3 | Undifferentiated aggregate | 3 days | LIF | Yes |
| DE-SE3 | Spontaneously differentiated EB | 3 days | None | Yes |
| DE-SE10 | Spontaneously differentiated EB | 10 days | None | Yes |
| DE-RA3 | Lineage-specific EB | 3 days | RA | No* |
| DE-RA10 | Lineage-specific EB | 10 days | RA | Yes |
| DE-BMP3 | Lineage-specific EB | 3 days | BMP-4 | No* |
| DE-BMP10 | Lineage-specific EB | 10 days | BMP-4 | Yes |

*Reseeding was not performed because of the small difference in ECM expression compared to DE-SE. Instead, day 10 samples were reseeded for the comparison with DE-SE scaffolds.

DNA Assay

The residual DNA after decellularization was measured using a DNA assay (36). A DNA standard was prepared by dissolving salmon testes DNA in TEX (10 mM Tris, 1 mM EDTA, 0.1% Triton X-100 at pH 8) and a standard curve was constructed for each assay. The decellularized samples were lysed with 0.1 mg/ml proteinase K (Fisher Scientific, Pittsburgh, Pa.) at 50° C. overnight. The lysate (100 µL) were placed in triplicate into a 96-well plate and 100 µL of Picogreen (Molecular Probes, Eugene, Oreg.) were added to each well. The plate was incubated for 5 min in the dark and then read on a fluorescent plate reader (FLX800, Bioinstrument Inc., Winooski, Vt.).

Scanning Electron Microscopy (SEM) and Atomic Force Microscopy (AFM)

For SEM, the samples were washed with PBS, fixed in 2.5% glutaraldehyde for 30-60 min, and dehydrated in graded ethanol solutions. The samples were dried by hexamethyldisilazane (HMDS) evaporation, mounted, and sputter-coated with iridium. Observations were made using a Nova 400 Nano SEM (FEI, Hillsboro, Oreg.) under low-vacuum conditions. For AFM, the samples were fixed with 4% paraformaldehyde (PFA), dehydrated at 60° C., and then analyzed in contact mode using a Dimension 3000 scanning probe microscope (Digital Instruments, Santa Barbara, Calif.). The roughness and topography were assessed from the acquired information.

Immunocytochemistry

For ECM expression, the monolayers, aggregates, or EBs before and after decellularization were fixed with 4% PFA (33). The samples were permeabilized with 0.2-0.5% Triton X-100, blocked, and incubated with primary ECM antibodies, including rabbit polyclonal fibronectin (FN), laminin (LN), collagen IV (Col IV), and vitronectin (VN) (Abcam, Cambridge, Mass.). For fluorescence staining, the samples were incubated with ALEXA FLUOR 488 goat anti-Rabbit IgG (Molecular Probes), counterstained with 4',6-Diamidino-2-Phenylindole (DAPI), and visualized using a fluorescence microscope (Olympus IX70, Melville, N.Y.) or a Zeiss 510 confocal microscope (Leica TCS SP2 AOBS, Bannockburn, Ill.). For the detection of glycosaminoglycans (GAGs), the samples were incubated in 1% Alcian blue 8GX (Sigma) diluted in 3% acetic acid (pH=2.5) for 30 min, washed with water, and analyzed under light microscope.

To quantify the ECM contents, the samples were incubated with donkey anti-Rabbit IgG conjugated with horseradish peroxidase (HRP, Rockland Immunochemicals, Inc., Gilbertsville, Pa.) after the incubation with primary antibodies. After washing, 1 mL of 3,3',5,5'-tetramethylbenzidine (TMB) substrate (Thermo scientific, Hudson, N.H.) was added to the samples, incubated for 5-25 min, and stopped by a solution of 0.16 M sulfuric acid. The absorbance units (AU) were measured using a microplate reader (Biorad, Richmond, Calif.) at a wavelength of 405 nm with background subtraction at 655 nm. The AU values were also corrected by subtracting the absorbance of negative control stained with HRP-IgG only. The measurements were normalized to the cell number for comparison.

To detect differentiation markers, the cells were incubated with mouse or rabbit primary antibody against: Nestin (Millipore), β-tubulin III (Sigma), α-actinin (sarcomeric, Sigma), or FOXA2 (Millipore). After washing, the cells were incubated with the corresponding secondary antibody: ALEXA FLUOR 488 goat anti-Mouse IgG$_1$ (for Nestin and α-actinin) or IgG$_{2b}$ (for β-Tubulin III), or ALEXA FLUOR 488 goat anti-Rabbit IgG (for FOXA2). The localization of RAR-α was also assessed using goat anti-Rabbit RAR-α antibody (Abcam) detected by ALEXA FLUOR 594 donkey anti-Goat IgG.

Cell Reseeding and Cultivation on the Decellularized ECMs

To assess cell proliferation, ESCs of $0.5 \times 10^5$ per mL were seeded on the decellularized ECMs and cultivated for 4 days in expansion media without LIF (FIG. 1). About 30-50% of seeding efficiency was observed for 3-D ECMs and 50% for 2-D ECMs. Cell numbers were determined at days 0, 2, and 4 using a hemocytometer after trypsin/EDTA dissociation. The specific growth rates were calculated as the slope of the proliferation curve. Cell viability was determined by the incubation with 5 mg/mL 3-(4,5-Dimethylthiazol-2-yl)-2,5-diphenyltetrazolium bromide (MTT, Sigma) solution. Afterwards, the formazan crystals were hydrolyzed with dimethyl sulfoxide (Sigma) and measured at 500 nm using a microplate reader. For the test of RA signaling, soluble RA (1 µM) or BMS 493 (1 µM, Santa Cruz), a pan-RAR antagonist, was supplemented in the media. To assess the differentiation ability after culturing on the decellularized ECMs, ESCs were replated on 0.1% gelatin-coated 12-well plates and cultured for 7 days in differentiation medium without any inducing growth factors. The cells were evaluated for the expression of Nestin (ectoderm), β-tubulin III (ectoderm), α-actinin (mesoderm), and FOXA2 (endoderm).

Bromodeoxyuridine (BrdU) Assay

The cells were incubated in the media containing 10 µM BrdU (Sigma) for 30 minutes to allow BrdU, a synthetic thymidine analog, incorporating into the DNA during S-phase of cell cycle. The cells were then fixed with 70% cold ethanol, followed by a denaturation step using 2N HCl/0.5% Triton X-100 for 30 minutes in the dark. The samples were reduced with 1 mg/mL sodium borohydride for 5 minutes and incubated with mouse anti-BrdU (Invitrogen) in blocking buffer (0.5% Tween 20/1% bovine serum albumin in PBS), followed by the incubation with ALEXA FLUOR 488 goat anti-Mouse $IgG_1$. The cells were mounted with DAPI and visualized using a Zeiss 510 confocal microscope.

Flow Cytometry

For flow cytometry, $1 \times 10^6$ cells per sample were fixed with 4% PFA and washed with staining buffer (2% FBS in PBS). The cells were stained with DNA-intercalating dye ethidium monoazide bromide (EMA, Sigma) and permeabilized with 100% cold methanol. The samples were incubated with primary antibodies against Oct-4 (Millipore), Nestin, β-tubulin III, α-actinin, or FOXA2 followed by the corresponding secondary antibody: ALEXA FLUOR 488 goat anti-Mouse $IgG_1$ (for Oct-4, Nestin, and α-actinin) or $IgG_{2b}$ (for β-tubulin III), or ALEXA FLUOR 488 goat anti-Rabbit IgG (for FOXA2). The cells were acquired with BD FACSCANTO II flow cytometer (Becton Dickinson) and analyzed against isotype controls using FlowJo software.

Statistical Analysis

Each experiment was carried out at least twice. The average values of two or three independent experiments were presented and the results are expressed as [mean±mean absolute deviation (MD)]. In each experiment, triplicate samples were used. To assess the statistical significance, ANOVA followed by Fisher's LSD post hoc tests or t-tests were performed. A p-value<0.05 was considered statistically significant.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Derivation and Characterization of Decellularized ECM from ESCs

Figure 2A:
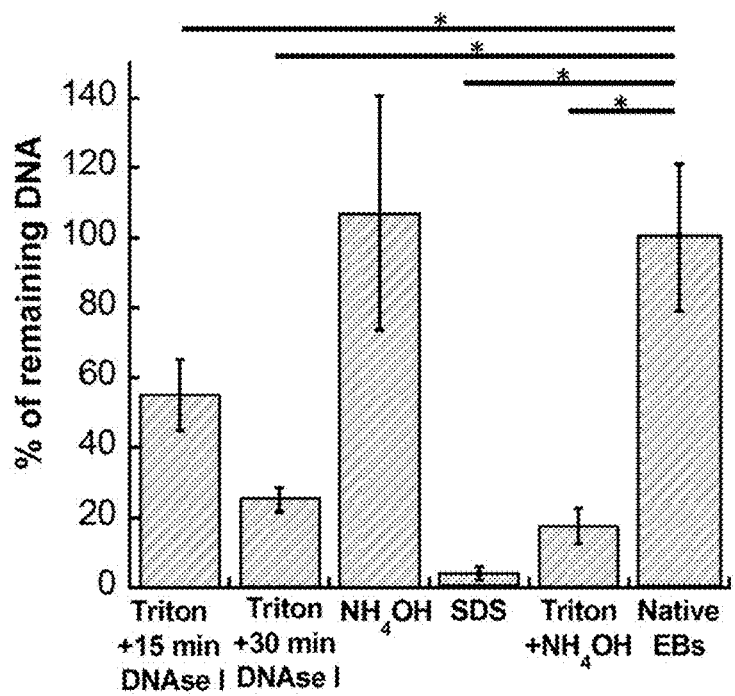
FIGS. 2A and 2B. Comparison of decellularization methods for DNA removal and ECM preservation. EBs after 3-day culture were decellularized with different methods.
Figure 2B:
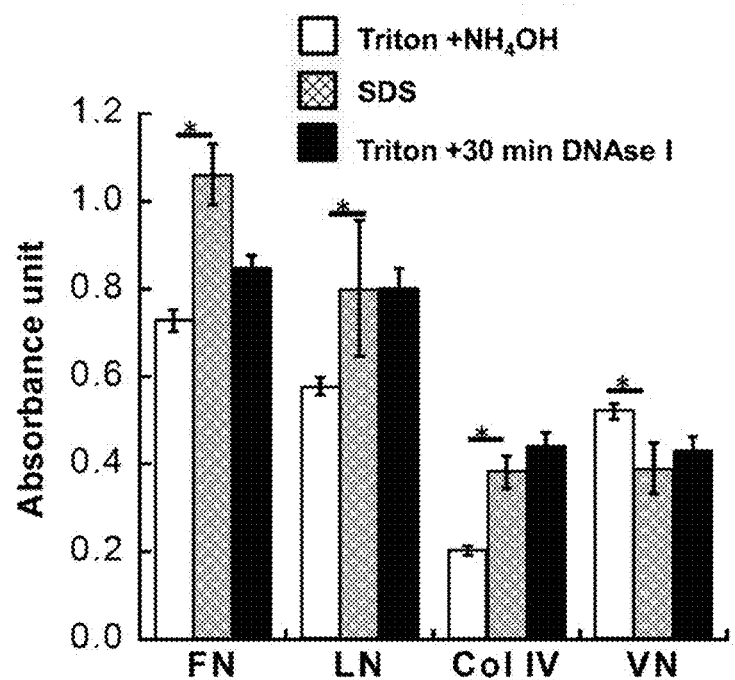

Among the various decellularization methods tested, SDS condition displayed the highest efficiency of DNA removal with less than 5% DNA remained in the acellular structure (FIG. 2A). Treatment with Triton X-100 was also effective when DNAse incubation increased from 15 min to 30 min (55% vs. 21%). $NH_4OH$ treatment alone did not reduce DNA content and its combination with Triton X-100 did not add beneficial effect. For ECM proteins, SDS treatment maintained the expression of FN, LN, and Col IV but reduced VN slightly (FIG. 2B). Treatment with Triton X-100 plus 30 min DNAse was comparable to SDS condition while co-treatment with $NH_4OH$ reduced LN and Col IV. Because the SDS-treated ECMs displayed viscous, semi-fluidic appearance which was difficult to handle, Triton X-100 plus 30 min DNAse treatment was chosen in the following studies (Table 1).

Figure 3A:
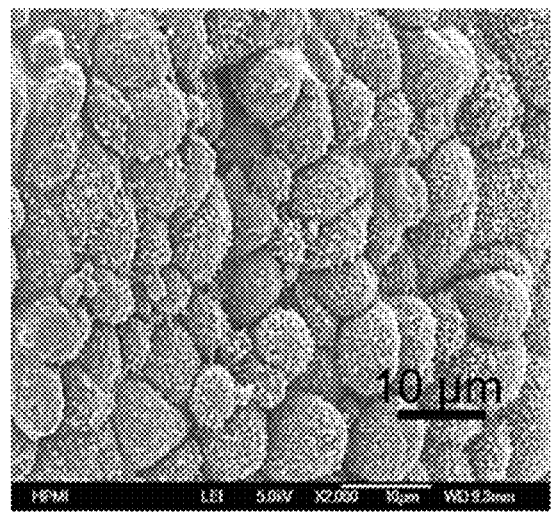
FIGS. 3A-3C. Characterization of surface topography of decellularized ECMs. Monolayers, aggregates, and EBs were decellularized after 3 days of culture.
Figure 3A:
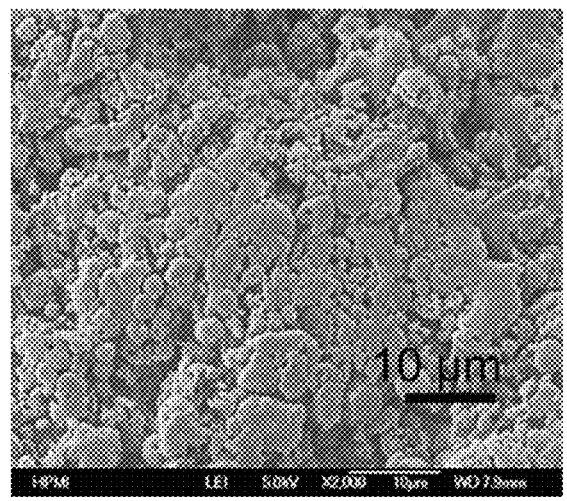
Figure 3B:
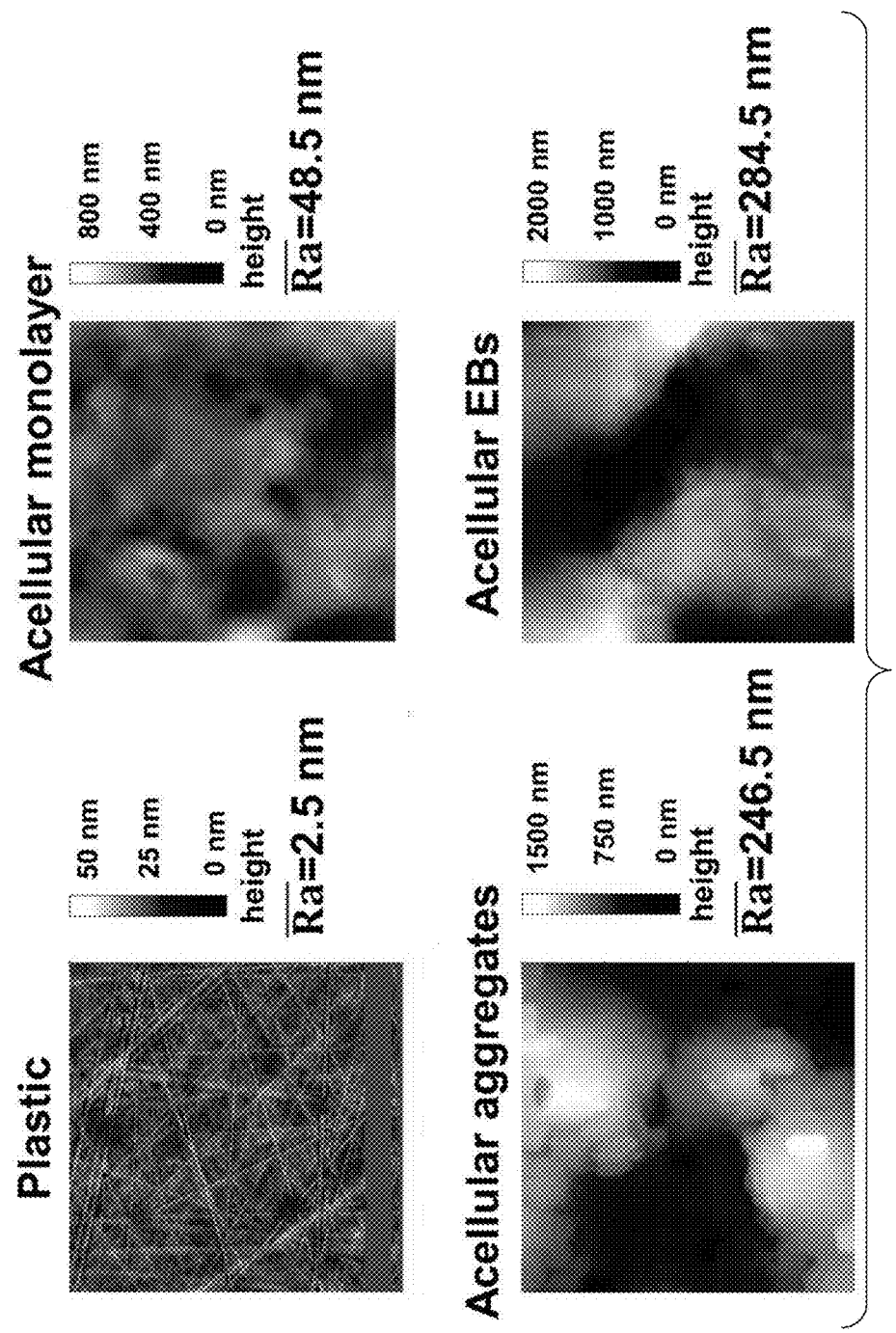

Ultrastructure analysis of the decellularized ECMs revealed contrasting morphologies before and after decellularization, with tightly packed cells becoming indistinguishable after the treatment (FIG. 3A). Compared to gelatin-coated surface, the roughness (Ra) increased from 3 nm to 48 nm for the decellularized monolayers. The surface roughness was comparable for the decellularized aggregates and EBs (246 vs. 285 nm) and both were much higher than that of the decellularized monolayers (FIG. 3B), suggesting distinct ultrastructure characteristics of the decellularized ECMs from different ESC organizations.

EXAMPLE 2

ECM Protein Expression Before and after Decellularization

Figure 3C:
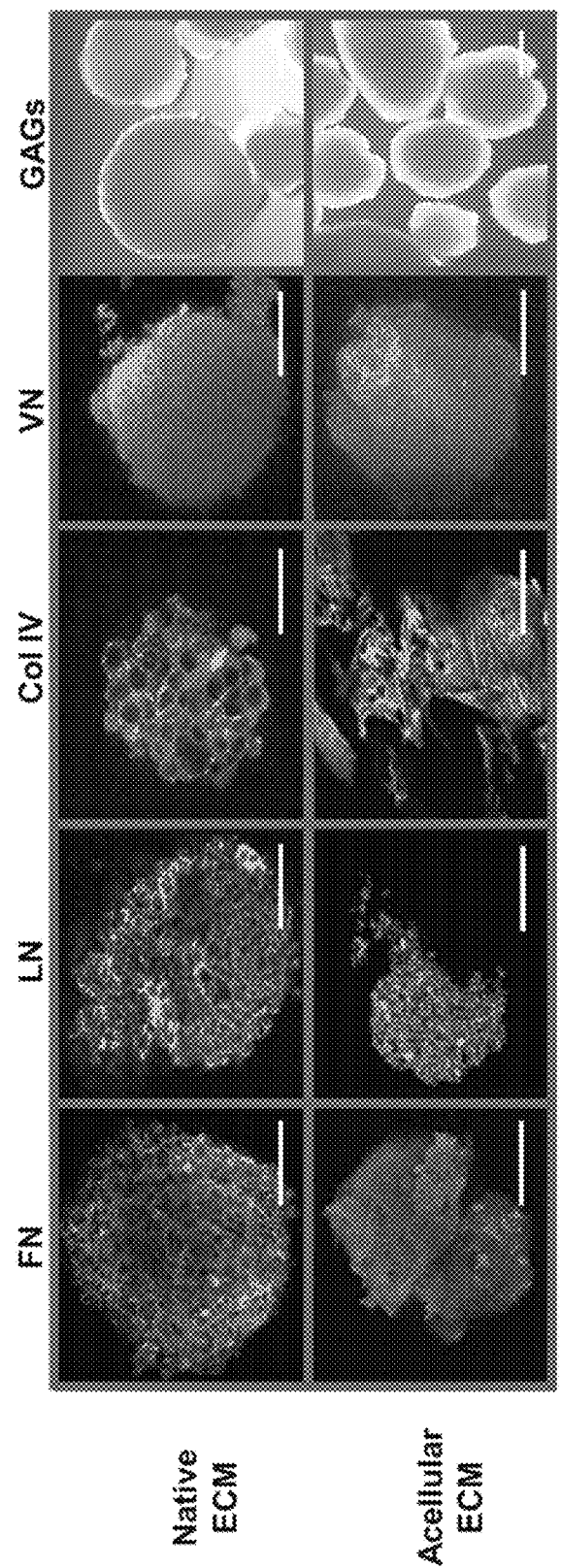
Figure 9:
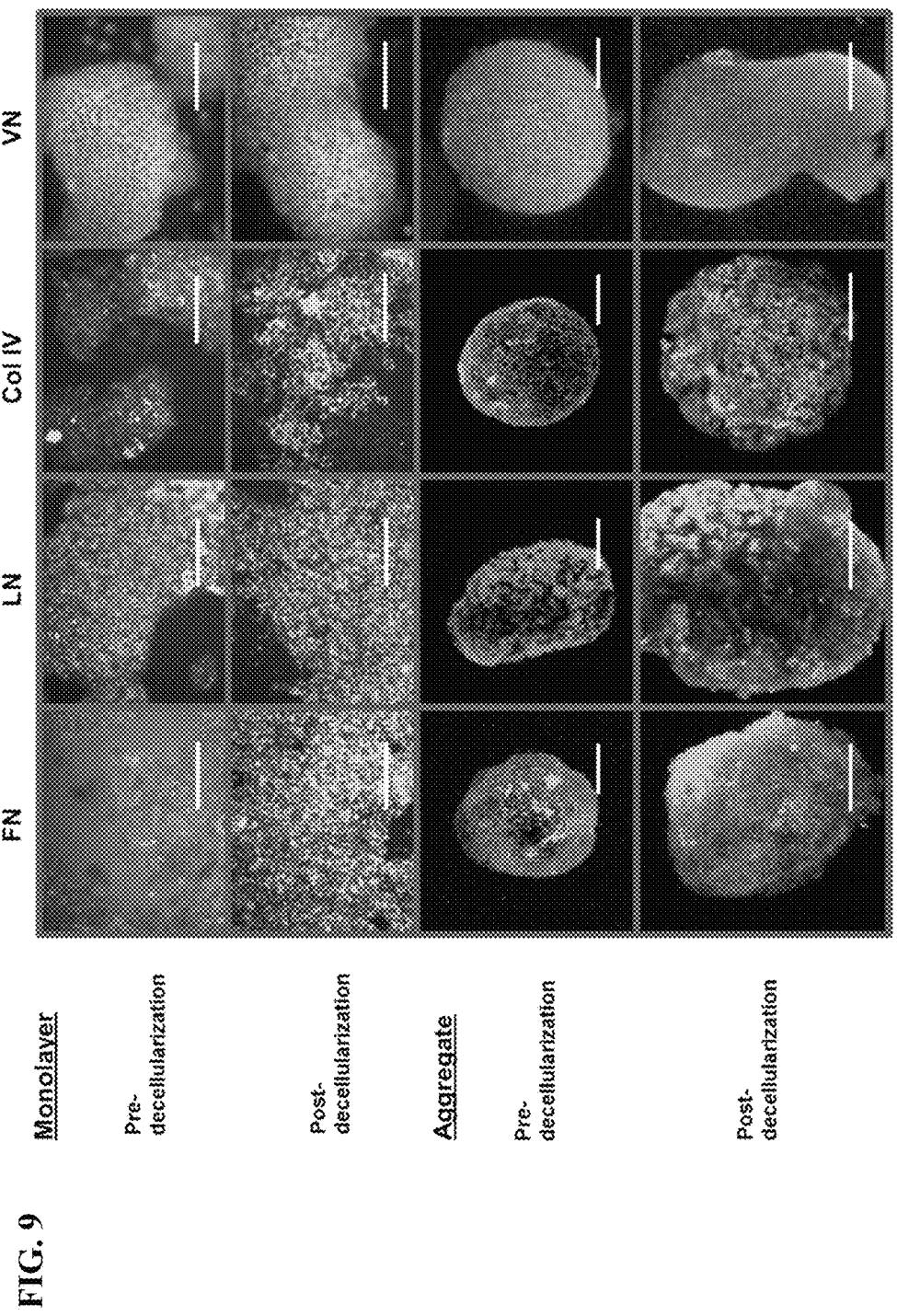
FIG. 9. Expression of ECM proteins (FN, LN, Col IV, and VN) pre- and post-decellularization of day 3 ESC monolayers (fluorescent images) or day 3 ESC aggregates (confocal images). Scale bar: 100 µm.

ECM expression including FN, LN, Col IV, VN, and GAGs was preserved after decellularization. The ECMs from aggregates and EBs exhibited denser structures due to the compaction by centrifugation (FIG. 3C, FIG. 9).

Figure 4A:
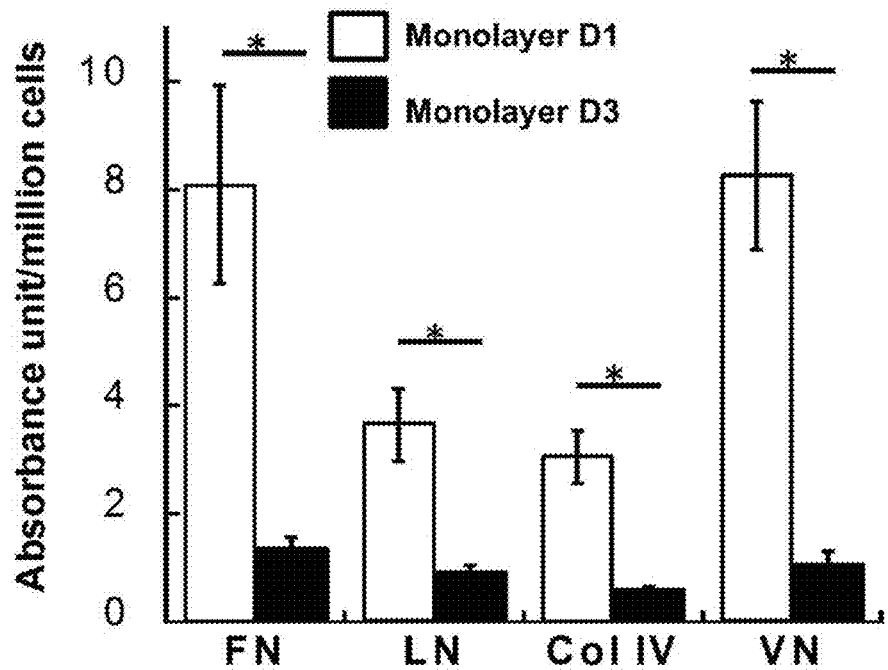
FIGS. 4A-4D. Quantitative analysis of ECM composition pre- and post-decellularization of undifferentiated ESCs.
Figure 4B:
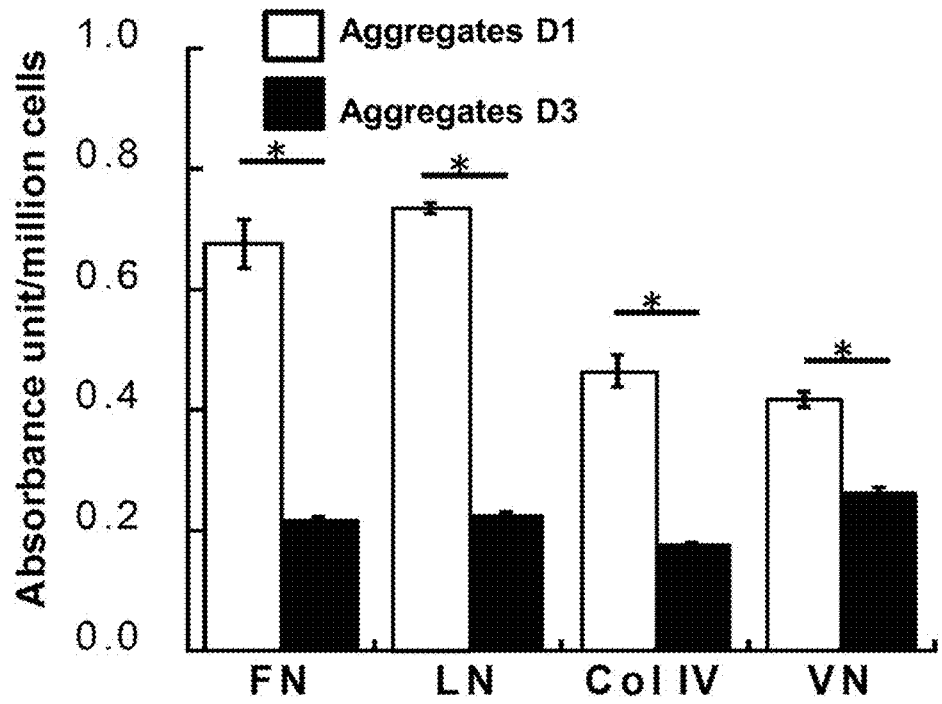
Figure 4C:
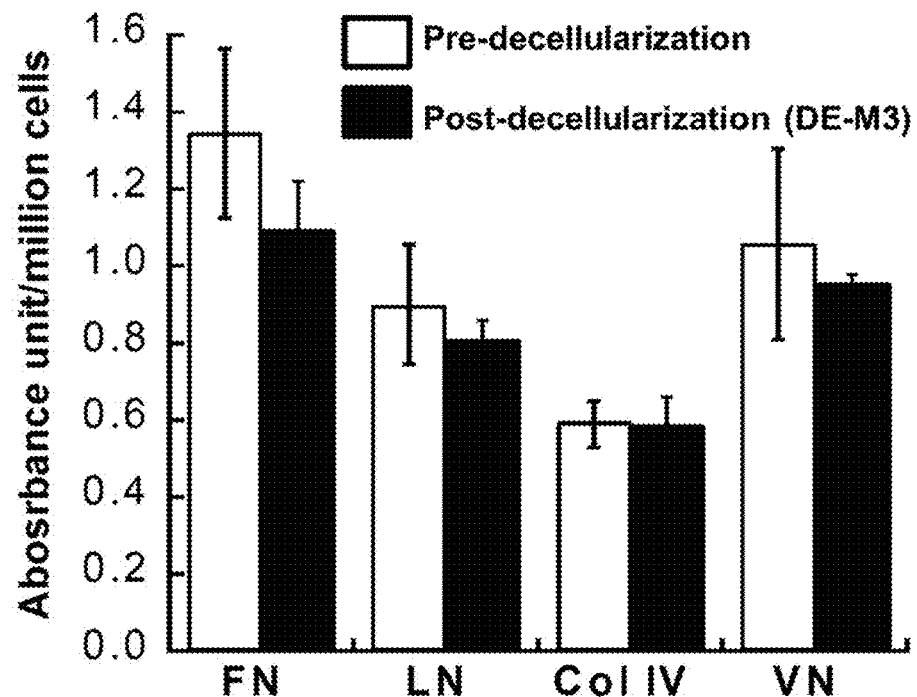
Figure 4D:
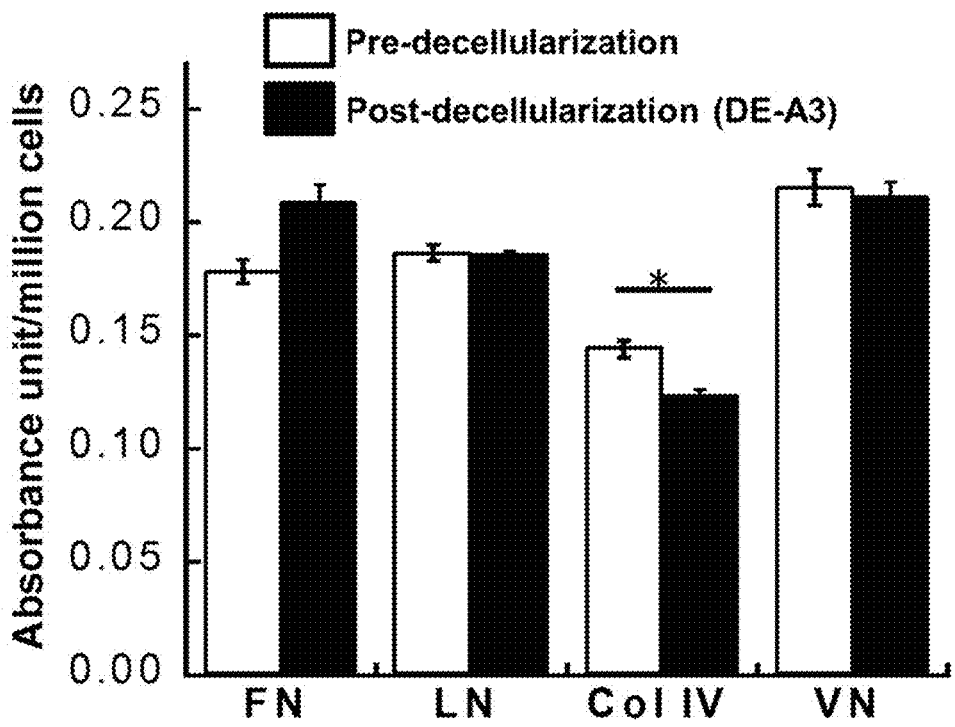

The specific ECM expression decreased by 4-8 folds over 3 days of monolayer culture (FIG. 4A). Similarly, for the ESC aggregates, specific ECM expression also significantly decreased (2-4 folds) with culture time (FIG. 4B). After decellularization, the expression of ECM proteins in the monolayers (DE-M) was unchanged (FIG. 4C), indicating that decellularization did not modify ECM composition. For the decellularized aggregates (DE-A), the expressions of FN, LN, and VN were maintained with a slight decrease in Col IV expression (FIG. 4D). Despite the higher specific ECM expression at day 1 compared to day 3, the quantity and surface coverage of day 1 ECMs were not sufficient for cell reseeding. So the decellularized ECMs from day 3 monolayers or aggregates were used in the subsequent studies.

Figure 5B:
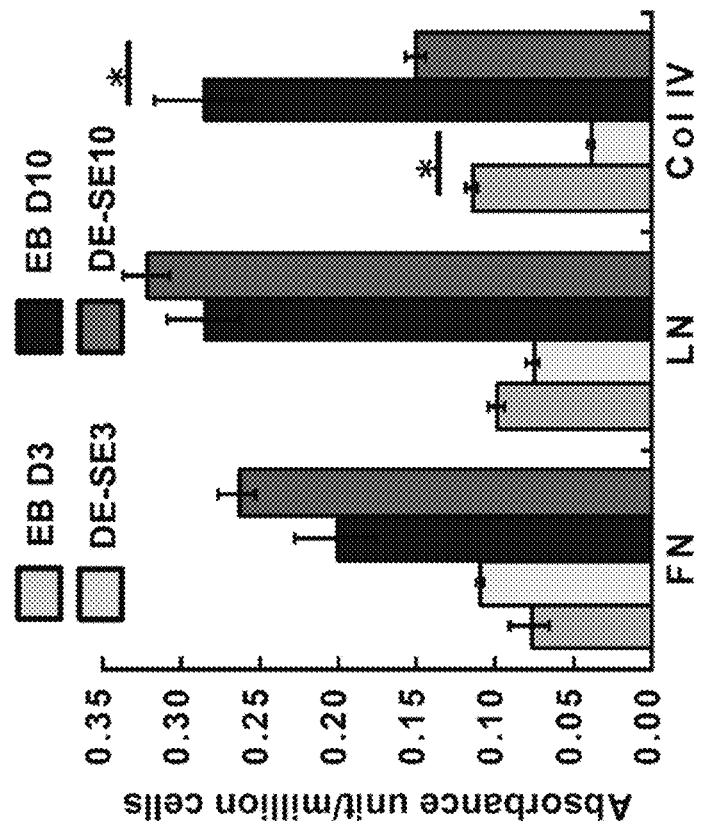
FIGS. 5A-5D. Quantitative analysis of ECM compositions pre- and post-decellularization of EBs.
Figure 5A:
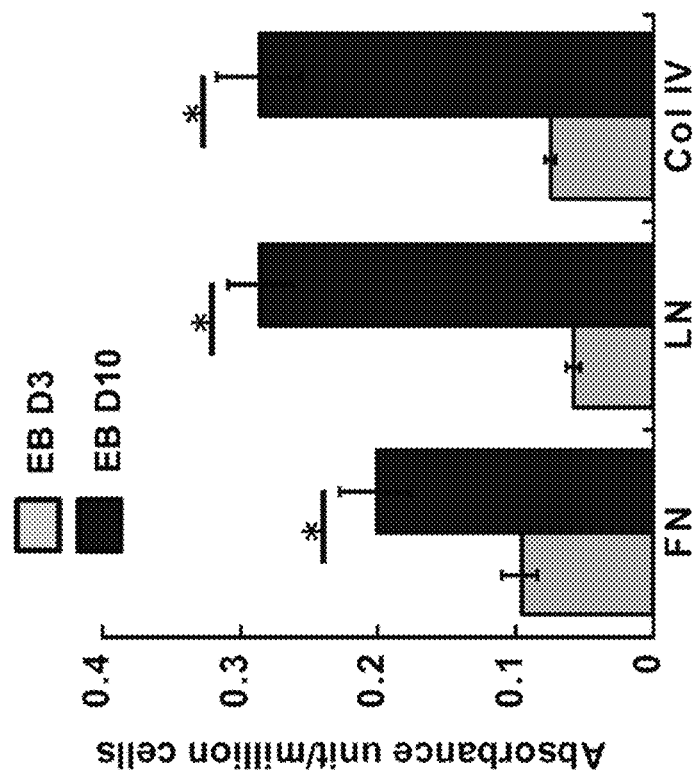
Figure 5C:
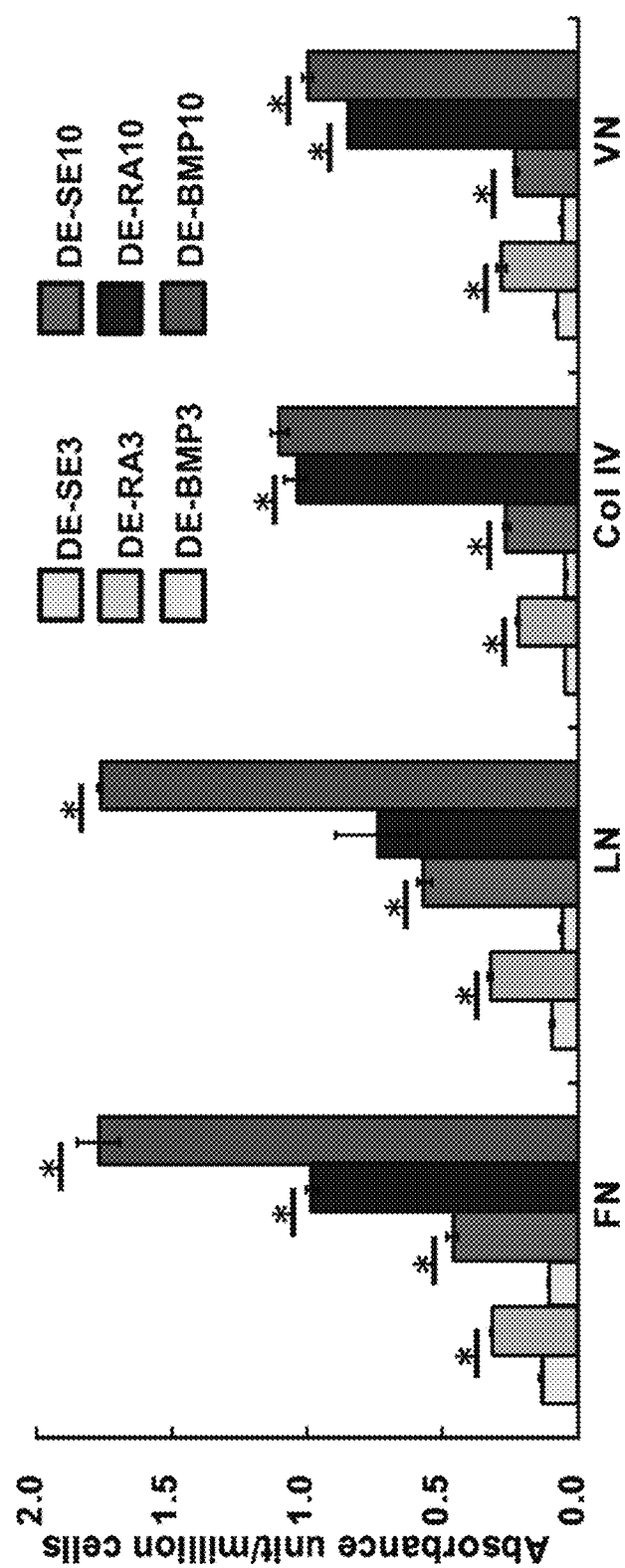
Figure 5D:
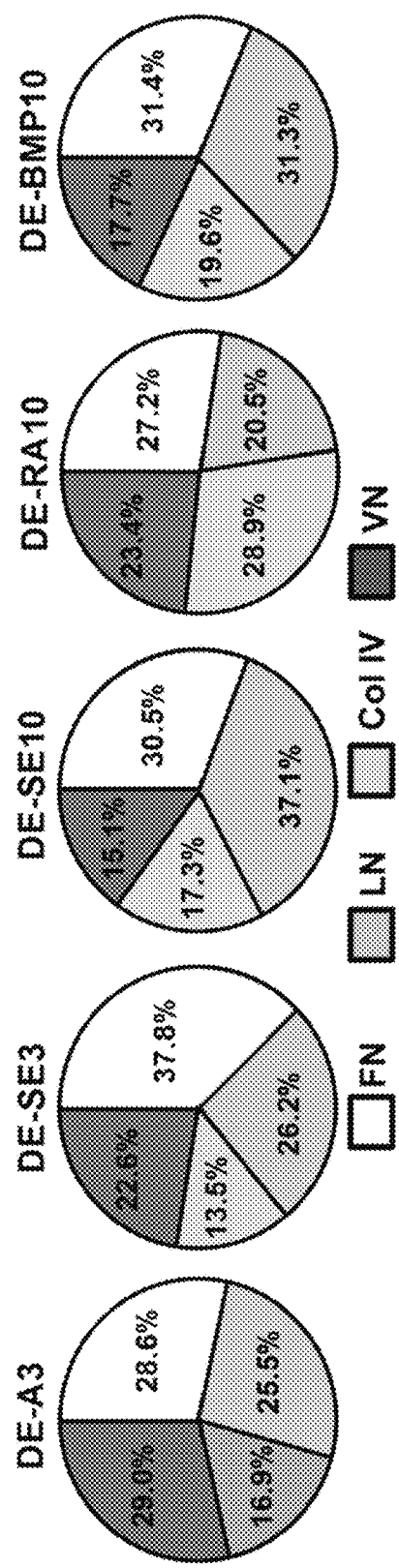

For the spontaneously differentiated EBs, extended culture from 3 days to 10 days increased the specific ECM expression by 2-4 folds (FIG. 5A). Following decellularization, the expressions of FN and LN were maintained while Col IV expression was reduced (FIG. 5B). For the growth factor-treated EBs, the differences in ECM expressions among the DE-SE, DE-RA, and DE-BMP were more pronounced for day 10 samples compared to day 3 samples, with the DE-RA10 and the DE-BMP10 having higher specific VN and Col IV expression compared to the DE-SE10 (0.8-1.1 vs. 0.2-0.3) (FIG. 5C). For FN and LN, the expression was differentially observed for the DE-SE10, DE-RA10, and DE-BMP10 (0.4-0.6, 0.7-1.0, 1.7-1.8 respectively). To ensure sufficient signals, day 10 samples of the DE-BMP and the DE-RA were used to further evaluate cellular responses. The relative proportions of ECM proteins for various decellularized ECMs were summarized in FIG.

5D. Specifically, the DE-RA10 displayed 10% higher Col IV compared to other ECMs and higher proportion of VN than the DE-SE10 and the DE-BMP10 (23% vs. 15-18%), while the DE-SE10 and the DE-BMP10 had higher LN (38% and 30%) compared to other ECMs (20-26%). These results indicated that the decellularized ECMs were dynamically remodeled during ESC expansion and differentiation.

EXAMPLE 3

Effects of the Decellularized ECMs on ESC Proliferation

ESC proliferation on the decellularized matrices was assessed. The specific growth rate of ESCs on the DE-M3 or the DE-A3 was similar to gelatin control ($4 \times 10^{-2}$ $h^{-1}$) (FIG. 6A). Cells on the DE-SE3 had slightly lower growth rate without statistical significance ($3.1 \times 10^{-2}$ $h^{-1}$). The ESCs seeded on the DE-RA10 had significant lower specific growth rate compared to the DE-BMP10 and the DE-SE10 scaffolds (1.6 vs. $3.5-4 \times 10^{-2}$ $h^{-1}$). The cell viability determined by MTT assay was consistent with the specific growth rates (FIG. 6B). BrdU staining revealed the spatial distribution of the proliferating ESCs after reseeding. While the BrdU$^+$ cells evenly distributed in the DE-SE10 and the DE-BMP10, less BrdU$^+$ cells were observed in the central region of the DE-RA10 (FIG. 6C).

Figure 6D:
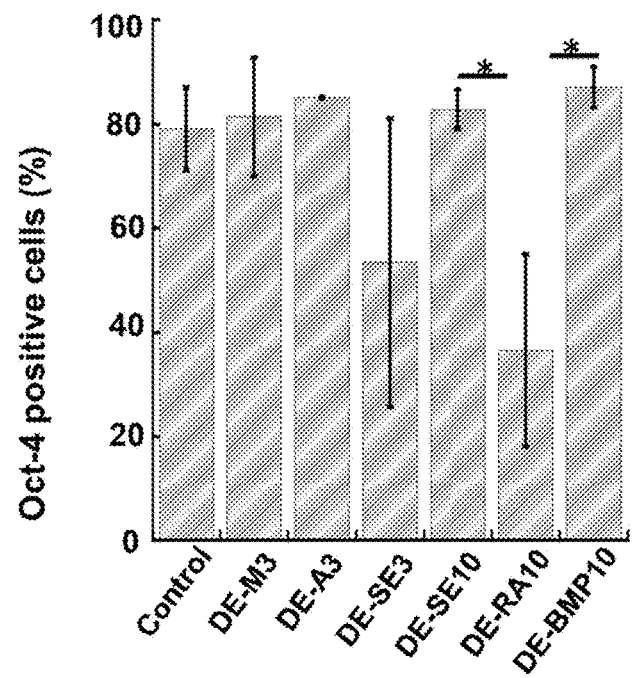
Figure 6E:
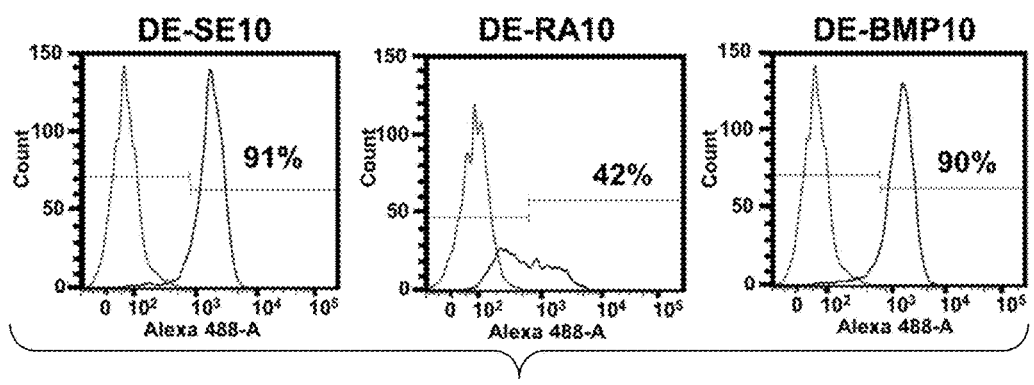
Figure 7A:
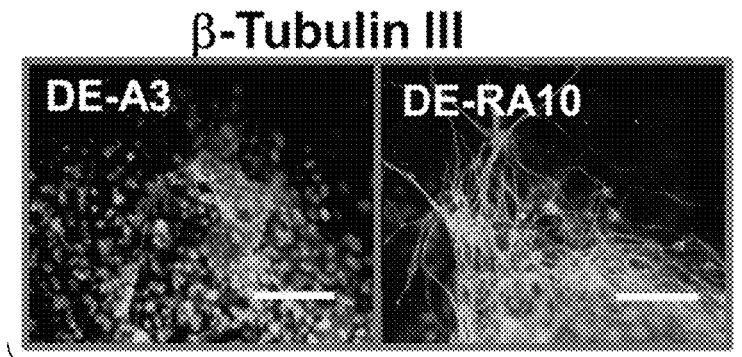
FIGS. 7A-7L. Three-germ layer differentiation of ESCs grown on decellularized ECM scaffolds. Representative fluorescence images and flow cytometry histograms of β-tubulin III (FIGS. 7A, 7B), Nestin (FIGS. 7D, 7E), α-actinin (FIGS. 7G, 7H), and FOXA2 (FIGS. 7J, 7K) expression of cells seeded on the DE-A3 and the DE-RA10. Scale bar: 50 µm. Percentage of positive cells for β-tubulin III (FIG. 7C), Nestin (FIG. 7F), α-actinin (FIG. 7I), and FOXA2 (FIG. 7L) in different ECM scaffolds. *p-value<0.05.
Figure 7B:
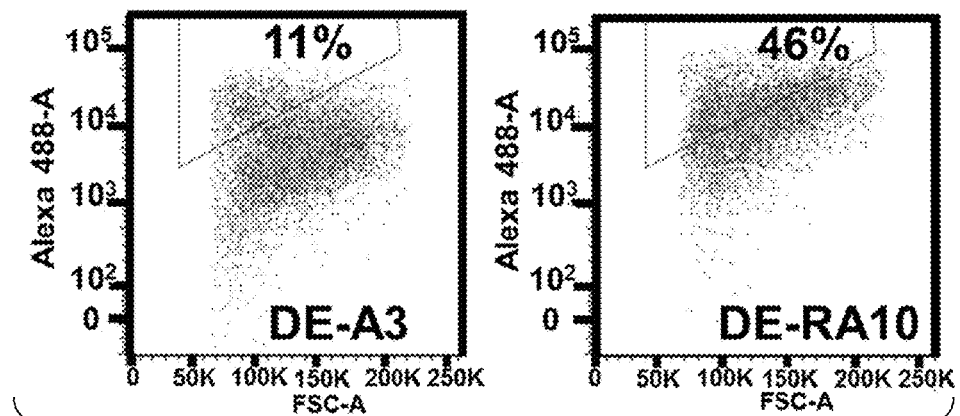
Figure 7C:
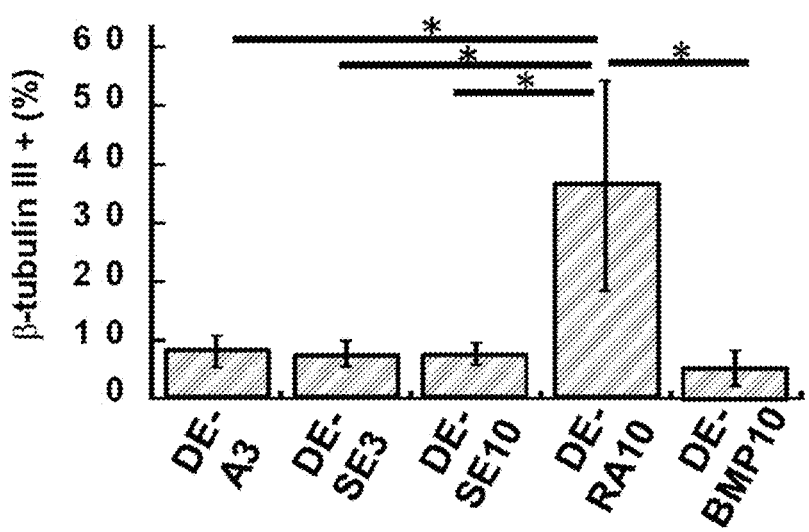
Figure 7D:
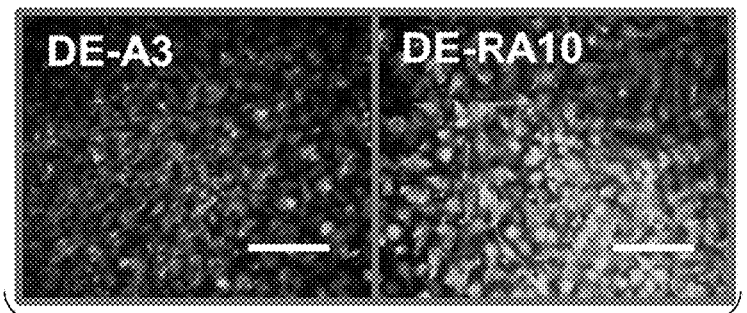
Figure 7E:
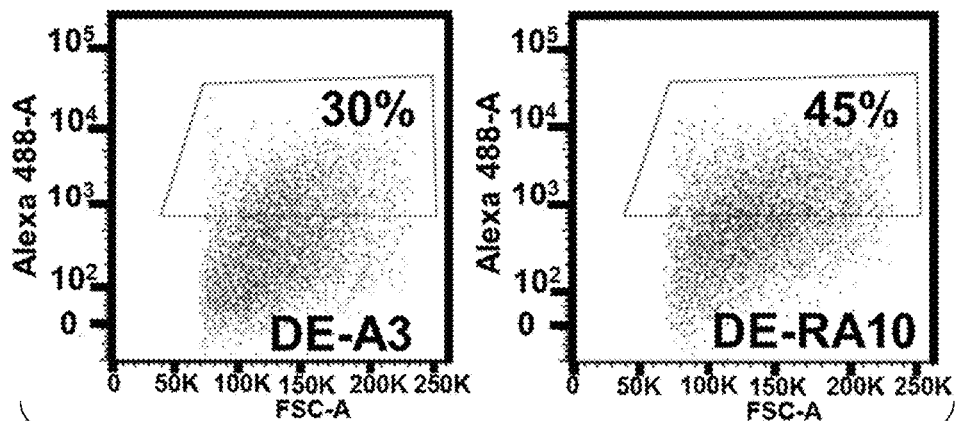
Figure 7F:
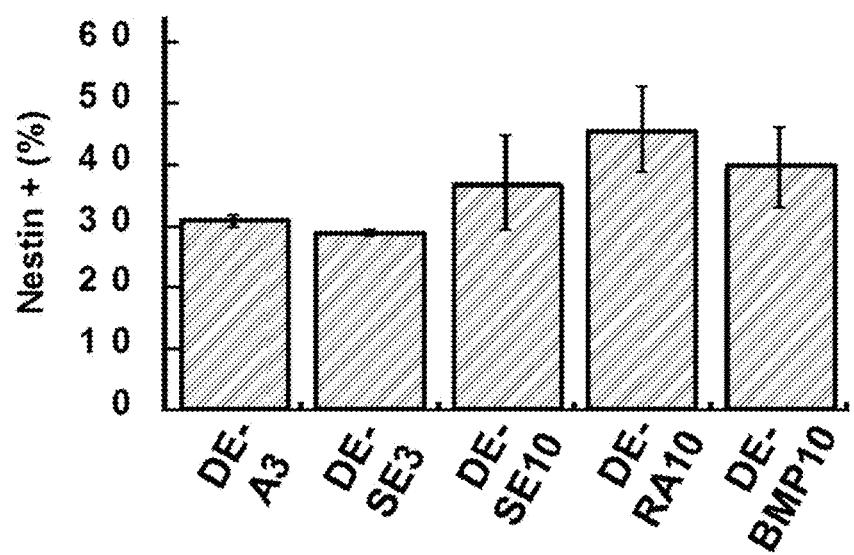
Figure 7G:
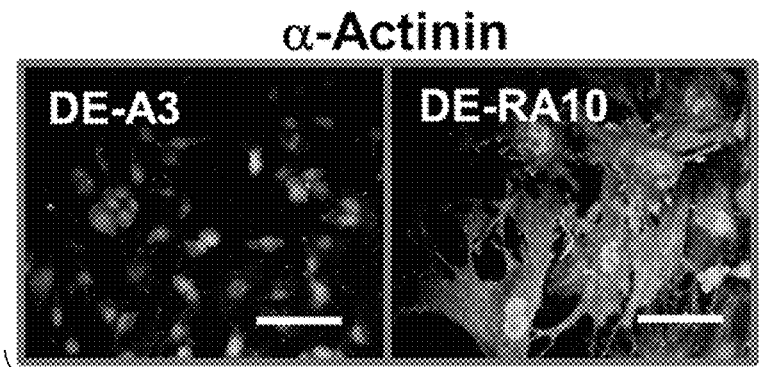
Figure 7H:
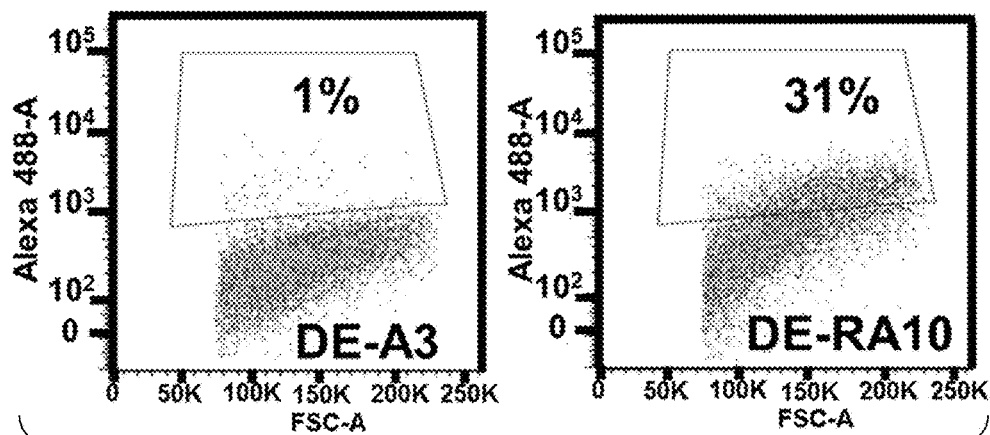
Figure 7I:
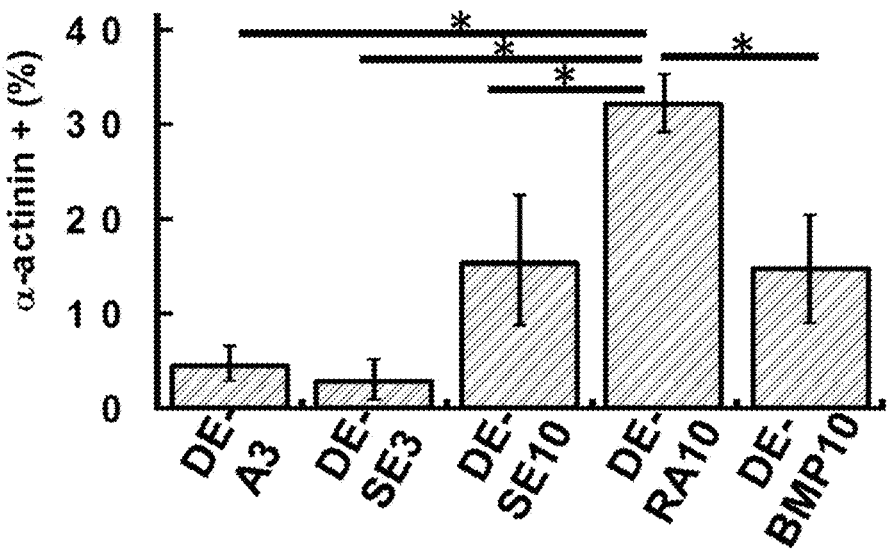
Figure 7J:
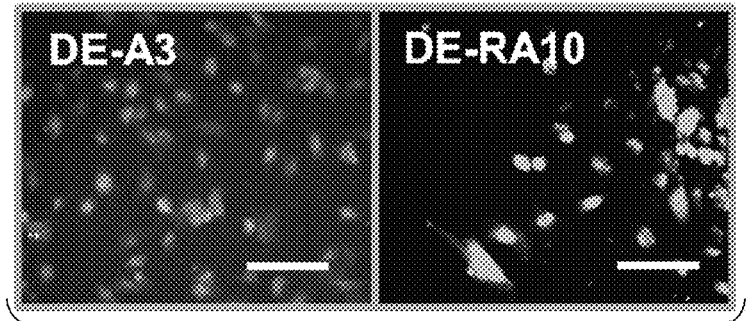
Figure 7K:
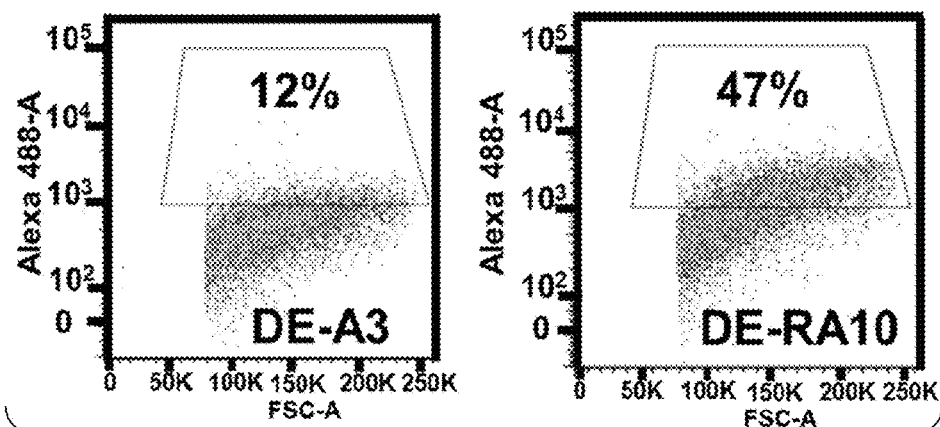
Figure 7L:
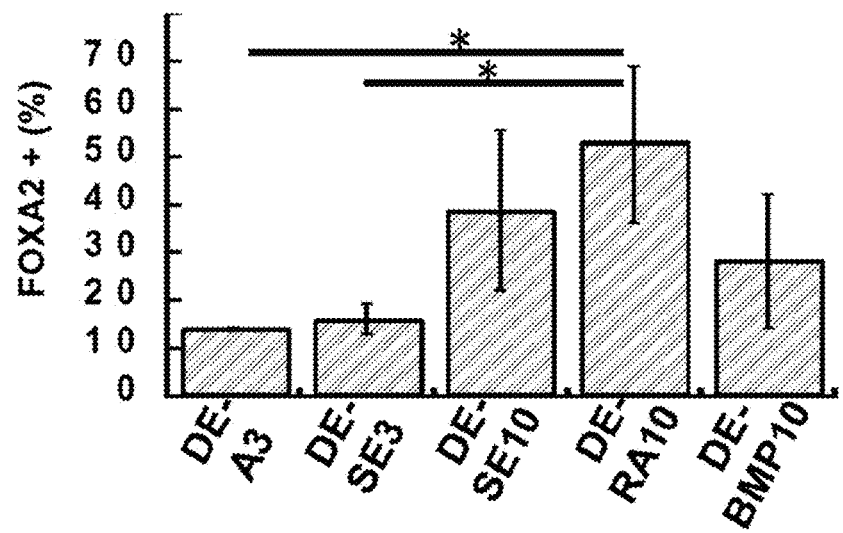

The Oct-4 expression of ESCs followed similar trend as observed in the specific growth rates. About 81-86% of the cells seeded on the DE-M3 and the DE-A3 were Oct-4 positive, similar to the gelatin-coated surface (FIG. 6D). The DE-SE3 supported a lower percentage of Oct-4$^+$ cells, but the difference was not statistically significant compared to gelatin control. While the DE-SE10 and the DE-BMP10 maintained 84-91% Oct-4$^+$ cells, Oct-4 expression of cells on the DE-RA10 was only 38% (FIGS. 6D, 6E). Similar trend was observed for SSEA-1 (data not shown).

EXAMPLE 4

Effects of the Decellularized ECMs on ESC Differentiation

Cells seeded on various decellularized ECM scaffolds were assessed for the ability of differentiation into three-germ layers (FIGS. 7A-7L). Due to the absence of inducing growth factors, the lineage-specific differentiation for cells on various ECM scaffolds was mainly attributed to the signals from the ECMs. The expression of α-actinin in this study represented mainly skeletal muscle cells rather than cardiac muscle cells due to the low frequency of beating cells. For the cells grown on the day 10 DEs (DE-SE10, DE-RA10, and DE-BMP10), higher expression of FOXA2 (28-52% vs. 14-16%) and α-actinin (15-32% vs. 4-5%) were observed compared to the cells grown on the day 3 DEs (DE-A3 and DE-SE3). Specifically, after differentiation, the ESCs seeded on the DE-RA10 had the highest expression of Nestin (46%), α-actinin (32%), β-tubulin III (36%), and FOXA2 (52%) compared to the cells seeded on the other ECM scaffolds (FIGS. 7C, 7F, 7I, 7L).

EXAMPLE 5

Role of RA-RAR Interactions

To investigate the role of RA signaling in the ECM scaffolds, RAR-α expression by ESCs cultured on the DE-RA10 was evaluated. Mixed locations of RAR-α in the cytoplasm and cell nucleus were observed (FIG. 8A). The translocation of RAR-α from cytoplasm to cell nucleus was confirmed for ESCs exposed to soluble RA (FIG. 8A). Because no soluble RA was added in the DE-RA10 culture, the mixed pattern of RAR-α expression suggested active RA signaling presumably originating from the decellularized ECMs. The cells grown in the DE-RA10 were also compared with the cells treated with soluble RA (FIG. 8B). Higher specific growth rate (0.9 vs $-1.3 \times 10^{-2}$ $h^{-1}$) and Oct-4 expression (61.0% vs 10.1%) were observed for the cells in the DE-RA10. The expression of α-actinin and FOXA2 was similar for both groups (FIG. 8D). However, lower β-tubulin III (4% vs. 25%) and higher Nestin (44% vs. 32%) expression, indicating more primitive neural phenotype, were observed for the cells in the DE-RA10.

Addition of a pan-RAR antagonist, BMS 493, in the DE-RA10 culture reduced ESC proliferation but not Oct-4 expression (FIG. 8C). Upon differentiation, blocking RA-RAR signaling significantly reduced the expression of α-actinin (3% vs. 18%) and FOXA2 (24% vs. 40%) compared to the untreated group (FIG. 8E). Conversely, Nestin expression was increased in the treated group with similar β-tubulin III expression. These results indicated that the effect of the DE-RA10 on the endodermal and mesodermal differentiation of the reseeded ESCs may be a consequence of the active RA signaling.

EXAMPLE 6

Different from ECMs derived from somatic cells, the decellularized ECMs from PSCs recapitulate the developmentally relevant extracellular microenvironments and have unique signaling capacity for directing cell fate (6,10). The results of the present invention demonstrates the organization- and lineage-specific characteristics of ESC-derived ECMs and their differential signaling capacity in regulating ESC fate.

Characterization of ESC-Derived ECM Scaffolds

Formation of EB is an important step in ESC differentiation in vitro and the derivation of decellularized matrices from spontaneous EBs has been demonstrated in several studies (11,12). However, ESCs are also able to form 3-D aggregates while maintaining the undifferentiated phenotype, which facilitates their expansion in suspension (25). The differences of ESC fate in the EB vs. the 3-D aggregate may be reflected in their ECM microenvironment, but the derivation and properties of the ECMs from the 3-D aggregates have not been reported. In the present study, Triton X-100 followed by DNAse was effective in maintaining the 3-D structures of ESC aggregates similar to those derived from EBs. Despite a slight decrease in Col IV, the main components of ECM proteins in the 3-D ESC aggregates were preserved.

While the decellularized matrices derived from EBs and ESC aggregates have similar macroscopic structures, they represent divergent developmental stages and thus may have different ECM compositions and signaling capacities. Indeed, quantitative assessment of the decellularized matrices revealed time- and organization-dependent ECM compositions. The specific expression of ECM proteins increased with time during EB development, in contrast to the decreasing trend for the undifferentiated ESC aggregates and the monolayer cultures. The increased specific ECM production in the EBs, correlating with basement membrane formation, is thought to be a result of ESC three-germ layer differentiation mimicking the embryonic development (10, 37,38). To further probe whether the decelluarized ECMs maintain their lineage-specific properties, the EBs were treated with BMP-4 or RA to induce mesodermal or ectodermal differentiation (31,32). The significantly increased ECM expression and the differential expression patterns for both groups suggest the close association of ECM properties with ESC lineage specification. Together, these results suggest that the decellularized ECMs recapitulate the cellular microenvironments associated with ESC development in vitro and that the characteristics of ECMs derived from ESC cultures depend on both spatial organization and lineage specification.

ESC Proliferation on the Decellularized ECM Scaffolds

The decellularized ECMs, except the DE-RA10, supported short-term ESC proliferation and Oct-4 expression at a level comparable to that of gelatin-coated surface. It is interesting to note that no significant difference in cell proliferation was observed between the DE-A and the DE-SE groups, two types of matrix with divergent ECM compositions. This may be explained by the fact that multiple components in the decellularized ECMs influence ESC proliferation. Compared to the purified ECM proteins, the decellularized ECMs contain a mixture of ECM proteins and provide a multitude of binding sites for both cell adhesions and growth factor sequestrations (5,6,39). Studies have shown that the combinatorial ECMs supported human ESC expansion more robustly compared to individual ECM proteins, probably due to the increased cell binding and integrin signaling (40,41).

The significant reduction in ESC proliferation and Oct-4 expression in the DE-RA10 scaffold indicates its unique ECM microenvironment. Obtained over same culture period, the DE-SE10, the DE-BMP10 and the DE-RA10 groups represent the microenvironments of three distinct developmental paths and have different patterns of ECM expressions. However, the differences in ESC proliferation and Oct-4 expression in the DE-RA10 cannot be explained by the differences in ECM composition alone because cell proliferation was not correlated with ECM expressions among these three matrices. Instead, regulatory molecules such as RA retained in the DE-RA10 may play a critical role. Although no soluble RA existed in the DE-RA10 culture, RA may be sequestered in the ECMs and has prolonged effects on ESC proliferation and Oct-4 expression. RA is known to reduce ESC growth by increasing p27 accumulation and lower Oct-4 level by augmenting Oct-4 chromatin/transcription factor complex (42). Though unstable and susceptible to oxidative damage in aqueous solution, RA is intrinsically hydrophobic and its binding to proteins such as serum albumin could significantly prolong its half-life and biological function (43,44). These results suggest that ECMs have intimate interactions with regulatory biomolecules and can influence cell fate via sequestration and presentation of growth factors and cytokines (4,5).

ESC Differentiation on the Decellularized ECM Scaffolds

Corresponding to the reduction in cell proliferation, the DE-RA10 exhibited the most dramatic effects on ESC differentiation among all scaffolds with the increased lineage-specific differentiation into all three germ layers. RA is an important signaling molecule in embryonic development, and has been commonly used as an inducer to initiate ESC differentiation into ectoderm, mesoderm, or endoderm through the temporal- and concentration-dependent retinoid signaling (32,45-47). Comparing to soluble RA, the DE-RA10 alone exerted similar effects on mesodermal and endodermal differentiation but preserved more primitive neural phenotype as well as higher proliferation rate. These results suggest that the increased RA stability by association with ECMs has prolonged its effects on ESC differentiation that resembles in vivo morphogenesis with a balanced proliferation and differentiation (48). Although direct measurement of matrix-bound RA is not feasible due to detection limit, the co-expression of RAR-$\alpha$ in the nucleus and cytoplasm of cells grown in the DE-RA10 suggested the presence of active RA signaling in the absence of soluble RA (49). The reduced mesodermal and endodermal differentiation by blocking RA-RAR interactions using BMS 493 in the DE-RA10 provided further evidence that matrix-bound RA played an active role in directing ESC differentiation (45). Together, these results reveal the reciprocal interactions between the ECMs and RA and the capacity of such a microenvironment to regulate cell fate at a concentration range substantially lower than the non-physiological level of soluble RA (48).

The effects of decellularized ECMs derived at different developmental stages were also observed. Compared to the day 3 DEs including both DE-A3 and DE-SE3, cells grown in the day 10 DEs expressed higher level of mesodermal and endodermal markers. Due to the progression in differentiation, the day 10 DEs may contain cell-secreted signals (e.g., Cerberus) that are more inductive for differentiation compared to the day 3 DEs (10,28). In addition, the higher content of ECM proteins in day 10 DEs might also contribute to the increased $\alpha$-actinin and FOXA2 expression, because the incorporation of biomaterials in ESC aggregates has been shown to promote mesodermal and endodermal differentiation by affecting cell-cell interactions (50).

Materials and Methods for Examples 7-11

Undifferentiated ESC Cultures

ESC monolayer culture: Murine ES-D3 line (American Type Culture Collection, Manassas, Va.) was maintained on 0.1% gelatin-coated 6-well culture plates (Millipore, Temecula, Calif.) in a standard 5% $CO_2$ incubator. The expansion medium is composed of Dulbecco's Modified Eagle's medium (DMEM, Invitrogen, Carlsbad, Calif.) supplemented with 10% ESC-screened fetal bovine serum (FBS, Hyclone, Logan, Utah), 1 mM sodium pyruvate, 0.1 mM $\beta$-mercaptoethanol, penicillin (100 U/mL), streptomycin (100 µg/mL) (all from Invitrogen), and 1000 U/mL leukemia inhibitory factor (LIF, Millipore). The cells were seeded at $2-4\times10^4$ cells/cm$^2$ and sub-cultured every 2-3 days. This culture was used to generate undifferentiated aggregates, spontaneous EBs, and neural progenitor aggregates.

Figure 10:
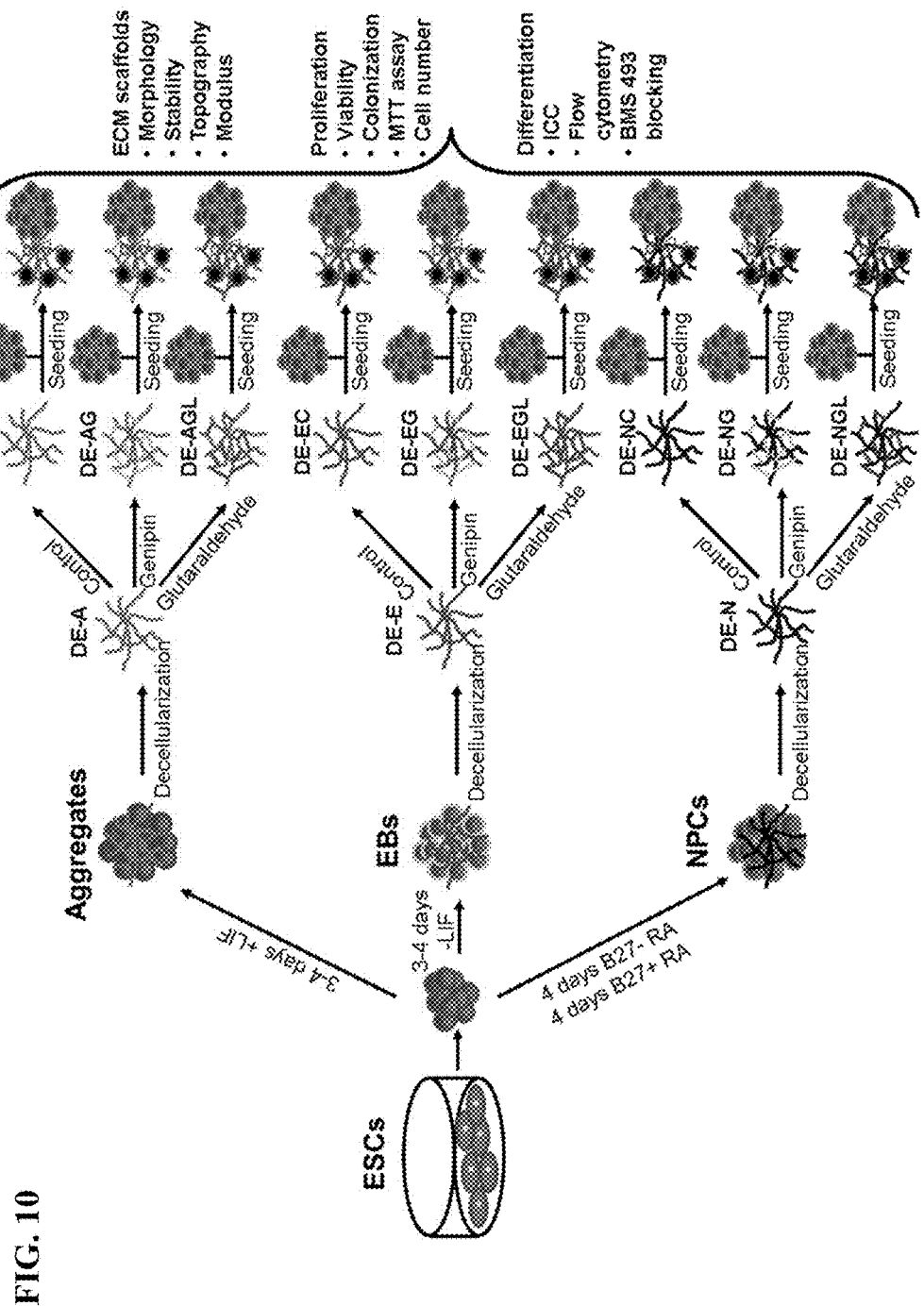
FIG. 10. Schematic diagram of the experimental procedure. Embryonic stem cells (ESCs) were seeded in suspension for 3 days in a medium containing LIF to produce undifferentiated aggregates, or alternatively without LIF to generate embryoid bodies (EBs). ESCs were also seeded in DMEM/F12-B27 for 4 days and in DMEM/F12-B27 plus retinoic acid (RA) for another 4 days to derive NPC aggregates. Undifferentiated aggregates, EBs, and NPC aggregates were then decellularized to generate DE-A, DE-E, DE-N scaffolds. The decellularized ECMs were treated with genipin (G) to generate the DE-AG, DE-EG, DE-NG scaffolds, or treated with glutaraldehyde (GL) to produce the DE-AGL, DE-EGL, DE-NGL scaffolds. The non-cross-linked ECMs were used as controls, including DE-AC, DE-EC, and DE-NC.

ESC aggregate culture: The aggregates of ES-D3 cells were obtained by seeding the cells from ESC monolayer into Ultra-Low Attachment (ULA) 6-well plates (Corning Incorporated, Corning, NY) at a seeding density of $2-4\times10^4$ cells/cm$^2$ in 3 mL growth media containing LIF [33]. The aggregates were cultivated for 3-4 days and used to derive ECM scaffolds (FIG. 10).

Generation of EBs and NPC Aggregates

Differentiated EB culture: For spontaneous EB formation, $1\times10^6$ ESCs were seeded in ULA 6-well plates in 3 mL of differentiation medium. The differentiation medium consists of DMEM supplemented with 10% FBS, 0.1 mM $\beta$-mercaptoethanol, penicillin (100 U/mL), and streptomycin (100 µg/mL). The EBs were cultivated for 3-4 days and used to derive ECM scaffolds (FIG. 10).

ESC-derived NPC aggregates: Neural progenitor cell (NPC) aggregates were derived as previously described [56]. Briefly, ESCs were seeded at $1\times10^6$ cells into ULA 6-well plates in 3 mL of DMEM-F12 plus 2% B-27® serum-free supplement (Invitrogen). The formed aggregates were cultivated for 4 days and the medium was replaced at day 2. At day 4, all-trans retinoic acid (RA) (Sigma-Aldrich, St. Louis, Mich.) was supplemented in the medium at 1 µM to enrich neural lineage. The cells were cultivated for additional 4 days and the resulting NPC aggregates were collected to derive ECM scaffolds (FIG. 10).

Decellularization to Generate ECM Scaffolds

All the decellularization reagents were sterilized by membrane filtration prior to the treatment. The decellularization of PSC-derived aggregates was performed as previously described [51]. Briefly, about 600-1000 undifferentiated aggregates, EBs, or NPC aggregates were distributed into each of 1.5 mL microcentrifuge tubes and treated with 1% Triton X-100 (Sigma) for 30 min. After the treatment, the samples were spun down at 18,000 g for 2 min, rinsed twice with phosphate buffered saline (PBS), and incubated with 2,000 unit/mL DNAse I (Sigma) for 30 min. The samples were centrifuged at 18,000 g for 2 min and rinsed twice with PBS prior to characterization or crosslinking.

Crosslinking of ECM Scaffolds

ECM scaffolds were crosslinked using genipin or glutataldehyde in order to increase the stability [52]. For crosslinking, decellularized ECMs from undifferentiated aggregates (DE-A), EBs (DE-E), and NPC aggregates (DE-N) were incubated with 3% genipin (Wako) or 3% glutaraldehyde (Fisher scientific) for 6 hours. Genipin, a natural crosslinking reagent, was reported to have low cytotoxicity compared to chemical reagent glutaraldehyde[57]. Consistent with the literature, genipin-crosslinked ECM scaffolds displayed blue color [52,57]. The ECM scaffolds crosslinked with genipin (G) were referred as DE-AG, DE-EG, and DE-NG. Similarly, the ECM scaffolds crosslinked with glutaraldehyde (GL) included DE-AGL, DE-EGL, and DE-NGL. All the crosslinked ECM scaffolds were rinsed six times in PBS prior to characterizations or re-seeding with ESC-derived NPCs. The non-crosslinked ECM scaffolds, including DE-AC, DE-EC, and DE-NC, were used as the corresponding controls (FIG. 10).

Stability Assay of ECM Scaffolds

The crosslinked or non-crosslinked ECM scaffolds were incubated with 100 µg/mL collagenase solution (Life Technologies) for 2, 4, or 6 hours. The morphology of ECM scaffolds was imaged under light microscope. The remaining ECM scaffolds after collagenase treatment were centrifuged at 800 g for 5 min, and then solubilized by sonication. The protein contents were then assessed by the Bradford protein assay (Bio-Rad) according to the manufacturer's instructions. The absorbance at 595 nm was read on a microplate reader (Bio-Rad). The remaining protein contents were normalized to the amount of proteins before the collagenase treatment which indicated the stability of ECM scaffolds.

Scanning Electron Microscopy (SEM)

For SEM, the crosslinked or non-crosslinked ECM scaffolds were washed with PBS, fixed in 2.5% glutaraldehyde for 30-60 min and dehydrated in graded ethanol solutions. The samples were dried by hexamethyldisilazane (HMDS) evaporation, mounted, and sputter-coated with iridium. Observations were made using a Nova 400 Nano SEM (FEI, Hillsboro, Oreg.) under low-vacuum conditions.

Atomic Force Microscopy (AFM)

For AFM analysis, samples were drop cast and dried on glass substrates, and their elastic modulus and surface roughness were subsequently measured by a Bruker Icon AFM (Digital Instruments, Santa Barbara, Calif.) using the PeakForce QNM (quantitative nano-mechanical measurement) mode. Force curves were taken at 2 kHz with an amplitude of 100-150 nm at each point on the sample and were subsequently analyzed to ascertain modulus, adhesion and other mechanical properties. Various probes were used in different regimes of elastic modulus according to their spring constant: Bruker ScanAsyst Air (up to ~20 MPa), RTESPA (0.2 to 2.0 GPa), and TAP525 (1 to 2 GPa). These probes were fully calibrated using clean sapphire for deflection sensitivity, thermal tuning to estimate spring constant, and a tip qualification standard to ascertain tip radius and thus contact area. QNM information including modulus, deformation, adhesion and dissipation were obtained and directly compared to sample morphology.

NPC Reseeding and Cultivation on the Decellularized ECMs

For various ECM scaffolds, $1 \times 10^6$ dissociated NPCs or intact NPC aggregates derived from ESCs were reseeded on the ECM scaffolds and cultivated for 3-4 days in DMEM-F12 containing 2% B27. The cells were analyzed for colonization on the scaffolds, proliferation, and viability. To study the effect of retinoid signaling, BMS 493 (1 µM, Santa Cruz), a pan-retinoic acid receptor (RAR) antagonist, was supplemented in the media for some experiments.

Cell colonization assay: NPC-ECM constructs were stained with 1 µM calcein AM (Molecular Probes) and imaged under a fluorescent microscope (Olympus IX70, Melville, N.Y.). The percentage of ECM scaffolds that were colonized with NPCs was assessed by dividing the number of scaffolds in contact with PSCs against the total number of scaffolds. The size distributions of NPC aggregates and ECM scaffolds were also analyzed by ImageJ software.

Cell proliferation assays: Cell numbers were determined at days 3 using a hemocytometer after trypsin/EDTA dissociation for fold expansion. Cell proliferation kinetics was also determined by incubating with 5 mg/mL 3-(4,5-Dimethylthiazol-2-yl)-2,5-diphenyltetrazolium bromide (MTT, Sigma) solution. Afterwards, the formazan crystals were hydrolyzed with dimethyl sulfoxide (Sigma) and measured at 500 nm using a microplate reader.

Cell viability assay: The cells were incubated in DMEM containing 1 µM calcein AM for 30 min. The samples were then washed and imaged under a fluorescent microscope. Based on the analysis from ImageJ software, the viability was calculated by dividing the total green intensity (live cells) by the total aggregate area (total cells).

Immunocytochemistry

After 3 days of culture in suspension, the NPC-ECM constructs were replated in 24-well plates coated with Geltrex™, the LDEV-Free Reduced Growth Factor Basement Membrane Matrix (Life Technologies), for another 3 days. The differentiation was assessed by immunocytochemistry for neural markers. Briefly, the cells were fixed with 4% paraformaldehyde (PFA) and permeabilized with 0.2-0.5% Triton X-100. The samples were then blocked and incubated with mouse or rabbit primary antibody against: Nestin (Sigma) or Musashi-1 (Abcam) for neural progenitors, β-tubulin III (Millipore) for neurons, or GFAP (Millipore) for astrocytes. After washing, the cells were incubated with the corresponding secondary antibody: Alexa Fluor® 488 goat anti-Mouse IgG1 for GFAP and β-tubulin III, or Alexa Fluor® 488 goat anti-Rabbit IgG for Nestin and Musashi-1 (Molecular Probes). The samples were mounted with 4',6-Diamidino-2-Phenylindole (DAPI) and visualized using a fluorescent microscope.

Flow Cytometry

To quantify the levels of neural marker expression, the cells on ECM scaffolds were harvested by trypsinization and analyzed by flow cytometry [51]. Briefly, 1×10⁶ cells per sample were fixed with 4% PFA and washed with staining buffer (2% FBS in PBS). The cells were permeabilized with 100% cold methanol, blocked, and then incubated with primary antibodies against Nestin, β-tubulin III, GFAP, or Musashi-1 followed by the corresponding secondary antibody: Alexa Fluor® 488 goat anti-Mouse IgG1 (for GFAP and β-tubulin III) or Alexa Fluor® 488 goat anti-Rabbit IgG (for Nestin and Musashi-1). The cells were acquired with BD FACSCanto™ II flow cytometer (Becton Dickinson) and analyzed against isotype controls using FlowJo software.

Statistical Analysis

Each experiment was carried out three times. The average values of two or three independent experiments were presented and the results are expressed as [mean±mean absolute deviation (MD)]. In each experiment, triplicate samples were used. To assess the statistical significance, ANOVA followed by Fisher's LSD post hoc tests or t-tests were performed. A $p$-value<0.05 was considered statistically significant.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 7

Derivation and Characterization of Decellularized ECM Scaffolds

Figure 11A:
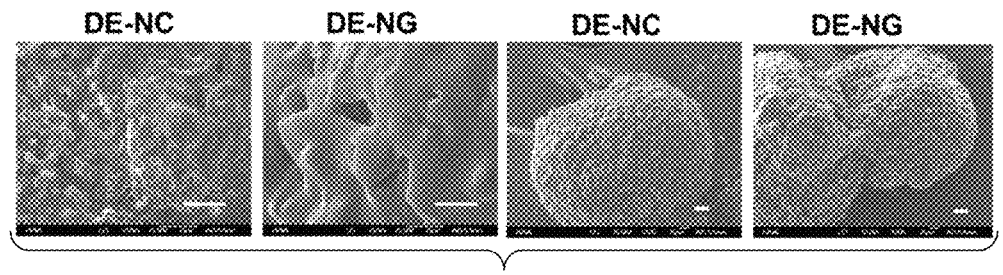
FIGS. 11A-11E. Ultrastructure and mechanical properties of non-crosslinked and crosslinked ECM scaffolds.
Figure 11B:
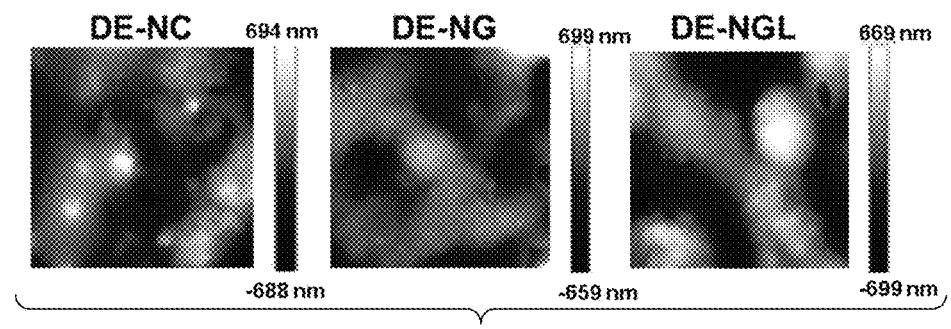
Figure 11C:
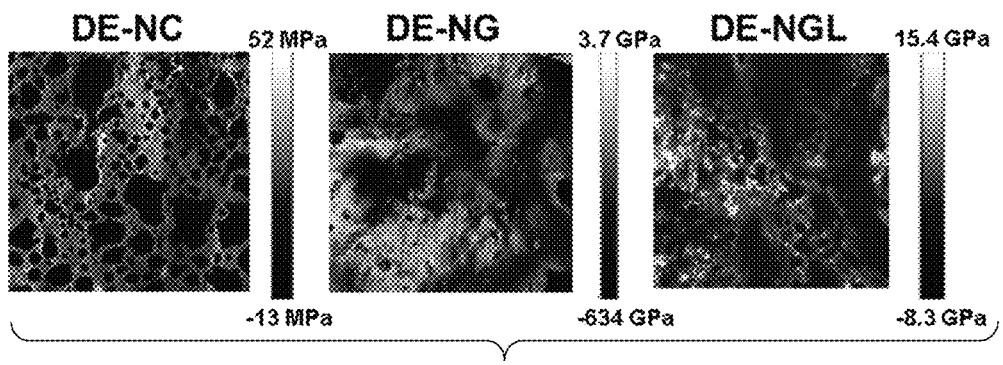
Figure 11D:
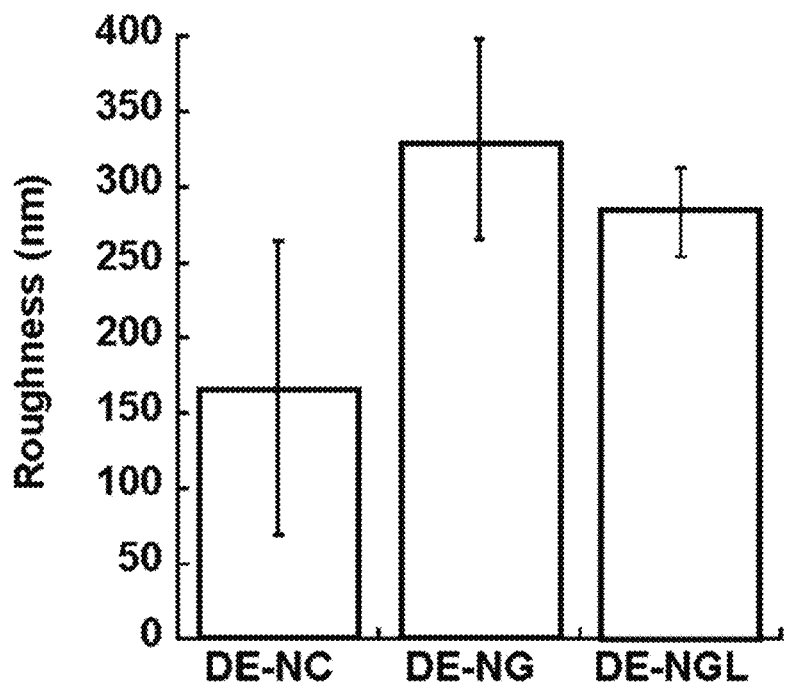
Figure 11E:
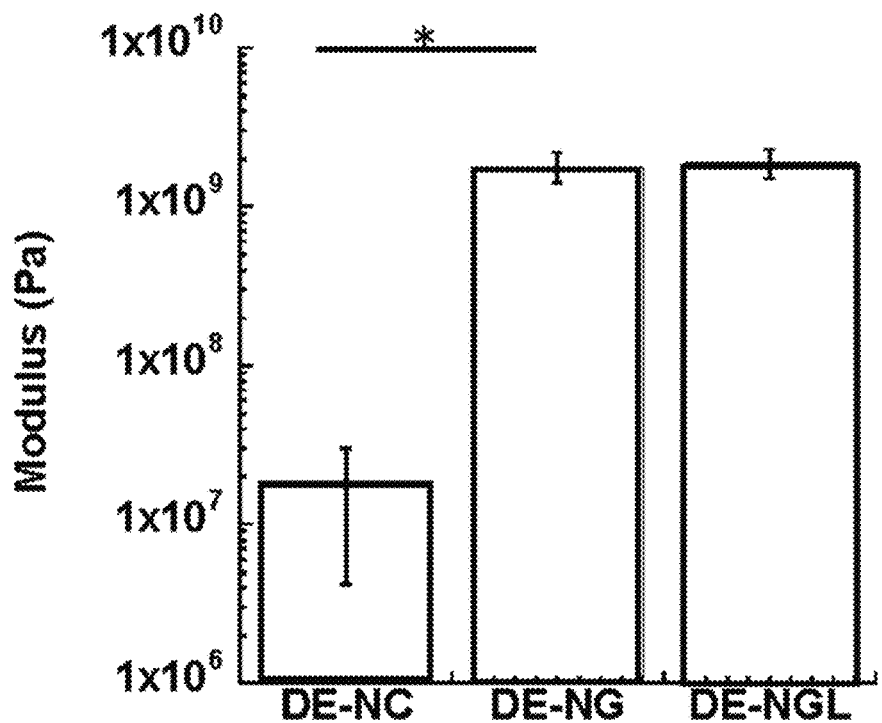
Figure 12A:
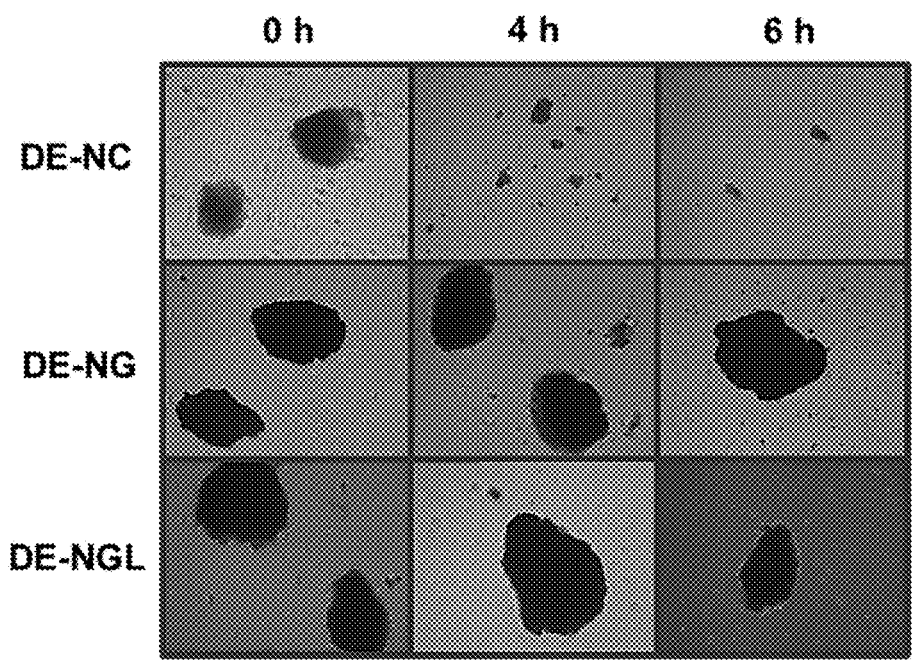
FIGS. 12A and 12B. Crosslinking enhanced the stability of ECM scaffolds. DE-NC, DE-NG and DE-NGL were treated with collagenase for 2, 4, and 6 hours.
Figure 12B:
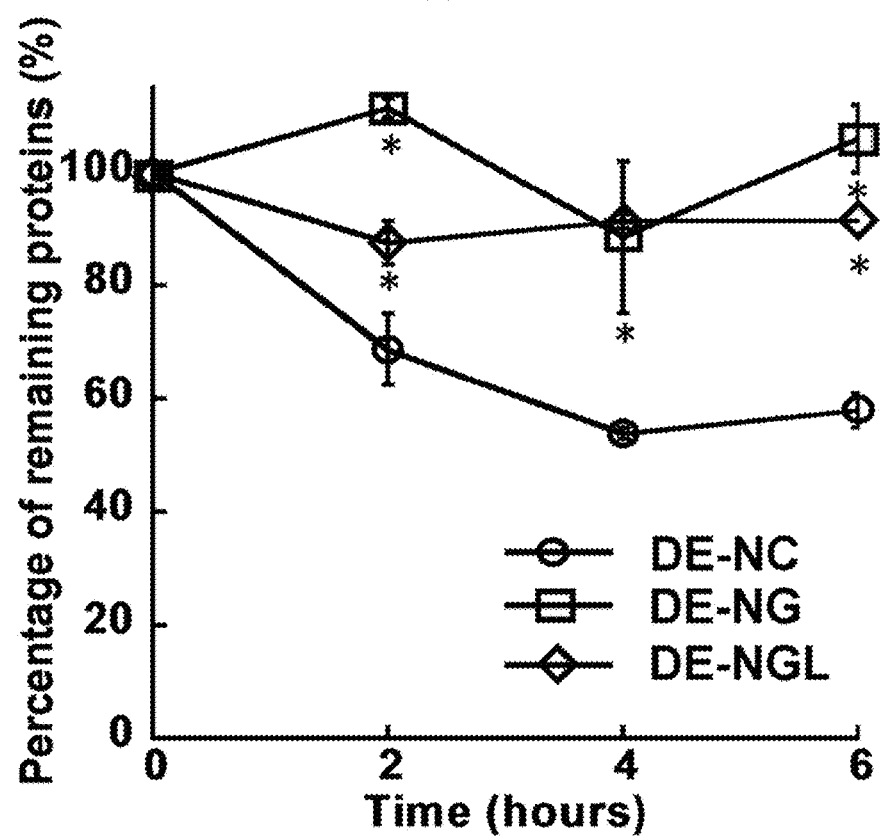

The ultrastructure analysis of ECM scaffolds revealed changes in the morphology upon crosslinking treatment. The genipin-treated scaffolds showed smoother topography compared to non-crosslinked scaffolds which displayed a more porous structure by SEM analysis (FIG. 11A). The roughness was comparable for the crosslinked and non-crosslinked scaffolds: i.e., 250-300 nm for DE-NC, DE-NG, and DE-NGL (FIGS. 11B and 11D). The mechanical properties of the decellularized ECMs were also changed upon crosslinking analyzed by AFM. The elastic modulus was increased by crosslinking compared to non-crosslinked ECM scaffolds (1.8 GPa vs. 17 MPa in average when measured at dry state) (FIGS. 11C and 11D). In addition, the stability of crosslinked scaffolds compared to non-crosslinked scaffolds was measured upon collagenase treatment using the DE-N scaffolds as the test samples. Stable scaffold size was observed for DE-NG and DE-NGL while the size of DE-NC decreased with treatment time (FIG. 12A). Consistently, the remaining protein contents after collagenase treatment were around 100% for DE-NG and 90% for DE-NGL, while the protein content decreased to 55% for DE-NC (FIG. 12B). Together, the crosslinking increased elastic modulus and the structural stability of decellularized ECM scaffolds.

EXAMPLE 8

Effects of the Decellularized ECMs on NPC Colonization and Proliferation

Figure 13A:
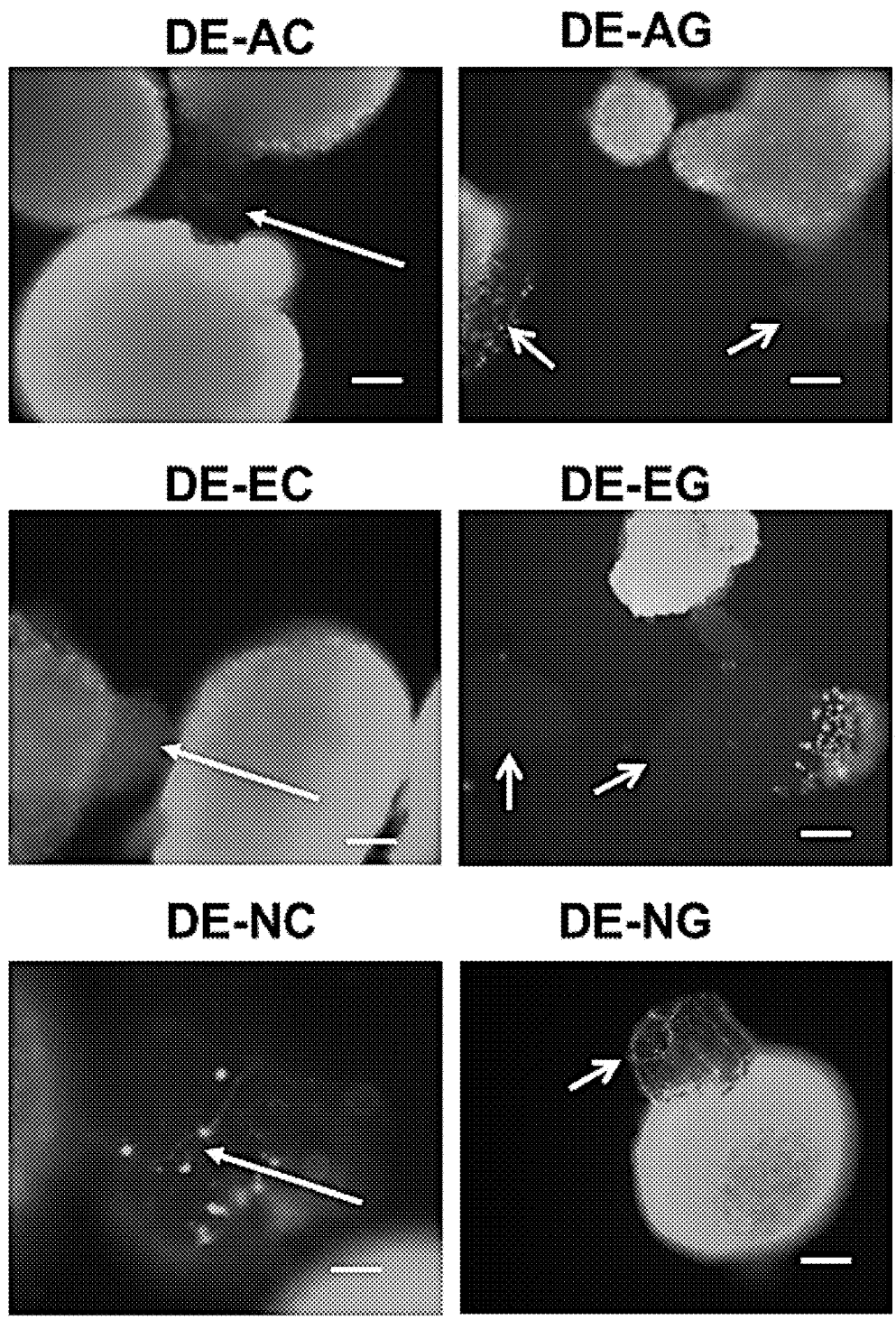
FIGS. 13A-13C. Morphology and colonization of reseeded ESC-NPCs on crosslinked and non-crosslinked ECM scaffolds.
Figure 13B:
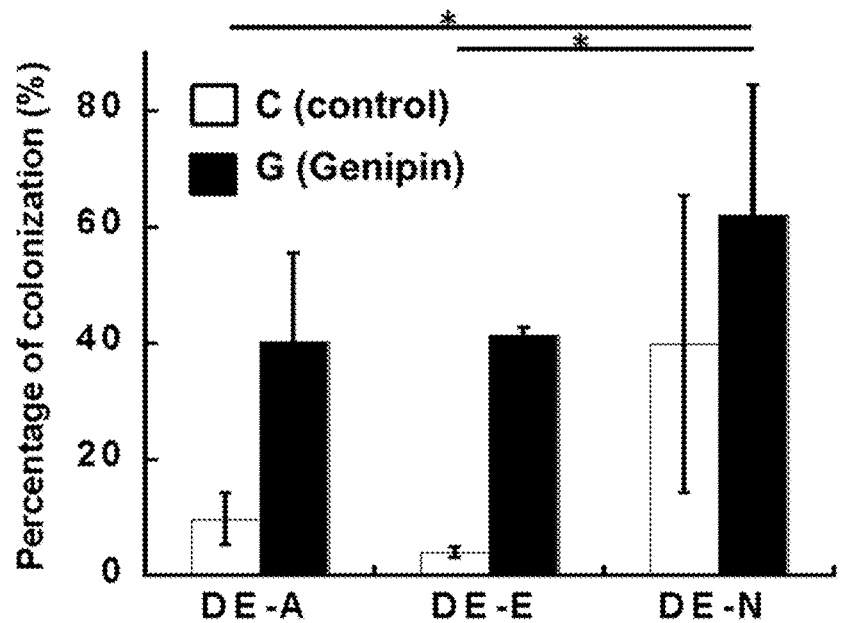
Figure 13C:
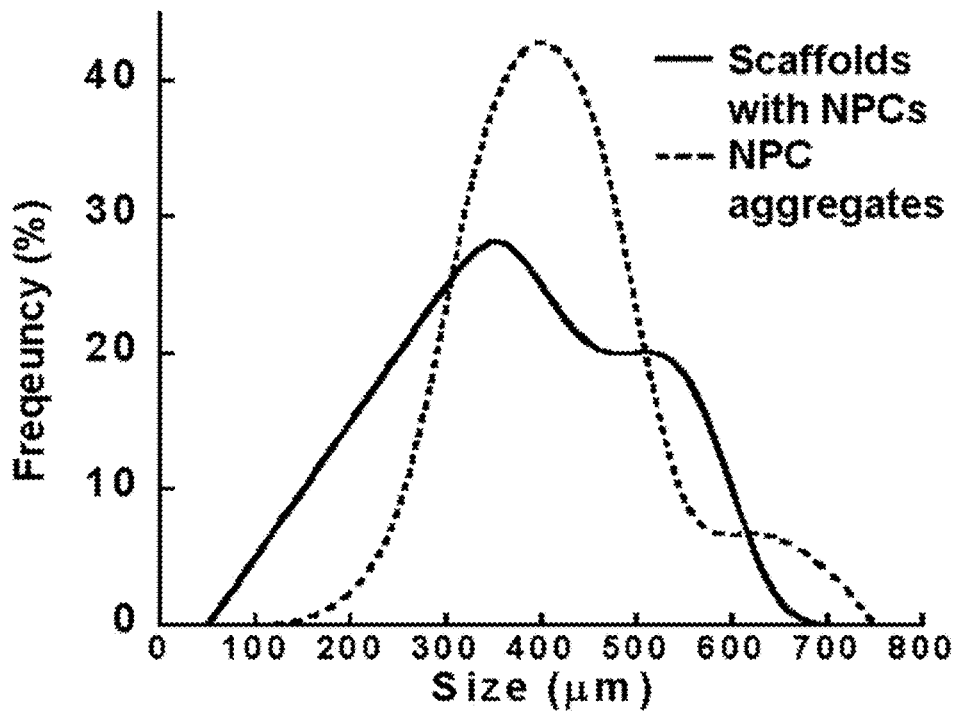

The decellularized ECM scaffolds were seeded with intact neural progenitor cells (NPC) aggregates which had comparable size to the ECM scaffolds. The colonization of ECM scaffolds with NPC aggregates was studied. NPC aggregates contacting ECM scaffolds were able to bridge with the ECM scaffolds and some cells migrated and grew on the ECMs, especially for genipin-treated scaffolds (FIG. 13A). The crosslinking treatment by genipin was found to increase the percentage of scaffolds seeded with NPC aggregates compared to non-crosslinked scaffolds (40-60% vs. 5-30%) (FIG. 13B). The majority of the colonized ECM scaffolds showed a similar size range as NPC aggregates (i.e., about 400 μm) (FIG. 13C).

Figure 14A:
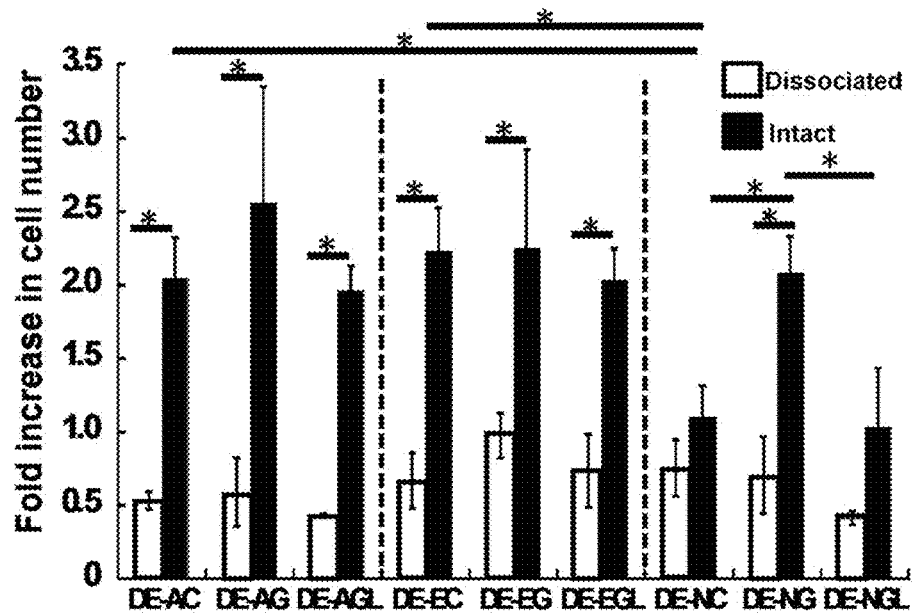
FIGS. 14A-14D. Proliferation and viability of reseeded ESC-NPCs on ECM scaffolds.
Figure 14B:
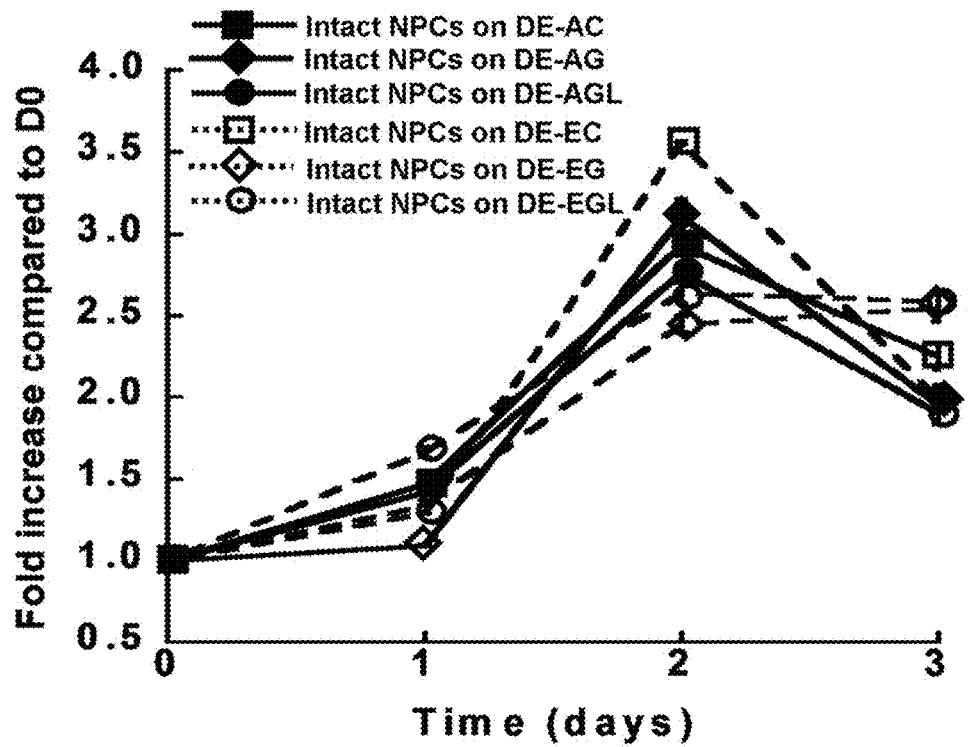
Figure 14C:
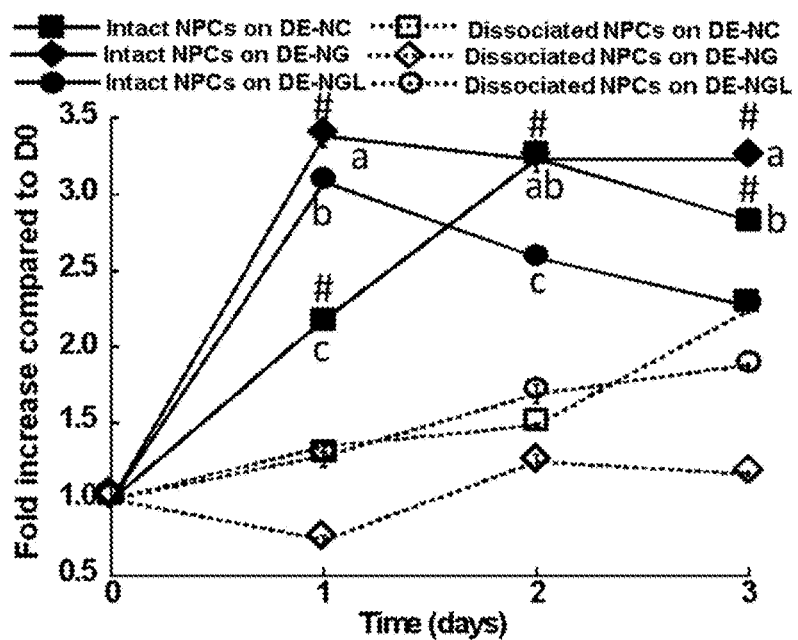
Figure 14D:
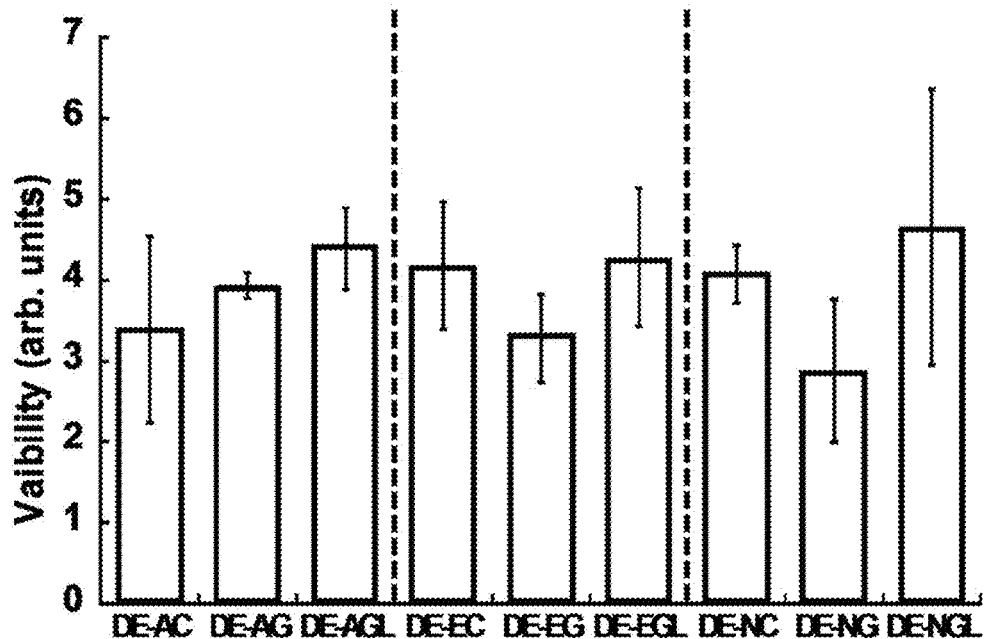
Figure 15A:
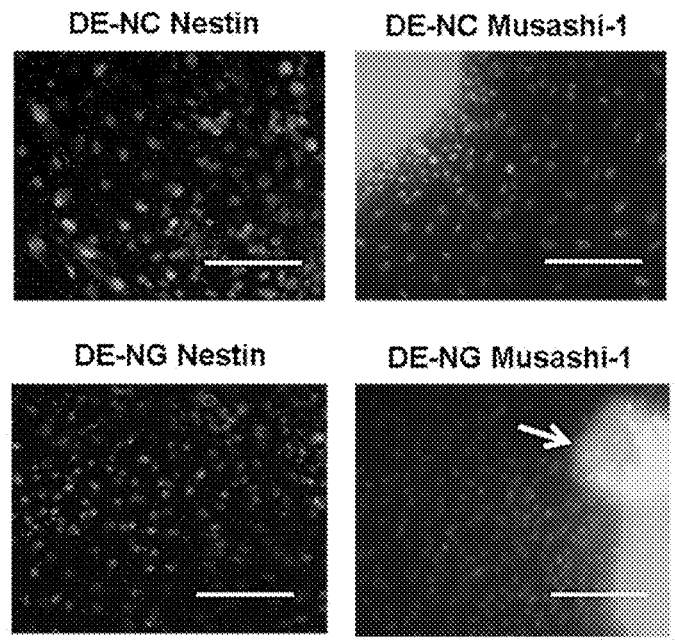
FIGS. 15A-15D. Expression of progenitor markers of the reseeded ESC-NPCs grown on ECM scaffolds. Representative fluorescence images (FIG. 15A) and flow cytometry histograms (FIG. 15B) of Nestin and Musashi 1 expressions. The white arrow indicated the crosslinked ECM scaffold, which exhibited red auto fluorescence.
Figure 15B:
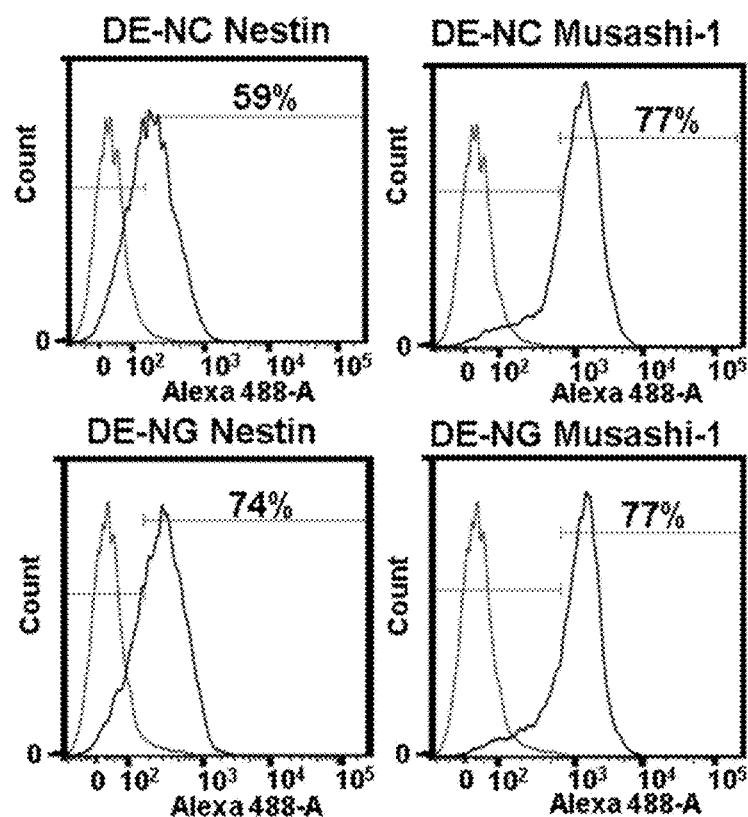
Figure 15C:
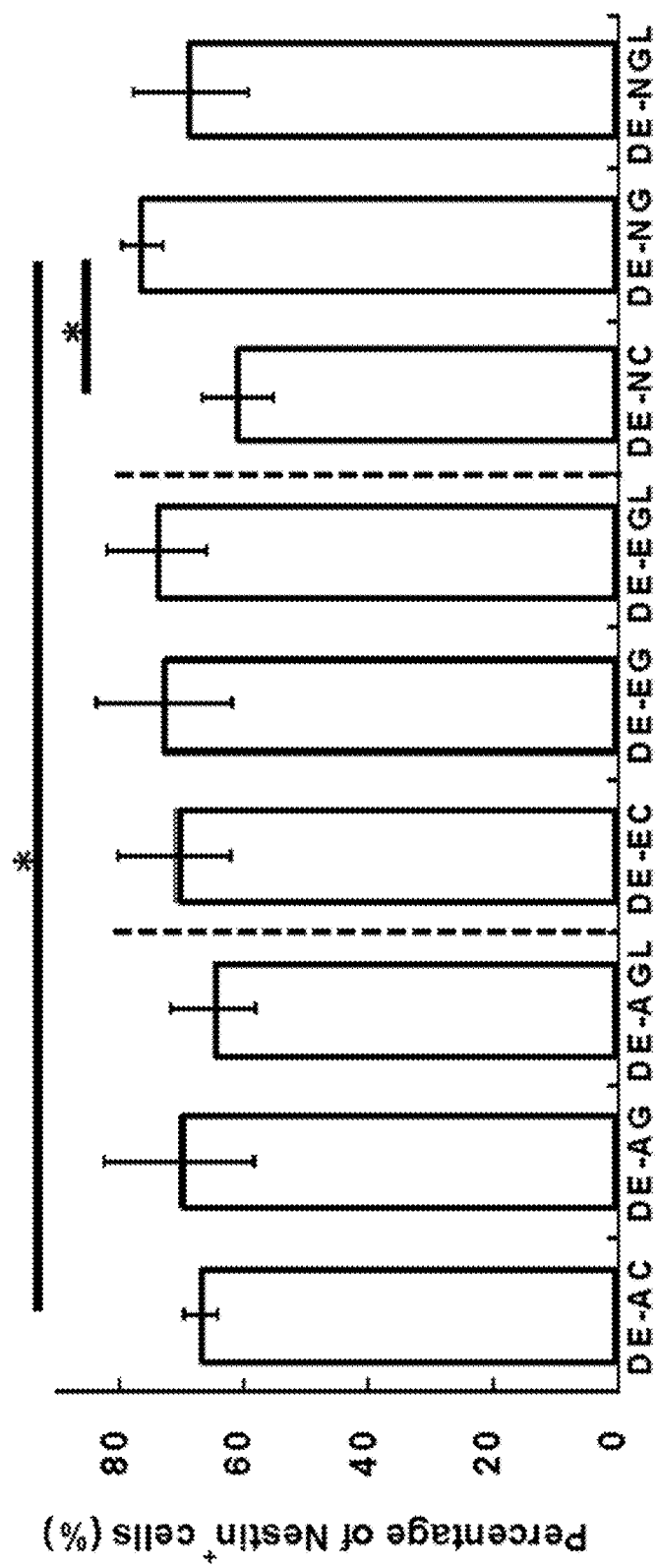
Figure 15D:
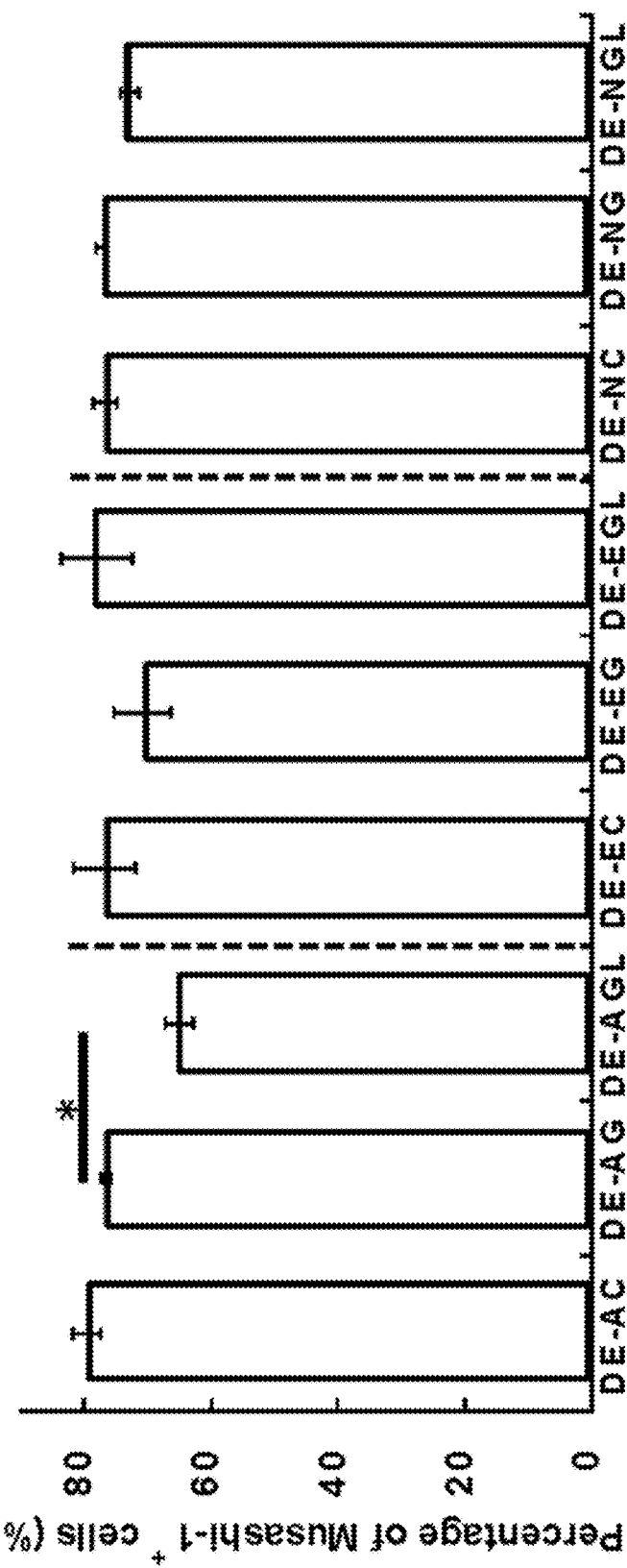

The cell proliferation was evaluated for all the scaffolds seeded by dissociated NPCs or intact NPC aggregates. Dissociated NPCs showed significantly lower expansion fold than intact NPC aggregates (0.5-1.0 vs. 1.2-2.5) for all the scaffolds (FIG. 14A). No significant difference was observed for crosslinked or non-crosslinked scaffolds in DE-A or DE-E group. The NPC aggregates reseeded on DE-NC and DE-NGL scaffolds had significantly lower expansion fold compared to other scaffolds (1.0 fold vs. 2.0-2.2 folds). However, DE-NG supported higher cell expansion fold than DE-NC and DE-NGL, which was comparable to DE-A and DE-E scaffolds (about 2.0 folds). MTT assays for DE-A and DE-E scaffolds showed no significant difference for crosslinked or non-crosslinked scaffolds, similar to the observation for expansion fold (FIG. 14B). Consistently, cells in DE-NG group had higher MTT activity compared to DE-NC and DE-NGL groups (FIG. 14C). Again, lower MTT activity was observed for dissociated NPCs compared to intact NPC aggregates. Hence, intact NPC aggregates were chosen for the following experiments. There was no significant differences in cell viability for all the scaffolds (FIG. 14D), indicating the low level of cytotoxicity of crosslinked ECM scaffolds.

EXAMPLE 9

Effect of Decellularized ECM Scaffolds on Neural Differentiation

Figure 16A:
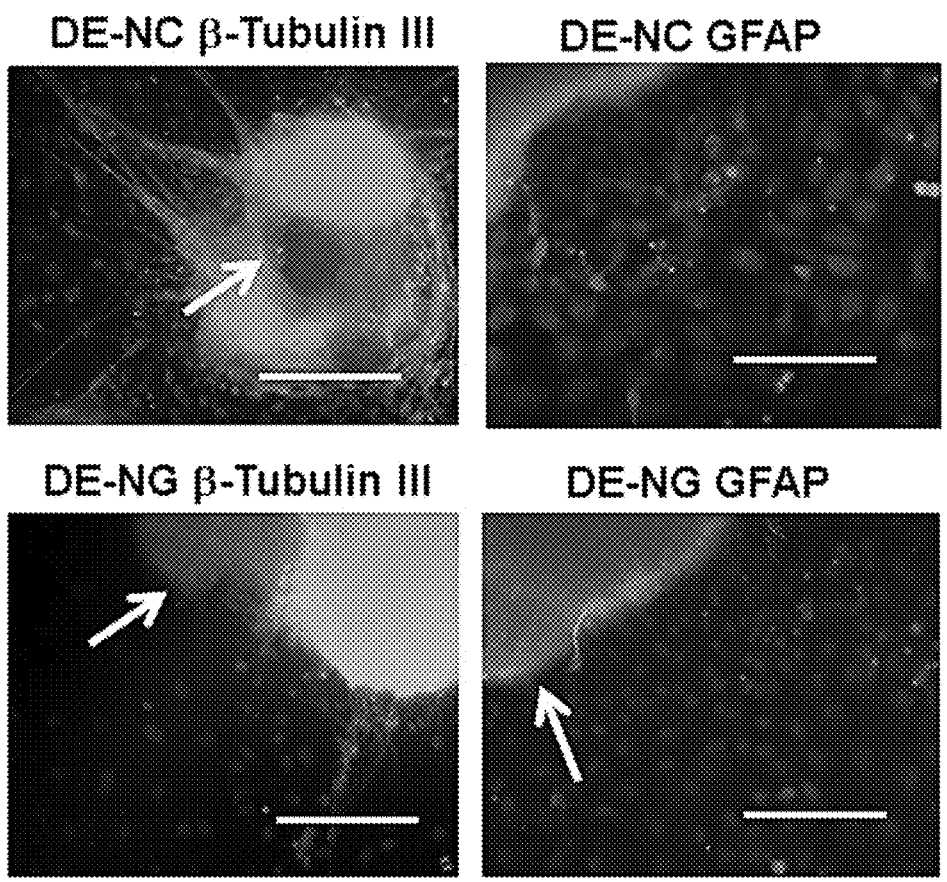
FIGS. 16A-16D. Neural differentiation of the reseeded ESC-NPCs grown on ECM scaffolds. Representative fluorescence images (FIG. 16A) and flow cytometry histograms (FIG. 16B) of β-tubulin III and GFAP expressions. The white arrows indicated the crosslinked ECM scaffold, which exhibited red auto fluorescence.
Figure 16B:
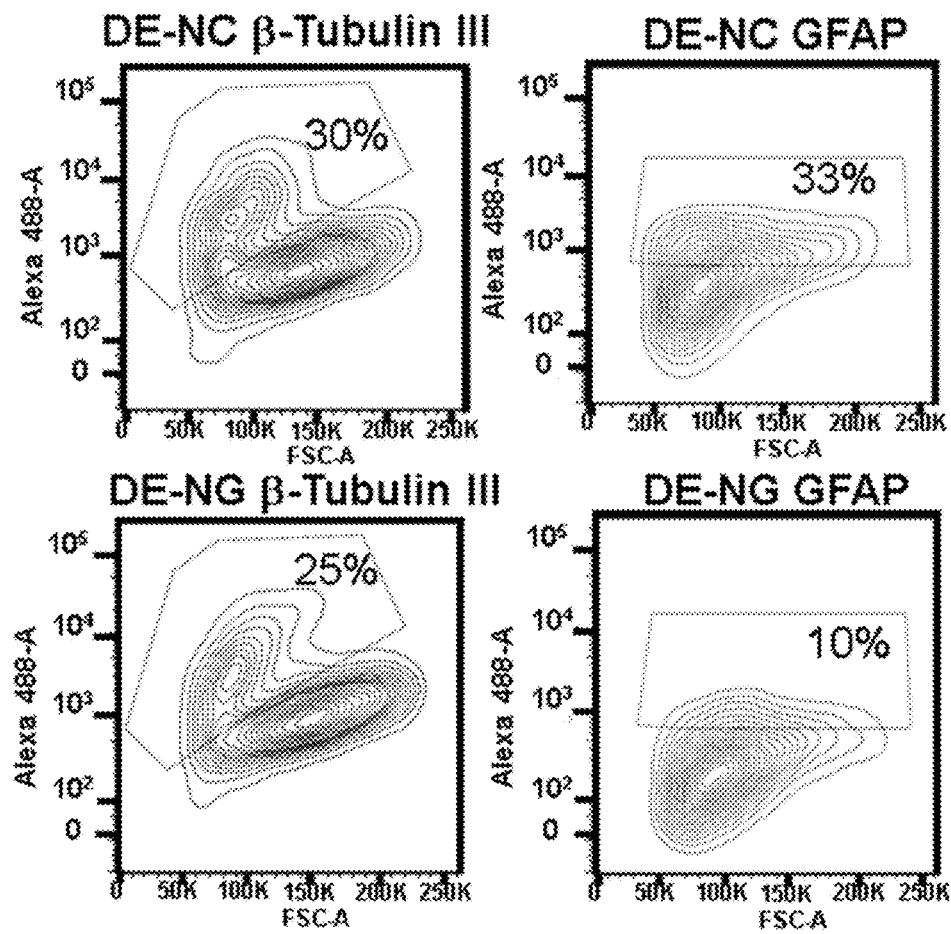
Figure 16C:
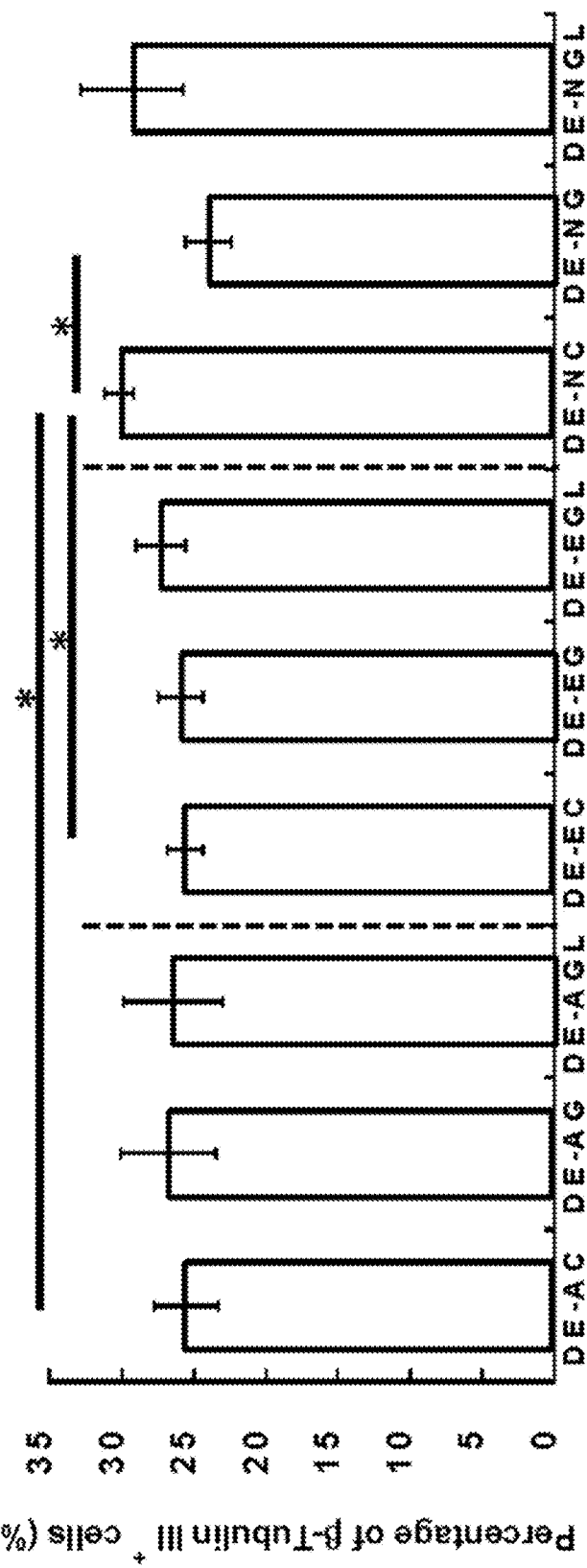
Figure 16D:
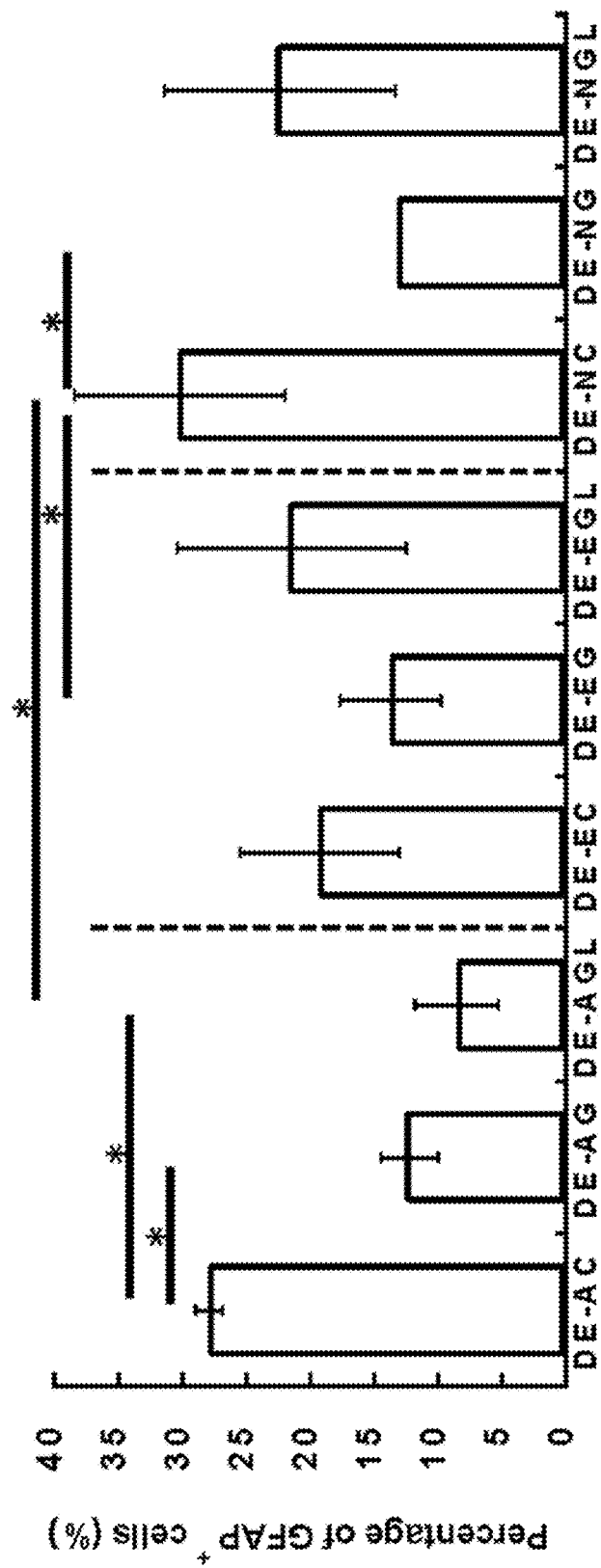
Figure 17A:
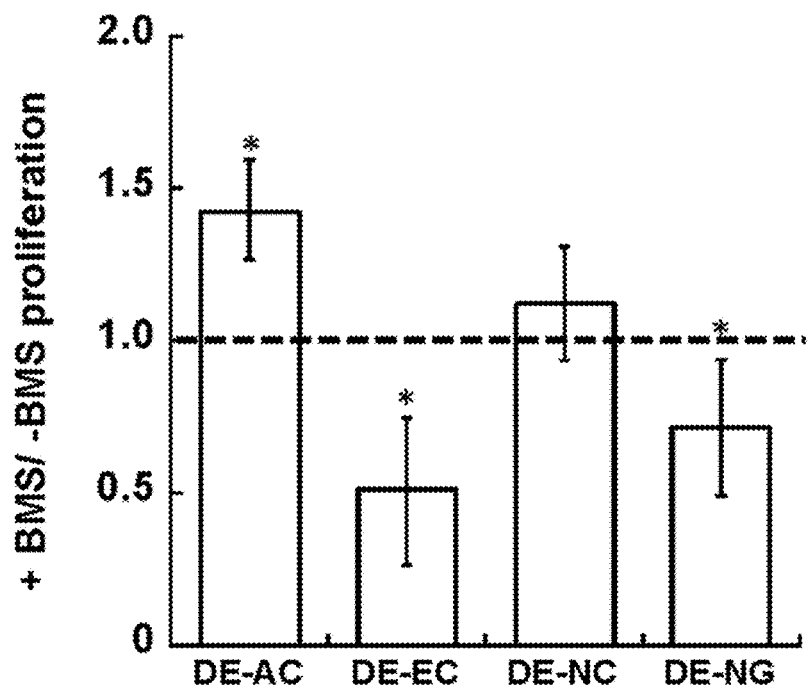
FIGS. 17A-17D. Effect of BMS 493 treatment for cells grown on ECM scaffolds.
Figure 17B:
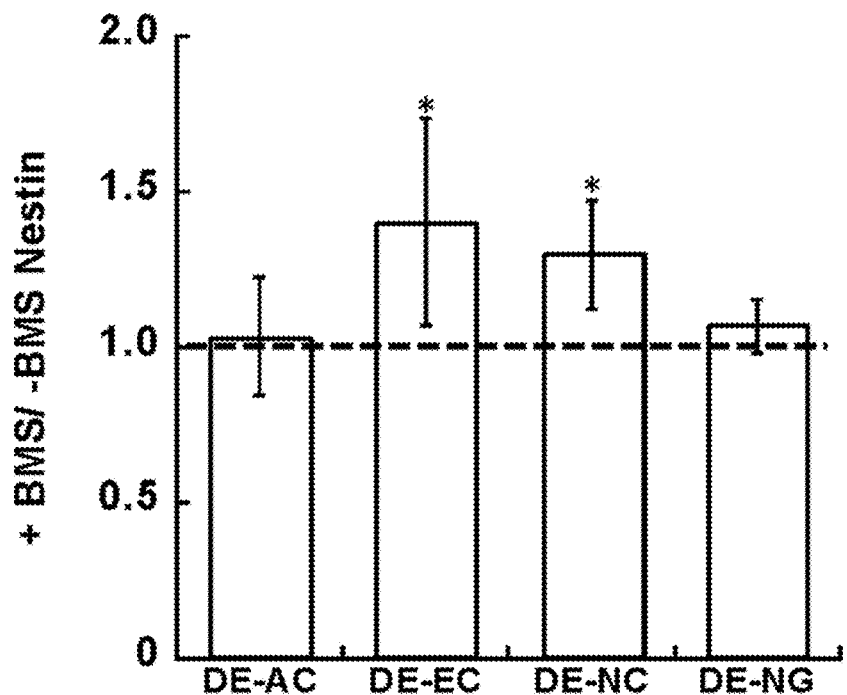
Figure 17C:
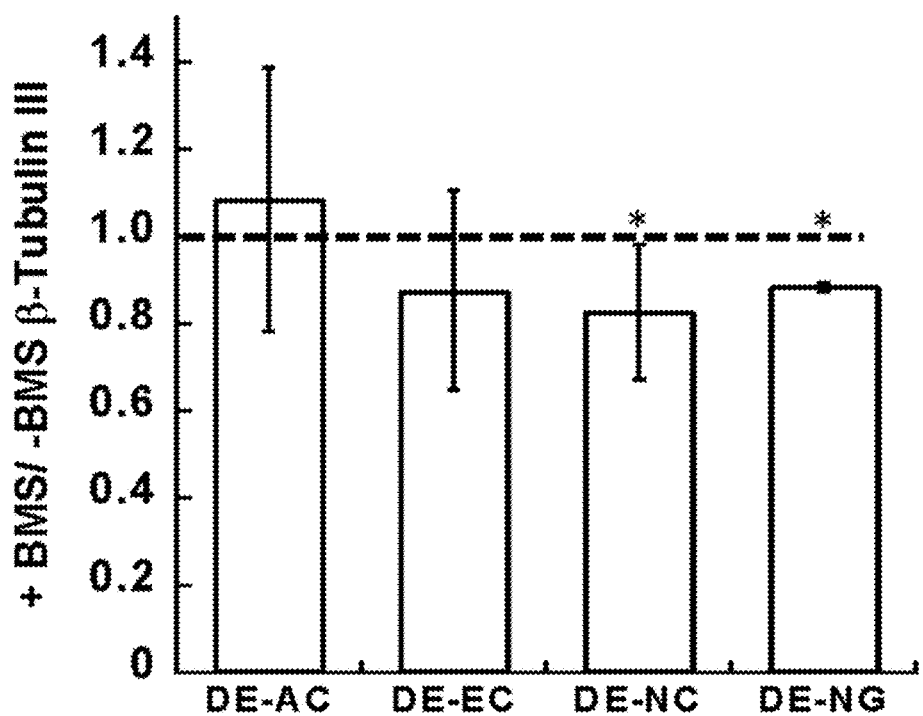
Figure 17D:
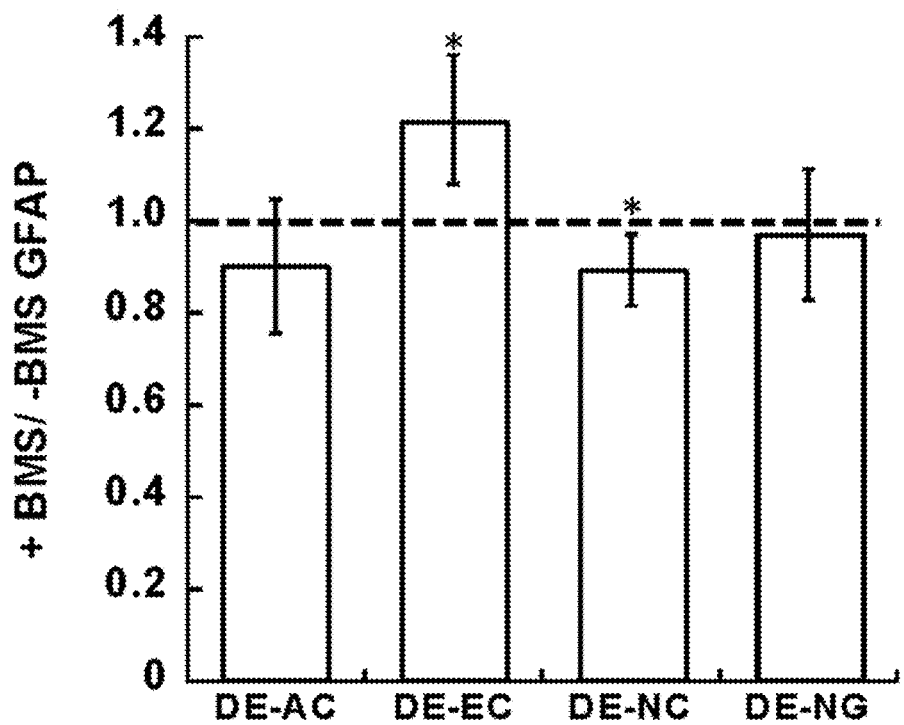

The expressions of neural progenitor markers, Nestin and Musashi-1, were assessed for NPCs grown on all the scaffolds (FIG. 15). Nestin expressions were comparable for cells from the crosslinked or non-crosslinked scaffolds in DE-A and DE-E groups. However, for DE-N groups, DE-NC showed lower Nestin expression (61% vs. 70%) compared to DE-NG while the difference from DE-NGL was not significant (FIGS. 15A-15C). The Musashi-1 expression was comparable for all DE-N scaffolds (FIG. 15D). DE-AGL showed slightly lower Musash-1 expression compared to DE-AC and DE-AG. Conversely, β-Tubulin III expressions (marker for neurons) were comparable for cells from the crosslinked or non-crosslinked scaffolds in DE-A and DE-E groups, while DE-NC showed higher β-Tubulin III expression (30% v.s. 23%) compared to DE-NG (FIG. 16). Consistently, GFAP expression (marker for astrocytes) was enhanced on DE-NC compared to DE-NG (30% v.s. 12%) (FIG. 16D). In general, genipin-treated scaffolds (DE-AG, DE-EG, and DE-NG) showed lower GFAP expression compared to the non-crosslinked controls (DE-AC, DE-EC, and DE-NC) (13-15% v.s. 25-30%) (FIG. 16D). Thus, DE-NC enhanced neural differentiation with lower Nestin and higher β-Tubulin III expression compared to the scaffolds in DE-A and DE-E groups. Moreover, the crosslinking of DE-N scaffolds with genipin (i.e., DE-NG group) supported higher Nestin and lower β-Tubulin III expression. The ratios of β-Tubulin III positive cells to GFAP positive cells were calculated (Table 3) and genipin-crosslinked scaffolds increased the ratio of α-Tubulin III to GFAP compared to non-crosslinked scaffolds. The crosslinking effects on neural differentiation, however, were not significant for glutaraldehyde (except DE-AGL for Musashi-1 and GFAP).

EXAMPLE 10

Effects of RA-RAR Signaling

The DE-N scaffolds, derived from NPC aggregates through RA treatment, were more responsive to genipin-crosslinking Therefore, the effect of RA-RAR signaling was investigated for DE-NC and DE-NG scaffolds with DE-AC and DE-EC as controls (FIG. 17). The timing of RA induction and RA concentration play a key role in the regulation of NPC fate [58,59]. To interrogate the contribution of RA-RAR signaling, the plus/minus (+/−) effects of BMS 493 were assessed. BMS 493 is a pan RAR antagonist that blocks RA-RAR interaction. It was observed that NPC treatment with BMS 493 reduced the cell proliferation on DE-EC and DE-NG scaffolds (FIG. 17A). The expression of progenitor marker Nestin was increased upon BMS 493 treatment for DE-EC and DE-NC conditions (FIG. 17B). Consistently, the increased Nestin expression was associated with the significant decrease in β-Tubulin III (neuron marker) and GFAP (astrocyte marker) expressions in cells from DE-NC scaffold (FIGS. 17C and 17D). BMS 493 treatment also increased GFAP expression for DE-EC condition (FIG. 17D). Together, these results indicated that the inhibition of RA-RAR signaling differentially modulated the behavior of NPCs on various types of scaffolds. RA-RAR signaling may contribute to the enhanced neuronal and glial differentiation on DE-NC.

EXAMPLE 11

The Crosslinking of Decellularized ECM Scaffolds Modulated Neural Differentiation The crosslinking increased the stability of ECM scaffolds and also increased the elastic modulus, which may affect cell seeding and colonization. The decellularized ECMs from PSC aggregates showed Young's modulus in the range of reported values (~MPa) for various types of decellularized tissues (Table 4) [60-65]. After crosslinking, the elastic modulus was increased to the level similar to polystyrene tissue culture surface (about 2-3 GPa) [66,67]. The high modulus in crosslinked and non-crosslinked ECM scaffolds may be due to the AFM measurement at dry state of the scaffolds, which led to significantly higher value compared to wet state [68]. The dry or wet state, however, does not affect the relative difference in stiffness for crosslinked and non-crosslinked ECM scaffolds. The crosslinking may regulate NPC colonization following the differential interfacial tension hypothesis [69,70]. Soft surface, like neurospheres, tend to envelop harder surface such as the crosslinked scaffolds [69]. When two surfaces displayed similar modulus, the covering of a surface by another surface occurred less efficiently [69]. Crosslinking decellularized ECMs increased the stiffness of the scaffolds [71]. So the cells from NPC aggregates (soft) had higher tendency to envelop crosslinked ECMs (hard) compared to non-crosslinked ECMs (soft), which may support the observation in this study that genipin-crosslinking enhanced the reseeded NPC colonization.

The crosslinking of ECM scaffolds may affect neural differentiation of PSC-derived NPCs due to the increased elastic modulus [72]. While neural differentiation was enhanced for soft materials (1 kPa-7 kPa), the elastic modulus of hard substrate ranging from 10 kPa to 1 GPa (i.e. the modulus for polystyrene coated with laminin) altered NPC differentiation to a lesser extent [53-55]. The DE-NG (higher modulus) slightly decreased the percentages of neuronal (by 6%) and glial (by 15%) cells with higher percentage of Nestin positive cells (by 15%) compared to DE-NC (lower modulus) in the present study. Moreover, the elastic modulus could regulate NPC fate as a function of culture configuration and differentiation medium. NPCs encapsulated in alginate hydrogel showed a gradual decrease of neuronal and glial differentiation when increasing the modulus [73]. In the neuronal differentiation medium, increasing surface modulus from 1 kPa to 1 GPa did not affect the percentage of neuronal cells (i.e. β-Tubulin III+) [74], while glial cell purity was lowered [54]. Under the mixed differentiation conditions (i.e. induce both neuronal and glial cells), stiff surfaces (i.e. 1 GPa) decreased the percentage of neuronal cells while enhancing GFAP positive cells through the regulation of Rho GTPases [54, 55,75]. In the present study, the retinol of B27 medium served as source of RA and the differentiation medium was more neuronal [76]. Consistently, the increase of scaffold stiffness via crosslinking for DE-A and DE-E scaffolds did not affect β-Tubulin III positive cells, but decreased the percentage of GFAP positive cells.

Together, the increased modulus through crosslinking on decellularized PSC-ECM scaffolds enriched the proportion of neurons over astrocytes (Table 3). ECM crosslinking did not affect NPC proliferation and the neuronal differentiation potential for DE-A and DE-E scaffolds. However, the crosslinking with genipin for DE-NG scaffolds changed structure and biomechanical properties, leading to the higher Nestin expression and lower β-Tubulin III and GFAP expressions compared to DE-NC scaffolds. The effect of glutaraldehyde, however, was less pronounced. As genipin is a natural crosslinking reagent compared to chemical agent glutaraldehyde[67], crosslinking with genipin is a preferred method.

The Aggregate Properties Prior to ECM Decellularization Modulated Neural Differentiation PSC-derived NPC aggregates are composed of heterogeneous neural cell populations which may contain a mixture of primitive and definitive NPCs [77,78]. Primitive PSC-NPCs (mimicking neural precursor at E5.5-E7.5 of embryonic development) are LIF-dependent [79] and prone to endogenous RA mediated apoptosis [80]. In contrast, definitive NPCs generated from PSCs displayed features of adult NPCs and showed higher neuronal and glial differentiation compared to primitive NPCs [81]. The heterogeneous NPC aggregates in the present study may be regulated by different PSC-derived ECM scaffolds to elicit the differential response in proliferation and neural differentiation.

The present study showed specific intrinsic cues from the three types of ECM scaffolds, i.e. DE-A, DE-E, and DE-N, to regulate the reseeded NPC behaviors. DE-NC supported higher β-Tubulin III and GFAP positive cells and was more responsive to genipin-crosslinking effects compared to DE-AC and DE-EC. Our previous study indicated the possible retinoid signaling for ECMs derived from RA-treatment EBs which was similar to DE-N scaffolds [51]. The RA-RAR regulation of NPC commitment emerges as a function of neural cell development [58,82]. For example, RA-RAR interactions have been shown to regulate NPC proliferation and GFAP expression of definitive NPCs through the activation of RARα and RARγ [83]. In the present study, by blocking RA-RAR interactions, different ECM scaffolds showed differential responses in proliferation and neural marker expressions, possibly due to interactions of ECMs with exogenous and/or paracrine and autocrine factors.

DE-AC may bind LIF during the culture of undifferentiated aggregates prior to decellularization [84]. Once blocking the RA-RAR signaling by BMS 493, no changes in neural marker expression was observed for DE-AC group, while the possible LIF bound to DE-AC may cause higher proliferation of primitive NPCs [58]. DE-NC may bind the NPC-secreted factors (i.e., NGF, BDNF, GDNF, FGF2 etc.) which enhanced the neuronal differentiation and the commitment of primitive NPCs to definitive NPCs compared to DE-EC and DE-AC [81,85]. In addition, due to RA-treatment before decellularization, DE-NC may contain higher retinoid signaling than DE-A and DE-E scaffolds, which regulated NPC differentiation towards neuronal and glial lineage [51,86]. By blocking RA-RAR interactions, neuronal and glial differentiations were reduced in DE-NC scaffold. DE-EC may display less biochemical signaling specificity compared to DE-AC and DE-NC, but may have endogenous retinoid signaling [47]. Conversely, the RA-RAR inhibition could favor the survival of more primitive NPCs as indicated by the enhanced Nestin expression. Indeed, Cerberus, a factor secreted by EBs, could bind to DE-EC and support the survival of primitive NPCs [6,79,28]. Finally, NPCs reseeded on DE-NG showed slightly different response to RA-RAR inhibition compared to cells on DE-NC. There was no change in Nestin and GFAP expression but slightly lower proliferation and β-Tubulin III expression. This indicated that the changes of biomechanical properties of ECMs due to cross-linking may affect the interactions with biological molecules, which further impacted the neural cell proliferation and differentiation.

This study indicated that decellularized ECM scaffolds derived from PSC aggregates displayed specific cues regulating the behavior of reseeded ESC-derived NPCs. The crosslinking of ECM scaffolds modulated their structural and biomechanical properties, which enriched the neuronal fraction of differentiated cells over the glial population. The potential binding of endogenous and exogenous neural inductive factors on DE-NC scaffold may promote neuronal and glial differentiation of NPCs compared to DE-AC and DE-EC scaffolds, which may contain different signaling specificity. Thus, the derivation of decellularized ECM scaffolds from different types of PSC aggregates enabled the regulation of neural differentiation of the reseeded cells through the tunable biomechanical and biological properties. The bioactive scaffolds from PSC-derived ECMs are suitable for in vivo transplantation and in vitro cell expansion.

TABLE 3

The ratio of β-Tubulin III+ cells to GFAP+ cells in various ESC scaffolds.

| Scaffolds | Ratio of β-Tubulin III/GFAP |
| --- | --- |
| DE-AC | 0.9 ± 0.1 |
| DE-AG[a] | 2.3 ± 0.7 |
| DE-AGL[a] | 3.4 ± 0.9 |
| DE-EC | 1.5 ± 0.4 |
| DE-EG | 2.0 ± 0.5 |
| DE-EGL | 1.5 ± 0.5 |
| DE-NC | 1.1 ± 0.2 |
| DE-NG[a] | 1.9 ± 0.1 |
| DE-NGL | 1.7 ± 0.8 |

[a]indicated statistical difference (p < 0.05) compared to the control scaffolds.

TABLE 4

Reported modulus values from various types of acellular tissues.

| Decellularized tissues | Modulus | Reference |
| --- | --- | --- |
| Cardiac tissue | 0.2 MPa | Eitan et al., 2010 [60] |
| Dermis | 60 MPa | Hoganson et al., 2010 [61] |
| Heart valve | 1 MPa | Lichtenberg et al., 2006 [62] |
| Kidney | 0.2 MPa | Nakayama et al., 2010 [63] |
| Tendon | 76 MPa | Youngstrom et al., 2013 [71] |
| Tracheal | 1-2 MPa | Zang et al., 2012 [64] |
| Adipose | 0.5-8 MPa | Choi et al., 2011 [65] |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Examples of claimed embodiments of the invention include, but are not limited to:

1. An acellular ECM that can recapitulate developmental cues and/or provide for specific biological properties.

2. The acellular ECM of embodiment 1, wherein the stem cells are embryonic stem cells.

3. The acellular ECM of embodiment 1, wherein the stem cells are human stem cells.

4. A method for preparing an acellular ECM, wherein the method comprises culturing stem cells as 3-D aggregates or as EBs for a sufficient period of time, followed by decellularization using a decellularization reagent, such as a surfactant and/or detergent, and subsequently a nuclease, such as a DNase and obtaining an acellular ECM.

5. The method of embodiment 4, wherein the cells are grown in a bioreactor.

6. The method of embodiment 4, wherein the cells are grown for 1-3 days prior to decellularization.

7. The method of embodiment 4, wherein the cells are grown for 4-10 days prior to decellularization.

8. The method of embodiment 4, wherein the stem cells are embryonic stem cells.

9. The method of embodiment 4, wherein the stem cells are human stem cells.

10. The method of embodiment 4, wherein the cells are grown in a differentiation medium.

11. The method of embodiment 4, wherein the decellularization step comprises treating the cells for about 30 minutes with 1% Triton X-100 and about 30 minutes with DNase I.

12. A method for tissue engineering, regeneration of tissue or an organ, wound healing, and/or treatment of a disease or condition, comprising administering an acellular ECM of the present invention to a person or animal.

13. The method of embodiment 12, wherein the disease to be treated is a cancer.

REFERENCES

1. Thomson, J. A., Itskovitz-Eldor, J., Shapiro, S. S., Waknitz, M. A., Swiergiel, J. J., Marshall, V. S., Jones, J. M. Embryonic stem cell lines derived from human blastocysts. Science 282, 1145, 1998.

2. Takahashi, K., Tanabe, K., Ohnuki, M., Narita, M., Ichisaka, T., Tomoda, K., Yamanaka, S. Induction of pluripotent stem cells from adult human fibroblasts by defined factors. Cell 131, 861, 2007.
3. Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., Slukvin, II. Thomson, J. A. Induced pluripotent stem cell lines derived from human somatic cells. Science 318, 1917, 2007.
4. Rozario, T., and DeSimone, D. W. The extracellular matrix in development and morphogenesis: a dynamic view. Dev Biol 341, 126, 2010.
5. Hynes, R. O. The extracellular matrix: not just pretty fibrils. Science 326, 1216, 2009.
6. Hughes, C., Radan, L., Chang, W. Y., Stanford, W. L., Betts, D. H., Postovit, L. M., Lajoie, G. A. Mass Spectrometry-Based Proteomics Analysis of the Matrix Microenvironment in Pluripotent Stem Cell Culture. Mol Cell Proteomics 2012, 11:1924-1936.
7. Hunt, G. C., Singh, P., Schwarzbauer, J. E. Endogenous production of fibronectin is required for self-renewal of cultured mouse embryonic stem cells. Exp Cell Res 318, 1820, 2012.
8. Chen, S. S., Fitzgerald, W., Zimmerberg, J., Kleinman, H. K., Margolis, L. Cell-cell and cell-extracellular matrix interactions regulate embryonic stem cell differentiation. STEM CELLS 25, 553, 2007.
9. Przybyla, L., and Voldman, J. Probing embryonic stem cell autocrine and paracrine signaling using microfluidics Annu Rev Anal Chem (Palo Alto Calif.) 5, 293, 2012.
10. Nair, R., Ngangan, A. V., Kemp, M. L., McDevitt, T. C. Gene Expression Signatures of Extracellular Matrix and Growth Factors during Embryonic Stem Cell Differentiation. PLoS One 7, e42580, 2012.
11. Nair, R., Shukla, S., McDevitt, T. C. Acellular matrices derived from differentiating embryonic stem cells. J Biomed Mater Res A 87, 1075, 2008.
12. Ngangan, A. V., and McDevitt, T. C. Acellularization of embryoid bodies via physical disruption methods. Biomaterials 30, 1143, 2009.
13. Choi, J. S., Yang, H. J., Kim, B. S., Kim, J. D., Kim, J. Y., Yoo, B., Park, K., Lee, H. Y., Cho, Y. W. Human extracellular matrix (ECM) powders for injectable cell delivery and adipose tissue engineering. J Control Release 139, 2, 2009.
14. Turner, A. E., and Flynn, L. E. Design and characterization of tissue-specific extracellular matrix-derived microcarriers. Tissue Eng Part C Methods 18, 186, 2012.
15. Turner, A. E., Yu, C., Bianco, J., Watkins, J. F., Flynn, L. E. The performance of decellularized adipose tissue microcarriers as an inductive substrate for human adipose-derived stem cells. Biomaterials 33, 4490, 2012.
16. Lu, H., Hoshiba, T., Kawazoe, N., Chen, G. Autologous extracellular matrix scaffolds for tissue engineering. Biomaterials 32, 2489, 2011.
17. Kim, J., and Ma, T., Autocrine fibroblast growth factor 2-mediated interactions between human mesenchymal stem cells and the extracellular matrix under varying oxygen tension. J Cell Biochem 2012, doi: 10.1002/jcb.24413.
18. Sart, S., Errachid, A., Schneider, Y. J., Agathos, S. N. Modulation of mesenchymal stem cell actin organization on conventional microcarriers for proliferation and differentiation in stirred bioreactors. J Tissue Eng Regen Med 2012, doi: 10.1002/term.545.
19. Lock, L. T., and Tzanakakis, E. S. Expansion and differentiation of human embryonic stem cells to endoderm progeny in a microcarrier stirred-suspension culture. Tissue Eng Part A 15, 2051, 2009.
20. Postovit, L. M., Margaryan, N. V., Seftor, E. A., Kirschmann, D. A., Lipaysky, A., Wheaton, W. W., Abbott, D. E., Seftor, R. E., Hendrix, M. J. Human embryonic stem cell microenvironment suppresses the tumorigenic phenotype of aggressive cancer cells. Proc Natl Acad Sci USA 105, 4329, 2008.
21. Postovit, L. M., Seftor, E. A., Seftor, R. E., Hendrix, M. J. A three-dimensional model to study the epigenetic effects induced by the microenvironment of human embryonic stem cells. STEM CELLS 24, 501, 2006.
22. Fok, E. Y., and Zandstra, P. W. Shear-controlled single-step mouse embryonic stem cell expansion and embryoid body-based differentiation. STEM CELLS 23,1333, 2005.
23. Bratt-Leal, A. M., Carpenedo, R. L., McDevitt, T. C. Engineering the embryoid body microenvironment to direct embryonic stem cell differentiation. Biotechnol Prog 25, 43, 2009.
24. Xu, C., Inokuma, M. S., Denham, J., Golds, K., Kundu, P., Gold, J. D., Carpenter, M. K. Feeder-free growth of undifferentiated human embryonic stem cells. Nat Biotechnol 19, 971, 2001.
25. Zweigerdt, R., Olmer, R., Singh, H., Haverich, A., Martin, U. Scalable expansion of human pluripotent stem cells in suspension culture. Nat Protoc 6, 689, 2011.
26. Azarin, S. M., Lian, X., Larson, E. A., Popelka, H. M., de Pablo, J. J., Palecek, S. P. Modulation of Wnt/beta-catenin signaling in human embryonic stem cells using a 3-D microwell array. Biomaterials 33, 2041, 2012.
27. Kraushaar, D. C., Rai, S., Condac, E., Nairn, A., Zhang, S., Yamaguchi, Y., Moremen, K., Dalton, S., Wang, L. Heparan sulfate facilitates FGF and BMP signaling to drive mesoderm differentiation of mouse embryonic stem cells. J Biol Chem 287, 22691, 2012.
28. Farina, A., D'Aniello, C., Severino, V., Hochstrasser, D. F., Parente, A., Minchiotti, G., Chambery, A. Temporal proteomic profiling of embryonic stem cell secretome during cardiac and neural differentiation. Proteomics 11, 3972, 2011.
29. Sachlos, E., and Auguste, D. T. Embryoid body morphology influences diffusive transport of inductive biochemicals: a strategy for stem cell differentiation. Biomaterials 29, 4471, 2008.
30. Ulloa, L., and Tabibzadeh, S. Lefty inhibits receptor-regulated Smad phosphorylation induced by the activated transforming growth factor-beta receptor. J Biol Chem 276, 21397, 2001.
31. Zhang, P., Li, J., Tan, Z., Wang, C., Liu, T., Chen, L., Yong, J., Jiang, W., Sun, X., Du, L., Ding, M., Deng, H. Short-term BMP-4 treatment initiates mesoderm induction in human embryonic stem cells. Blood 111, 1933, 2008.
32. Okada, Y., Shimazaki, T., Sobue, G., Okano, H. Retinoic-acid-concentration-dependent acquisition of neural cell identity during in vitro differentiation of mouse embryonic stem cells. Dev Biol 275, 124, 2004.
33. Sart, S., Ma, T., Li, Y. Cryopreservation of pluripotent stem cell aggregates in defined protein-free formulation. Biotechnol Prog, 2013, 29:143-153.
34. Nair, R., Ngangan, A. V., McDevitt, T. C. Efficacy of solvent extraction methods for acellularization of embryoid bodies. J Biomater Sci Polym Ed 19, 801, 2008.
35. Lu, H., Hoshiba, T., Kawazoe, N., Chen, G. Comparison of decellularization techniques for preparation of extracellular matrix scaffolds derived from three-dimensional cell culture. J Biomed Mater Res A 100, 2507, 2012.

36. Grayson, W. L., Ma, T., Bunnell, B. Human mesenchymal stem cells tissue development in 3D PET matrices. Biotechnol Prog 20, 905, 2004.
37. Li, X., Chen, Y., Scheele, S., Arman, E., Haffner-Krausz, R., Ekblom, P., Lonai, P. Fibroblast growth factor signaling and basement membrane assembly are connected during epithelial morphogenesis of the embryoid body. J Cell Biol 153, 811, 2001.
38. Matsuoka, Y., Kubota, H., Adachi, E., Nagai, N., Marutani, T., Hosokawa, N., Nagata, K. Insufficient folding of type IV collagen and formation of abnormal basement membrane-like structure in embryoid bodies derived from Hsp47-null embryonic stem cells. Mol Biol Cell 15, 4467, 2004.
39. Badylak, S. F., Freytes, D. O., Gilbert, T. W. Extracellular matrix as a biological scaffold material: Structure and function. Acta Biomater 5, 1, 2009.
40. Brafman, D. A., Shah, K. D., Fellner, T., Chien, S., Willert, K. Defining long-term maintenance conditions of human embryonic stem cells with arrayed cellular microenvironment technology. Stem Cells Dev 18, 1141, 2009.
41. Lee, S. T., Yun, J. I., Jo, Y. S., Mochizuki, M.; van der Vlies, A. J., Kontos, S., Ihm, J. E., Lim, J. M., Hubbell, J. A. Engineering integrin signaling for promoting embryonic stem cell self-renewal in a precisely defined niche. Biomaterials 31, 1219, 2010.
42. Persaud, S. D., Lin, Y. W., Wu, C. Y.; Kagechika, H., Wei, L. N. Cellular retinoic acid binding protein I mediates rapid non-canonical activation of ERK1/2 by all-trans retinoic acid. Cell Signal 25, 19, 2012.
43. Sharow, K. A., Temkin, B., Asson-Batres, M. A. Retinoic acid stability in stem cell cultures. Int J Dev Biol 56, 273, 2012.
44. Belatik, A., Hotchandani, S., Bariyanga, J., Tajmir-Riahi, H. A. Binding sites of retinol and retinoic acid with serum albumins. Eur J Med Chem 48, 114, 2012.
45. Kennedy, K. A., Porter, T., Mehta, V., Ryan, S. D., Price, F., Peshdary, V., Karamboulas, C., Savage, J., Drysdale, T. A.; Li, S. C.; Bennett, S. A., Skerjanc, I. S. Retinoic acid enhances skeletal muscle progenitor formation and bypasses inhibition by bone morphogenetic protein 4 but not dominant negative beta-catenin. BMC Biol 7, 67, 2009.
46. Micallef, S. J., Janes, M. E., Knezevic, K., Davis, R. P., Elefanty, A. G., Stanley, E. G. Retinoic acid induces Pdx 1-positive endoderm in differentiating mouse embryonic stem cells. Diabetes 54, 301, 2005.
47. Simandi, Z., Balint, B. L., Poliska, S., Ruhl, R., Nagy, L. Activation of retinoic acid receptor signaling coordinates lineage commitment of spontaneously differentiating mouse embryonic stem cells in embryoid bodies. FEBS Lett 584, 3123, 2010.
48. Carpenedo, R. L., Bratt-Leal, A. M., Marklein, R. A., Seaman, S. A., Bowen, N. J., McDonald, J. F., McDevitt, T. C. Homogeneous and organized differentiation within embryoid bodies induced by microsphere-mediated delivery of small molecules. Biomaterials 30, 2507, 2009.
49. Chen, N., and Napoli, J. L. All-trans-retinoic acid stimulates translation and induces spine formation in hippocampal neurons through a membrane-associated RARalpha. FASEB J 22, 236, 2008.
50. Bratt-Leal, A. M., Carpenedo, R. L., Ungrin, M. D., Zandstra, P. W., McDevitt, T. C. Incorporation of biomaterials in multicellular aggregates modulates pluripotent stem cell differentiation. Biomaterials 32, 48, 2011.
51. Sart S, Ma T, Li Y. Extracellular matrices decellularized from embryonic stem cells maintained their structure and signaling specificity. Tissue Engineering Part A2014, 20:54-66.
52. Liang H C, Chang Y, Hsu C K, Lee M H, Sung H W. Effects of crosslinking degree of an acellular biological tissue on its tissue regeneration pattern. Biomaterials. 2004; 25:3541-52.
53. Keung A J, Asuri P, Kumar S, Schaffer D V. Soft microenvironments promote the early neurogenic differentiation but not self-renewal of human pluripotent stem cells. Integr Biol (Camb). 2012; 4:1049-58.
54. Saha K, Keung A J, Irwin E F, Li Y, Little L, Schaffer D V, et al. Substrate modulus directs neural stem cell behavior. Biophys J. 2008; 95:4426-38.
55. Leipzig N D, Shoichet M S. The effect of substrate stiffness on adult neural stem cell behavior. Biomaterials. 2009; 30:6867-78.
56. Sart S, Liu Y, Ma T, Li Y. Microenvironment regulation of pluripotent stem cell-derived neural progenitor aggregates by human mesenchymal stem cell secretome. Tissue Engineering Part A. 2013; Submitted.
57. Butler M F, NG Y-F, PUDNEY PDA. Mechanism and kinetics of the crosslinking reaction between biopolymers containing primary amine groups and Genipin. Journal of Polymer Science: Part A: Polymer Chemistry. 2003; 41:3941-53.
58. Goncalves M B, Boyle J, Webber D J, Hall S, Minger S L, Corcoran J P. Timing of the retinoid-signalling pathway determines the expression of neuronal markers in neural progenitor cells. Dev Biol. 2005; 278:60-70.
59. Kothapalli C R, Kamm R D. 3D matrix microenvironment for targeted differentiation of embryonic stem cells into neural and glial lineages. Biomaterials. 2013; 34:5995-6007.
60. Eitan Y, Sarig U, Dahan N, Machluf M. Acellular cardiac extracellular matrix as a scaffold for tissue engineering: in vitro cell support, remodeling, and biocompatibility. Tissue Eng Part C Methods. 2010; 16:671-83.
61. Hoganson DM, O'Doherty E M, Owens G E, Harilal D O, Goldman S M, Bowley C M, et al. The retention of extracellular matrix proteins and angiogenic and mitogenic cytokines in a decellularized porcine dermis. Biomaterials. 2010; 31:6730-7.
62. Lichtenberg A, Tudorache I, Cebotari S, Ringes-Lichtenberg S, Sturz G, Hoeffler K, et al. In vitro re-endothelialization of detergent decellularized heart valves under simulated physiological dynamic conditions. Biomaterials. 2006; 27:4221-9.
63. Nakayama K H, Batchelder C A, Lee C I, Tarantal A F. Decellularized rhesus monkey kidney as a three-dimensional scaffold for renal tissue engineering. Tissue Eng Part A. 2010; 16:2207-16.
64. Zang M, Zhang Q, Chang E I, Mathur A B, Yu P. Decellularized tracheal matrix scaffold for tissue engineering. Plast Reconstr Surg. 2012; 130:532-40.
65. Choi J S, Kim B S, Kim J Y, Kim J D, Choi Y C, Yang H J, et al. Decellularized extracellular matrix derived from human adipose tissue as a potential scaffold for allograft tissue engineering. J Biomed Mater Res A. 2011; 97:292-9.
66. Yan L P, Wang Y J, Ren L, Wu G, Caridade S G, Fan J B, et al. Genipin-cross-linked collagen/chitosan biomimetic scaffolds for articular cartilage tissue engineering applications. J Biomed Mater Res A. 2010; 95:465-75.
67. Jiang T, Ren X J, Tang J L, Yin H, Wang K J, Zhou C L. Preparation and characterization of genipin-cross- 68. Nolte A J, Rubner M F, Cohen R E. Determining the Young's modulus of polyelectrolyte multilayer films via stress-Induced mechanical buckling instabilities. Macromolecules. 2005; 38.
69. Krieg M, Arboleda-Estudillo Y, Puech P H, Kafer J, Graner F, Muller D J, et al. Tensile forces govern germ-layer organization in zebrafish. Nat Cell Biol. 2008; 10:429-36.
70. Maitre J L, Berthoumieux H, Krens S F, Salbreux G, Julicher F, Paluch E, et al. Adhesion functions in cell sorting by mechanically coupling the cortices of adhering cells. Science. 2012; 338:253-6.
71. Youngstrom D W, Barrett J G, Jose R R, Kaplan D L. Functional characterization of detergent-decellularized equine tendon extracellular matrix for tissue engineering applications. PLoS One. 2013; 8:e64151.
72. Discher D E, Janmey P, Wang Y L. Tissue cells feel and respond to the stiffness of their substrate. Science. 2005; 310:1139-43.
73. Banerjee A, Arha M, Choudhary S, Ashton R S, Bhatia S R, Schaffer D V, et al. The influence of hydrogel modulus on the proliferation and differentiation of encapsulated neural stem cells. Biomaterials. 2009; 30:4695-9.
74. Keung A J, Dong M, Schaffer D V, Kumar S. Pan-neuronal maturation but not neuronal subtype differentiation of adult neural stem cells is mechanosensitive. Sci Rep. 2013; 3:1817.
75. Keung A J, de Juan-Pardo E M, Schaffer D V, Kumar S. Rho GTPases mediate the mechanosensitive lineage commitment of neural stem cells. STEM CELLS. 2011; 29:1886-97.
76. Engberg N, Kahn M, Petersen D R, Hansson M, Serup P. Retinoic acid synthesis promotes development of neural progenitors from mouse embryonic stem cells by suppressing endogenous, Wnt-dependent nodal signaling. STEM CELLS. 2010; 28:1498-509.
77. Li M, Pevny L, Lovell-Badge R, Smith A. Generation of purified neural precursors from embryonic stem cells by lineage selection. Curr Biol. 1998; 8:971-4.
78. Cai C, Grabel L. Directing the differentiation of embryonic stem cells to neural stem cells. Dev Dyn. 2007; 236:3255-66.
79. Tropepe V, Hitoshi S, Sirard C, Mak T W, Rossant J, van der Kooy D. Direct neural fate specification from embryonic stem cells: a primitive mammalian neural stem cell stage acquired through a default mechanism. Neuron. 2001; 30:65-78.
80. Herget T, Esdar C, Oehrlein S A, Heinrich M, Schutze S, Maelicke A, et al. Production of ceramides causes apoptosis during early neural differentiation in vitro. J Biol Chem. 2000; 275:30344-54.
81. Rowland J W, Lee J J, Salewski R P, Eftekharpour E, van der Kooy D, Fehlings M G. Generation of neural stem cells from embryonic stem cells using the default mechanism: in vitro and in vivo characterization. Stem Cells Dev. 2011; 20:1829-45.
82. Stergiopoulos A, Politis P K. The role of nuclear receptors in controlling the fine balance between proliferation and differentiation of neural stem cells. Arch Biochem Biophys. 2013; 534:27-37.
83. Yu S, Levi L, Siegel R, Noy N. Retinoic acid induces neurogenesis by activating both retinoic acid receptors (RARs) and peroxisome proliferator-activated receptor beta/delta (PPARbeta/delta). J Biol Chem. 2012; 287: 42195-205.
84. Mereau A, Grey L, Piquet-Pellorce C, Heath J K. Characterization of a binding protein for leukemia inhibitory factor localized in extracellular matrix. J Cell Biol. 1993; 122:713-9.
85. Martino G, Pluchino S, Bonfanti L, Schwartz M. Brain regeneration in physiology and pathology: the immune signature driving therapeutic plasticity of neural stem cells. Physiol Rev. 2011; 91:1281-304.
86. Santos T, Ferreira R, Maia J, Agasse F, Xapelli S, Cortes L, et al. Polymeric nanoparticles to control the differentiation of neural stem cells in the subventricular zone of the brain. ACS Nano. 2012; 6:10463-74.

We claim:

1. A method for preparing an extracellular matrix (ECM), said method comprising growing stem cells as aggregates or embryoid bodies (EB) in a suspension culture comprising a growth medium for at least three days to allow for production of an ECM, wherein said growth medium comprises one or more of leukemia inhibitory factor (LIF), retinoic acid (RA), or bone morphogenic protein (BMP) and subsequently removing the cells by treating with a surfactant or detergent, and a nuclease, wherein an acellular extracellular matrix remains following cell removal, and wherein the method further comprises cross-linking said acellular ECM following cell removal.

2. The method according to claim 1, wherein said stem cell is a pluripotent stem cell or an embryonic stem cell.

3. The method according to claim 1, wherein said stem cell is a human stem cell.

4. The method according to claim 1, wherein said surfactant or detergent is Triton X-100 or Sodium dodecyl sulfate (SDS).

5. The method according to claim 1, wherein said nuclease is DNase I.

6. The method according to claim 1, wherein treatment with said surfactant or detergent ranges from about 15 minutes to about 60 minutes.

7. The method according to claim 1, wherein treatment with said surfactant or detergent and said nuclease comprises treatment with 1% Triton X-100 for about 30 minutes followed by treatment with DNase I for about 30 minutes.

8. The method according to claim 1, wherein said acellular ECM is cross-linked using Genipin.

9. The method according to claim 1, wherein said acellular ECM is cross-linked using 3% genipin for 3 to 9 hours.

10. The method according to claim 1, wherein said cells are grown in said suspension culture with an ultra-low attachment substrate.

11. The method according to claim 1, wherein said EB are grown for up to about 10 days in growth medium comprising retinoic acid or a bone morphogenic protein (BMP).

12. The method according to claim 1, wherein said cells are grown under conditions to produce ECM that favors undifferentiated cell growth when said ECM is reseeded with cells.

13. The method according to claim 1, wherein said ECM is in the form of microspheres.

14. The method according to claim 1, wherein said ECM is in the form of a three dimensional shape of a bone or tissue or a portion of a bone or tissue.

15. The method according to claim 1, wherein treatment with said nuclease ranges from about 15 minutes to about 60 minutes.

16. The method according to claim 1, wherein said acellular ECM is cross-linked using 3% genipin for about 5 to 7 hours.

17. The method according to claim 1, wherein said acellular ECM is cross-linked using 3% genipin for about 6 hours.

18. The method according to claim 1, wherein said step of growing said stem cells in said suspension culture is for a period of time of 4 to 10 days in said suspension culture.

19. The method according to claim 1, wherein said ECM is reseeded with embryonic stem cells following cell removal and cross-linking of said ECM.

* * * * *

UNITED STATES PATENT AND TRADEMARK OFFICE
CERTIFICATE OF CORRECTION

PATENT NO. : 10,035,980 B2
APPLICATION NO. : 14/760945
DATED : July 31, 2018
INVENTOR(S) : Yan Li, Teng Ma and Sebastien Sart It is certified that error appears in the above-identified patent and that said Letters Patent is hereby corrected as shown below:

In the Specification

Column 23
Line 2, "α-Tubulin" should read --β-Tubulin--.

Signed and Sealed this
Seventh Day of May, 2019

Andrei Iancu
*Director of the United States Patent and Trademark Office*